United States Patent
Lichti et al.

(10) Patent No.: US 9,775,801 B2
(45) Date of Patent: Oct. 3, 2017

(54) COMPOSITION AND METHOD FOR MANAGEMENT OF DIABETES OR PRE-DIABETES

(71) Applicant: Omniblend Innovation PTY Ltd., Campbellfield, Victoria (AU)

(72) Inventors: Christopher Walter Lichti, Essendon (AU); Peter Richard Wynter Best, Tamworth (AU); Janena Frances Best, Tamworth (AU); Gottfried Lichti, Essendon (AU)

(73) Assignee: Omniblend Innovation Pty Ltd., Campbellfield, Victoria (AU)

(*) Notice: Subject to any disclaimer, the term of this patent is extended or adjusted under 35 U.S.C. 154(b) by 0 days.

(21) Appl. No.: 15/464,144

(22) Filed: Mar. 20, 2017

(65) Prior Publication Data
US 2017/0189332 A1  Jul. 6, 2017

Related U.S. Application Data

(62) Division of application No. 14/403,092, filed as application No. PCT/AU2013/000537 on May 22, 2013, now Pat. No. 9,675,553.
(Continued)

(30) Foreign Application Priority Data

Sep. 14, 2012 (AU) ................................ 2012904029
Apr. 12, 2013 (AU) ................................ 2013204801

(51) Int. Cl.
*A61K 9/00* (2006.01)
*A61K 31/736* (2006.01)
(Continued)

(52) U.S. Cl.
CPC .............. *A61K 9/0095* (2013.01); *A23L 2/66* (2013.01); *A23L 33/17* (2016.08); *A23L 33/40* (2016.08);
(Continued)

(58) Field of Classification Search
CPC ................................................... A61K 9/0095
See application file for complete search history.

(56) References Cited

U.S. PATENT DOCUMENTS

| 4,315,918 A | 2/1982 | Gayst et al. |
| 4,921,877 A | 5/1990 | Cashmere et al. |

(Continued)

FOREIGN PATENT DOCUMENTS

| CA | 1221575 A1 | 5/1987 |
| EP | 0083327 B1 | 3/1985 |

(Continued)

OTHER PUBLICATIONS

Yoshimura et al., "Rheological Studies of Influence of Dietary Fibers on the Enzymatic Reaction for Soy Protein Isolate," Foods & Food Ingredients J. Jpn. 210(10):954-962 (2005).
(Continued)

*Primary Examiner* — Benjamin Packard
(74) *Attorney, Agent, or Firm* — LeClairRyan, a Professional Corporation

(57) ABSTRACT

A drink for moderating blood glucose levels produced by a meal in a human subject suffering diabetes or impaired glucose tolerance (IGT) the drink comprising:
at least one water soluble or water dispersible compound selected from the group consisting of amino acids, peptides and proteins in a total amount of at least 8g on a dry weight basis per serving of drink;
aqueous liquid in an amount of from 70 ml to 400 ml (preferably in an amount of from 100 ml to 250 ml and more preferably from 125 ml to 175 ml) per serving, and (Continued)

wherein the drink exhibits shear banding when subject to the shear banding test herein described.

16 Claims, 24 Drawing Sheets

Related U.S. Application Data

(60) Provisional application No. 61/650,769, filed on May 23, 2012.

(51) Int. Cl.
    *A61K 35/20*     (2006.01)
    *A23L 2/66*     (2006.01)
    *A23L 33/00*     (2016.01)
    *A23L 33/17*     (2016.01)
    *A61J 1/14*     (2006.01)
    *B65D 25/56*     (2006.01)

(52) U.S. Cl.
    CPC ........... *A61J 1/1412* (2013.01); *A61K 31/736* (2013.01); *A61K 35/20* (2013.01); *B65D 25/56* (2013.01); *A23V 2002/00* (2013.01)

(56) References Cited

U.S. PATENT DOCUMENTS

| | | | |
|---|---|---|---|
| 5,104,676 | A | 4/1992 | Mahmoud et al. |
| 6,365,176 | B1 | 4/2002 | Bell et al. |
| 6,383,551 | B1 | 5/2002 | Foegeding et al. |
| 7,977,319 | B1 | 7/2011 | Levine |
| 2004/0087514 | A1 | 5/2004 | Hughes et al. |
| 2005/0058671 | A1 | 3/2005 | Bedding et al. |
| 2006/0159770 | A1 | 7/2006 | Garcia-Rodenas et al. |
| 2006/0171992 | A1 | 8/2006 | Gerhardt et al. |
| 2006/0275506 | A1 | 12/2006 | Fisher et al. |
| 2008/0311265 | A1 | 12/2008 | MacDonald et al. |
| 2009/0018196 | A1 | 1/2009 | Bjork et al. |
| 2010/0056450 | A1 | 3/2010 | Brown et al. |

FOREIGN PATENT DOCUMENTS

| | | | |
|---|---|---|---|
| GB | 2432772 | A | 6/2007 |
| WO | 03105882 | A1 | 12/2003 |
| WO | 2004022074 | A1 | 3/2004 |
| WO | 2011075691 | A1 | 6/2011 |

OTHER PUBLICATIONS

International Preliminary Report on Patentability for corresponding application No. PCT/AU2013/000537 mailed Sep. 19, 2014.
Anderson et al., "Effects of Psyllium on Glucose and Serum Lipid Responses in Men with Type 2 Diabetes and Hypercholesterolemia," Am J Clin Nutr 70:466-73 (1999).
Claessens et al., "Glucagon and Insulin Responses After Ingestion of Different Amounts of Intact and Hydrolysed Proteins," British Journal of Nutrition 100:61-69 (2008).
Edwards et al., "Viscosity of Food Gums Determined in Vitro Related to Their Hypoglycemic Actions," Am J Clin Nutr 46:72-7 (1987.
Gerdes, "U.S. Whey Ingredients and Weight Management," U.S. Dairy Export Council, eL.1-eL.8 (2003).
Luhovyy et al., "Whey Proteins in the Regulation of Food Intake and Satiety," Journal of the American College of Nutrition 26(6): 704S-712S (2007).
Ma et al, "Effects of a Protein Preload on Gastric Emptying, Glycemia, and Gut Hormones After a Carbohydrate Meal in Diet-Controlled Type 2 Diabetes," Diabetes Care 32(9):1600-1602 (2009).
Power et al., "Human Insulinotropic Response to Oral Ingestion of Native and Hydrolysed Whey Protein," Amino Acids 37:333-339 (2009).
Rittmanic, "U.S. Whey Proteins in Ready-To-Drink Beverages," U.S. Dairy Export Council, e3.7.1-e3.7.8 (2006).
USDEC Library, "Manuals, Guides, & Monographs," http://www.usdec.org/Library/Guides.cfm, 2 pages. (2012).

COMPOSITION AND METHOD FOR MANAGEMENT OF DIABETES OR PRE-DIABETES

This application is a divisional of U.S. patent application Ser. No. 14/403,092, filed 22 May 2013, which is a national stage application under 35 U.S.C. §371 of PCT Application No. PCT/AU2013/000537, filed 22 May 2013, which claims priority from U.S. Provisional Patent Application Ser. No. 61/650769 of 23 May 2012; Australian Application 2012904029 of 14 Sep. 2012 and Australian Application 2013204801 of 12 Apr. 2013.

FIELD OF THE INVENTION

This invention relates to improved drink formulations for use by people with diabetes or impaired glucose tolerance (IGT) often referred to as pre-diabetes. In particular the invention relates to functional drinks that are taken in association with meals or in association with oral medications, and that moderate post-prandial glucose levels such as by reducing postprandial peak blood sugar level, or reducing postprandial blood sugar area under the curve (AUC) of blood sugar level vs time. Embodiments also relate to a method of treatment diabetes and IGT and kit for use in treatment of diabetes and IGT and use of a composition for manufacture of a medicament for treatment of diabetes and IGT.

BACKGROUND OF THE INVENTION

Impaired glucose tolerance (IGT) is a pre-diabetic state of dysglycemia that is associated with insulin resistance and increased risk of cardiovascular pathology. IGT may precede type 2 diabetes mellitus by many years. IGT is also a risk factor for mortality. According to the criteria of the World Health Organization and the American Diabetes Association, impaired glucose tolerance is defined as two-hour glucose levels of 140 to 199 mg per dL (7.8 to 11.0 mmol) on the 75-g oral glucose tolerance test. A patient is said to be under the condition of IGT when he/she has an intermediately raised glucose level after 2 hours, but less than would qualify for type 2 diabetes mellitus. The fasting glucose may be either normal or mildly elevated.

Diabetes includes Type 1, Type 2 and Gestational Diabetes. Type 1 diabetes: results from the body's failure to produce insulin, and presently requires the person to inject insulin. (Also referred to as insulin-dependent diabetes mellitus, IDDM for short, and juvenile diabetes.)

Type 2 diabetes: results from insulin resistance, a condition in which cells fail to use insulin properly, sometimes combined with an absolute insulin deficiency. (Formerly referred to as non-insulin-dependent diabetes mellitus, NIDDM for short, and adult-onset diabetes.)

Gestational diabetes: is when pregnant women, who have never had diabetes before, have a high blood glucose level during pregnancy. It may precede development of type 2 DM.

Other forms of diabetes mellitus include congenital diabetes, which is due to genetic defects of insulin secretion, cystic fibrosis-related diabetes, steroid diabetes induced by high doses of glucocorticoids, and several forms of monogenic diabetes.

Both type 1 and 2 are chronic conditions that usually cannot be cured.

A number of studies have been conducted to examine the effect of diet supplements, particularly high fibre supplements on control of post-prandial glucose in healthy and diabetic subjects.

Chandalia et al. in "Beneficial Effects of High Dietary Fiber Intake in Patients with Type 2 Diabetes Mellitus", New England Journal of Medecine 2000; 342: 1392-1398, May 1, 2000, note that the American Dietary Association (ADA) recommended a moderate increase in the intake of dietary fiber to 20-35 g per day because of the cholesterol-lowering effects of soluble fibers. However, the effects of dietary fiber on glycemic control were considered (by ADA) to be inconsequential. Furthermore the expert panel of the ADA considered it difficult to achieve a high dietary intake of soluble fiber without consuming foods or supplements fortified with fiber. The above authors designed a study to determine the effects on glycemic control of increasing the intake of dietary fiber in patients with type 2 diabetes exclusively through the consumption of unfortified foods, to a level beyond that recommended by the ADA. Two diets were compared: a diet in accordance with ADA with moderate amounts of fiber (total 24 g per day, of which 8 g soluble fiber and 16 g insoluble fiber), and a diet with a high amount of fiber (total 50g per day of which 25 g soluble fiber and 25 g insoluble fiber). Both diets provided 15% of the total energy as protein. The high-fiber diet (which contained significant quantities of protein) was found to improve glycemic control, as evidenced by decreases in the mean daily preprandial and 24-hr plasma glucose concentrations, and also by lowered urinary glucose excretion.

Anderson et al. in "Effects of psyllium on glucose and serum lipid responses in men with type 2 diabetes and hypercholesterolemia", The American Journal of Clinical Nutrition, October 1999 vol. 70 no 466-473 provided diabetic subjects with soluble psyllium fibers presented as a powder inside a sachet, with instructions to mix each dose of 8.7 g psyllium in 240 ml liquid and to drink the liquid 20-30 minutes before the morning and evening meals. The psyllium was provided as an orange-flavoured, sugar-free product (Metamucil; Procter and Gamble Co, Cincinnati). The control drink included an insoluble cellulose fiber, microcrystalline cellulose (Avicel, PH-101, FMC Corp, Philadelphia). For patients evaluated in the metabolic ward, psyllium showed improved metabolic control (lower blood sugar) than the control. Many changes in glycemic index during the outpatient evaluations were not significantly different.

In the introduction to the above article by Anderson et al., the authors report that early studies suggested that psyllium improved glycemic control in individuals with type 2 diabetes (e.g. Fagerberg SE, "The effects of a bulk laxative (Metamucil) on fasting blood glucose, serum lipids and other variables in constipated patients with non-insulin dependent adult diabetes", Curr Ther Res 1982; 31:166-72) but that other studies showed no effect on glycemic control (e.g. Br J Nutr 1984; 51:371-8), and yet others found an effect only when psyllium was sprinkled onto or incorporated into a cereal meal.

With respect to the ingestion of the psyllium-based material Metamucil, it is noteworthy that the makers of Metamucil have advocated convenient and tasty recipes for consuming Metamucil fiber, and that one of these recipes has included the incorporation of Metamucil (e.g. 1 rounded teaspoon) in a milk shake (e.g. based on 8 oz of low-fat milk). The administration of Metamucil in this way as part of a disease management strategy for type 2 diabetes would provide a combination of fiber and protein, and in particular would provide a combination of fiber and whey protein. Nuttal et al. in "Effect of protein ingestion on the glucose and insulin response to a standardised oral glucose load", Diabetes Care, 1984 September-October; 7(5): 465-70 found that protein given with glucose will increase insulin secretion and reduce the plasma glucose rise in at least some type 2 diabetic persons. The glucose meal is generally seen as representative of a high GI meal.

Gannon et al. in "The insulin and glucose responses to meals of glucose plus various proteins in type 2 diabetic subjects" Metabolism, 1988 November; 37(11): 1081-8, report prior work that shows that ingested beef protein is just as potent as glucose in stimulating a rise in insulin concentration in type 2 diabetes patients. They also report a synergistic effect (in insulin secretion) when the protein is given with glucose. A study was made of a meal consisting of 50 g glucose with 25 g protein in the form of lean beef, turkey, gelatine, egg white, cottage cheese, fish or soy. It is of interest to note that cottage cheese is a cheese curd product that is drained but not pressed, so that some whey remains. Gannon et al. found that the blood glucose response was diminished following ingestion of all meals containing protein, with the exception of egg white. These authors also found that the relative area under the insulin response curve was greatest following ingestion of the meal containing cottage cheese (360%), and was least with egg white (190%), compared with glucose alone (100%).

Bell and Shabert in U.S. Pat. No. 6,365,176 (filed Sep. 18, 2000) describe a nutritional supplement to be incorporated into the diet of a type 2 diabetic or an individual having lipodystrophy. The supplement provides food-grade ingredients to improve the management of blood glucose and blood lipid levels. The supplement comprises a low GI carbohydrate and a protein, and the carbohydrate preferably includes a fiber which may be psyllium. The protein is preferably selected from the group consisting of whey, casein, soy, milk, egg and combinations thereof claim 25 is to a supplement containing from about 1 to about 10 grams protein, and from about 0.5 to about 11 grams psyllium fiber. Claim 32 is to a method of providing an individual with nutritional supplementation that aids in the management of blood glucose levels, comprising administering to an individual in need thereof the nutritional supplement, in an amount sufficient to measure blood glucose levels. Cashmere and Besozzi in U.S. Pat. No. 4,921,877 (filed 16 Dec. 1987) describe a nutritional formula containing a unique fiber-containing carbohydrate blend and protein. The use of the formula is for the dietary management of patients with glucose intolerance. The protein source may be casein, whey or soy protein.

In Stevens et al., "Effects of a protein preload on gastric emptying, glycemia, and gut hormones after a carbohydrate meal in diet-controlled type 2 diabetics", Diabetes Care, 2009 September; 32 (9):1600-2, Epub 2009 Jun. 18 describes an experiment where subjects ingested 350 ml of beef-flavoured soup containing 55 g whey protein 30 minutes before a mashed potato meal. The postprandial glycemic peak was significantly lower than in the absence of a whey preload.

Larrauri et al., "Measurement of Health-Promoting Properties in Fruit Dietary Fibres: Antioxidant capacity, Fermrntability and Glucose Retardation Index", Journal of the Science of Food and Agriculture, vol 71, Issue 4, pp 515-519 1996 discuss the glucose retardation index of a variety of fruit-derived dietary fibres. A high glucose retardation index is expected to be beneficial in terms of reduced postprandial blood sugar peaks.

Brown et al., in US application 20100056450 (filed Aug. 28, 2009) describes a method for reducing postprandial blood glucose levels, which includes administering a blend of native whey protein and viscosifying fiber to a subject in an amount and at a time prior to or concurrent with a meal, that is effective in reducing postprandial blood glucose levels. The examples in this application are based on the use of 5 g whey protein concentrate and 2 g hydroxypropylmethylcellulose in 400 ml liquid prior to or simultaneous with a standard bread meal (50 g available carbohydrate). The first claim teaches administering a blend of from 2 to 50 g whey to 0.5 to 20 g viscosifying fiber at least 5 to 90 minutes before a meal, the method effective for reducing postprandial blood glucose by at least 5% compared to the meal without preloading.

Garcia-Rodenas in US application 2006/0159770 (filed Jun. 30, 2004) teaches the use of a composition for treating, preventing and/or improving metabolic dysfunctions associated with type 2 diabetes and insulin resistance, said composition comprising intact whey protein. Garcia-Rodenas notes that US application 2003/0004095 teaches that milk protein hydrolysates can be used to improve glucose metabolism or control glycemic response in diabetics. Garcia-Rodenas teaches that the intact whey protein can be provided during, after or before a standard meal comprising carbohydrates.

Blackburn et al. in "Does guar gum improve post-prandial hyperglycaemia in humans by reducing small intestinal contact area?" British Journal of Nutrition 1984 September; 52(2): 197-204 explores the mechanism whereby viscous polysaccharides such as guar gum lower post-prandial blood glucose in humans.

Edwards et al., in "Viscosity of food gums determined in vitro related to their hypoglycaemic actions" Am J Clin Nutr 1987; 46: 72-7 note that gums which have the highest viscosity at equivalent concentrations and shear rates are not correspondingly efficient in lowering postprandial blood glucose in human subjects, when incorporated in a drink containing 50 g glucose. The drink volume was 250 mls, and the viscous solutions were presented as 1% (by weight) solutions of food gum in water.

It has been reported the consumption of guar gum in conjunction with a meal may be beneficial in reducing the blood sugar elevations caused by the meal. However powder-based drinks which contain high levels of guar and which are reconstituted before consumption may be rejected by patients on the basis of poor ("gluggy") mouth-feel. Furthermore, typical variations in the reconstitution process (e.g. shape of the drink vessel, shape of the stirring implement, variable stirring actions and stirring times) can lead to significant changes in mouth-feel and homogeneity which reduces consumer confidence in the reliability of the product, and makes the conduct of reliable clinical trials problematic.

Work by the current authors has shown that the consumption of water or water-based drinks after the ingestion of a guar drink/meal combination can adversely influence the blood sugar response to the meal. The delivery of guar gum in tablet form with a meal can also lead to variable gum dissolution kinetics as the gum is influenced by food components in the meal. The volume of water associated with the guar gum in the guar drink can also change the efficacy of the guar gum treatment.

It has also been shown that the consumption of soluble proteins (350 mls of beef-flavoured soup) as a liquid preload 30 minutes prior to a meal can reduce the blood sugar rise in type 2 diabetes patients associated with the meal. This type of effect has also been found when the meal is taken in conjunction with a broth containing soluble protein. However 350 mls is a high drink volume, and a precise teaching on a practical, uniformly effective drink for people with diabetes or pre-diabetes (such as impaired glucose tolerance=IGT) has not been provided.

The use of drinks containing both soluble proteins and viscosifying agents (with or before a meal) has also been shown to decrease blood sugar rises from the meal in healthy people (US 20100056450). In this patent application a typical individual dose of soluble protein was whey as WPC (5 g), and a typical viscosifying agent was hydroxypropylmethylcelluose (2 g). There was no investigation of effectiveness on patients with diabetes or pre-diabetes—rather an assumption was made that an effective blood sugar reduction in healthy people would automatically translate to an effective blood sugar reduction in people with diabetes or pre-diabetes. There was also no investigation of the effect of these drinks on patients on medication for the treatment of diabetes or pre-diabetes.

It is important to note that that in many type 2 diabetes patients, the blood sugar response to a meal is much more pronounced (e.g. rising to 11 millimoles/liter rather than rising to 7 mMoles/liter) and occurs over a significantly longer time period (e.g. 4 hours rather than 45 minutes) compared with a healthy subject. The assumption that a functional drink that has good efficacy for healthy subjects will also have good efficacy for diabetic or pre-diabetic subjects is thus highly questionable.

It is known that the consumption of medicines in conjunction with gel-forming fibre can slow down the kinetics of action of the medication, leading to a diminution in the efficacy of the medication. Given that many diabetics will rely on medication such as metformin, sulfonylureas or enzyme inhibitors to control their condition, and given also that most diabetic medications are recommended to be consumed at mealtimes, the use of a gel-forming fibre in a functional drink to be taken with meals may be problematic for diabetics on medication.

There is a need for improved supplements and functional foods which control post prandial glucose profile to assist in controlling the progression of IGT to diabetes and the progression in severity of diabetes from drug therapy to combination therapy and the reliance on insulin. Such management offers the potential to reduce the complications and mortality associated with diabetes and associated diseases and reduce the significant cost to public health of these diseases.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

SUMMARY OF THE INVENTION

The invention provides a drink or a drink powder for reconstitution as a drink, said drink being for use by diabetics or pre-diabetics to improve a disease parameter of diabetes or pre-diabetes, wherein the drink
　a) contains at least 8 g of water soluble or water dispersible compound selected from the group consisting of amino acids, peptides and proteins per individual serve;
　b) contains 70-400 ml of aqueous liquid per individual serve; and
　c) exhibits shear banding.

There is provided a drink for moderating blood glucose levels produced by a meal in a human subject suffering diabetes or impaired glucose tolerance (IGT) the drink comprising:
　at least one water soluble or water dispersible compound selected from the group consisting of amino acids, peptides and proteins in a total amount of at least 8 g on a dry weight basis per serving of drink;
　aqueous liquid in an amount of from 70 ml to 400 ml (preferably in an amount of from 100 ml to 250 ml and more preferably from 125 ml to 175 ml) per serving, and
wherein the drink exhibits shear banding when subject to the shear banding test herein described.

In the preferred set of embodiments the water soluble or water dispersible compound is a water soluble or water dispersible protein.

There is further provided a method for moderating the blood glucose levels produced by a meal in a subject suffering diabetes or impaired glucose tolerance, the method comprising:
　providing a unit serving of powder for preparation of a drink the powder comprising at least one water soluble or water dispersible compound selected from the group consisting of amino acids, peptides and proteins in a total amount of at least 8 g on a dry weight basis of the powder serving; and
mixing the unit serving of powder with aqueous liquid in an amount of from 70 to 400 grams of aqueous liquid per unit serving; and
administering the drink prior to ingestion of the meal;
wherein the drink exhibits shear banding on a standard rotating cylinder shear banding test as herein described.

In the preferred set of embodiments the water soluble or water dispersible compound is a water soluble or water dispersible protein.

The preferred amount of aqueous liquid is in the range of from 70 ml to 200 ml and more preferably in the range of from 125 ml to 175 ml.

There is further provided a kit for providing a serving of a drink for moderating blood glucose levels following a meal in a human subject suffering diabetes or impaired glucose tolerance (IGT) the kit comprising:
　at least one serving of water soluble or water dispersible material selected from the group consisting of amino acids, peptides and proteins in a total amount of at least 8 g on a dry weight basis per serving of drink;
　a container having a level indicating a liquid volume of from 70 ml to 400 ml;
　a closure for the container; and
　a space within the container above the level to allow vigorous mixing prior to consumption wherein the mixing of the powder with water filled to the level provides a drink which exhibits shear banding on a standard rotating cylinder shear banding test as herein described.

In the preferred set of embodiments the water soluble or water dispersible compound is a water soluble or water dispersible protein.

There is further provided a drink according to claim 1 or claim 2 wherein the water soluble or water dispersible compound is protein present in an amount of at least 8 g total on a dry weight basis per serving of drink.

In the preferred set of embodiments the water soluble or water dispersible compound is a water soluble or water dispersible protein.

In one set of embodiments it is preferred that the water soluble or water dispersible compound selected from at least one of amino acids, peptides and proteins comprises one or more amino acids selected from the group consisting of lysine, threonine, leucine, argenine, isoleucine and valine. The amino acid may be present as the amino acids themselves or amino acids joined by peptide bands in peptide or protein.

DETAILED DESCRIPTION OF THE INVENTION

We have found that, in subjects suffering diabetes or IGT, an aqueous drink composition of water soluble or water dispersible compound selected from amino acids, peptides and proteins in certain proportions is much more effective in controlling the undesirable peak in post-prandial glucose if the composition is formulated so as to exhibit shear banding. Surprisingly formulations which exhibit shear banding are not found to be more effective in controlling the peak in post-prandial glucose in healthy subjects, and in particular subjects with a blood glucose curve that returns substantially to baseline levels within 2 hours of consumption of a standard bread meal. Shear banding (see Phys Rev E Stat Nonlin Soft Matter Phys 2008 November; 78(5 Pt 1):051504. Epub 2008 Nov. 18) refers to the formation of flowing and non-flowing regions in a driven material. Quasi-two dimensional flow provides a useful tool for characterising shear banding behaviour. Shear bands have been observed in fluids with a yield stress, however, some yield-stress fluids exhibit shear banding and some do not.

Eur Phys J E Soft Matter 2010 November; 33(3):183-8. Epub 2010 Oct. 31 addresses the issue of shear band formation in yield stress fluids, and proposes that shear banding occurs in driven flow when the ratio of a characteristic relaxation time of the system to a restructuring time becomes smaller than 1.

Phys Rev E Stat Nonlin Soft Matter Phys 2008 April; 77(4 Pt 1):041507. Epub Apr. 23 shows that even in gel-like systems in a homogeneous stress situation, shear banding may occur and the width of the flowing band is determined by the macroscopically imposed shear rate rather than the stress.

Shear banding has also been described as shear localisation, and has been observed in aqueous Laponite suspensions (Phys Rev E Stat Nonlin Soft Matter Phys 2008 (March; 77(3 Pt 1):031406. Epub 2008 Mar. 20.)

Shear banding in a driven liquid is thus characterised by a band or localised region which does not exhibit significant shear spaced from the point of application of the driving force by a band or region of high shear.

In a liquid driven by a drive shaft such as a rapidly rotating cylinder in the centre of a circular container the presence of shear banding may be visually observed using a dye drop spaced from the drive shaft.

In non-shear banding liquids, a continuum of flow from rapid flow adjuvant the drive shaft to lower flows more remote from the drive shaft produce very significant distortion of a dye drop from its leading edge in the direction of rotation to the tail end. In contrast, shear banding liquids have a band or localised region without significant shear which may be visually recognised by low distortion of a dye drop from the leading edge in the direction of rotation to the tail end of the distorted dye drop.

In the context of the composition and method of the invention shear banding is a measure of the capacity of a liquid driven with high shear in the centre of a cylindrical container or tube to form a band of low shear adjacent the wall of the container or tube.

Shear banding is evident from a band of relatively low distortion of liquid adjacent the wall which may be observed using a dye drop to quantify the extent of distortion over during a time period in which the liquid is driven.

A standard shear banding test used herein to determine whether or not a liquid is shear banding is described in the Examples.

Without wishing to be bound by theory we believe the improvement in glucose control provided by the such compositions which exhibit shear banding may be due to the formation of a relatively stationary layer near the walls of the gastrointestinal tract provided by compositions which exhibit shear banding resulting in a slower passage of carbohydrate through the wall of the intestine than would otherwise be the case for corresponding liquid that does not exhibit shear banding or does so to a significantly lesser extent. Furthermore, the lodgement of soluble or dispersible protein in the relatively stationary layer provides a controlled and slower and more prolonged presentation of protein to the digestive enzymes. This means that the effect of protein in stimulating insulin release is prolonged.

We have found this significant improvement in control of post-prandial glucose to be peculiar to subjects suffering IGT or diabetes and the benefits are particularly evident with diabetic subjects such as subjects who require drug management of diabetes and in particular combination therapy. Such subjects have a slow insulin response relative to healthy subjects, and can benefit more from (a) the slower glucose uptake kinetics caused by shear banding liquids, and (b) the more prolonged presentation of proteins to digestive enzymes in the upper part of the small intestine in these shear banding liquids.

Shear banding is a feature of flow that is intrinsic to the material, and can be used to characterise liquids and soft (deformable) solid materials. Such characterisation activities are best carried out in well-controlled driven-flow conditions (see testing protocol in the Examples below). Use of the test protocol readily allows determination of the effect of specific components on shear banding. The composition of the invention will comprise water dispersible powder comprising at least one water soluble or water dispersible compound selected from the amino acids, peptides and proteins in an amount of at least 8 g (preferably at least 10 g, more preferably at least 15 g and still more preferably in the range of from 15 g to 25 g) total of said water soluble and contains water dispersible compound on a dry weight basis per serving of drink. Preferably the composition also comprises galactomannan gum and the proportions of components and the contribution of specific variations in types of protein and galactomannan gum and the use and amounts of additional components may be readily determined by the shear banding test as set out in the examples hereto. Some components such as inulin (a soluble fibre) may be used in suitable amounts but may disrupt shear banding performance in too great proportion.

In a particularly preferred embodiment, the drink composition comprises:
water soluble or water dispersible protein in an amount of at least 8 g total on a dry weight basis per serving of drink;

aqueous liquid in an amount of from 70 ml to 400 ml per serving, and wherein the drink exhibits shear banding when subject to the shear banding test herein described.

In the presence of thickeners, fibre or the like the composition may gradually increase in viscosity if formed by mixing a dry powder composition with water. In such embodiments the determination of the presence of shear banding is determined at 10 minutes after the commencement of vigorous mixing of the dry composition with water.

The amount of water soluble or water dispersible compound selected from the group of amino acids, peptides and protein (preferably protein) is at least 8 g per serving on a dry weight basis. The preferred amount is at least 15 g total on a dry weight basis. The range of 8 g to 40 g is preferred particularly 10 g to 35 g, more preferably 10 g to 25 g and most preferably 15 g to 25 g. In the most preferred embodiments the water soluble or water dispersible compound is a water soluble or water dispersible protein and the water soluble or water dispersible protein is present in an amount in the range of 8 g to 40 g, preferably 10 g to 35 g, more preferably 10 g to 25 g and most preferably 15 g to 25 g on a dry weight basis per serve.

The water soluble or water dispersible compound is preferably protein. The protein may be selected from water soluble and water dispersible protein of plant or animal origin and preferably from the group consisting casein and salts thereof and whey and hydrolysis products of whey. Examples of water soluble or water dispersible protein of vegetable origin include soy protein, and pea protein. Further examples of proteins include milk protein concentrate (MPC). More preferably the protein is selected from dairy whey and derivatives thereof such as hydrolysed dairy whey.

The term "peptide" means a compound that is made up of two or more amino acids joined by covalent bonds which are formed by the elimination of molecules of water from the junction of the amino group of one amino acid and the carboxyl group of the next amino acid. The term peptide is not used to suggest a particular number of amino acids and can contain several hundred amino acids or more. "Peptide" is interchangeable with "polypeptide". Protein may be made up of a single peptide chain or a number of peptide chains joined together. The main difference between a peptide and protein is the level of structure. A protein may have primary, secondary and tertiary levels of structure.

It is preferred that the water soluble or water dispersible compound selected from the group consisting of amino acids, peptides and proteins comprises one or more amino acids selected from the group consisting of lysine, threonine, leucine, isoleucine, argenine and valine.

It has been found by interrogating consumers that the regular consumption of high volumes of liquid prior to a meal can cause gastric discomfort when the meal is eaten. Preferably pre-meal drinks are no more than 300 ml in volume and more preferably no more than 200mls. The proportion of said water soluble or water dispersible compound (preferably protein) based on total solid powder is preferably in the range 40-90% and more preferably 50-80%.

The drink preferably further comprises one or more polysaccharides, particularly galactomannan gums preferably selected from guar gum and derivatives thereof. In one set of embodiments the total polysaccharide (preferably the total galactomannan gum) content is preferably no more than 10 g per serving (such as no more than 8 g per serving or no more than 7 g per serving) and preferably at least 1 g per serving such as at least 2 g per serving or at least 3 g per serving and most preferably in the range of from 4 g to 6 g per serving.

The proportion of gum is preferably in the range 5-30% w/w of the powder, and more preferably in the range 10-20% w/w of the powder.

The drink is particularly suitable for treatment of a subject suffering diabetes or IGT, when the drink is used concomitantly with diabetes medication. Examples of such medication include at least one selected from the group consisting of biguanides (such as metformin), enzyme inhibitors (such as angiotensin converting enzyme inhibitors (ACEI) and alpha-glucosidase inhibitors), Sulfonylureas (such as glyburide, glipizide, glimepiride, tolbutamide, chlorpropamide, acetohaxamide and tolazamide), meglitinides (such as repaglinide), thiazolidinediones (such as troglitazone, pioglitazone and rosiglitazone) and insulin and insulin analogues (such as lispro).

The composition may be used for subjects receiving concommitent therapy with combinations drugs for treatment of a diabetes of IGT. Examples of such combination therapy include combinations of Sufonyl ureas and metformin, repaglinide and metformin, thiazolidinediones and metformin and enzyme inhibitors and metformin.

The drink may be used for administration at least once daily before a meal or before two or three meals daily.

Diabetes medications are frequently taken with a meal, and in one preferment, the drink of the invention is taken a period of time before the consumption of meal and medication.

The drink is preferably used for administration to a subject suffering diabetes or IGT no more than 30 minutes prior to ingestion of a meal, preferably no more than 15 minutes prior to ingestion of a meal. It has been found by interrogating consumers that having a drink 15 minutes or less prior to a meal is significantly more convenient than having a drink 30 minutes prior to a meal. The composition is also particularly effective if consumed within 15 minutes before consumption of a meal.

It is particularly desirable if the drink maintains a high level of efficacy when taken at a range of times before the meal (or the meal/medication event), i.e. if the drink is effective both when taken shortly before a meal and when taken 15 minutes (or even longer) before a meal. This is because in practice patients are likely to use the drink at various times before a meal.

When a shear banding drink containing protein is prepared by mixing a fixed amount of water and a fixed amount of powdered materials, the following problems arise.
1. If too much time is taken in mixing, the drink may be unpalatable because it is too thick.
2. If too little time is taken in mixing the drink may be unpalatable due to clumping of powder ingredients.
3. The homogeneity of the drink may depend on the shape of the vessel in which it is mixed. E.g. vessels with smooth and gently curved edges lead to less clumping when compared to containers with sharp angled corners.
4. The degree of homogeneity of the drink is influenced by the shape of the stirring implement.
5. If the container in which the drink is mixed needs to be re-used for any purpose, delay in cleaning the container may lead to the formation of an adhesive film which can be difficult to remove.
6. It is easy for users to provide a variable amount of water when re-constituting the drink on a regular basis. The concentration of powder in water can strongly influence the shear banding characteristics of the drink.

Most preferably the drink is consumed in the range of from half a minute to 15 minutes before ingestion of a meal. In the case of drink compositions prepared by mixing with an aqueous liquid it may be preferred for the drink to be consumed shortly after mixing. This is particularly the case where the drink undergoes a significant increase in viscosity after mixing due, for example to the presence of fibre or gum components. In this set of embodiments it may be preferred to consume the drink within 5 minutes of mixing, preferably within 3 minutes of mixing and most preferably within two minutes of mixing of the powder and aqueous liquid.

There is also provided a method for moderating the blood glucose levels produced by a meal in a subject suffering diabetes or impaired glucose tolerance, the method comprising:

providing a unit serving of powder for preparation of a drink the powder comprising at least one water soluble or water dispersible compound selected from the group consisting of amino acids, peptides and proteins in a total amount of at least 8 g on a dry weight basis of the powder serving; and mixing the unit serving of powder with aqueous liquid in an amount of from 70 to 400 grams of aqueous liquid per unit serving; and administering the drink prior to ingestion of the meal; wherein the drink exhibits shear banding on a standard rotating cylinder shear banding test as herein described.

The amount of water soluble or water dispersible compound selected from the group of amino acids, peptides and protein (preferably protein) is at least 8 g per serving on a dry weight basis. The preferred amount is at least 15 g total on a dry weight basis. The range of 8 g to 40 g is preferred particularly 10 g to 35 g, more preferably 10 g to 25 g and most preferably 15 g to 25 g. In the most preferred embodiments the water soluble or water dispersible compound is a water soluble or water dispersible protein and the water soluble or water dispersible protein is present in an amount in the range of 8 g to 40 g, preferably 10 g to 35 g, more preferably 10 g to 25 g and most preferably 15 g to 25 g on a dry weight basis per serving.

The preferred protein is generally selected from water soluble or water dispersible protein of plant or animal origin and preferably from the group consisting casein and salts thereof and whey and hydrolysis products of whey. Examples of water soluble or water dispersible protein of plant origin include such protein from soy bean. More preferably the soluble or colloidal protein is selected from dairy whey and derivatives thereof such as hydrolysed dairy whey.

The powder may and preferably will further comprise a polysaccharide, preferably a galactomannan gum such as selected from guar gum and derivatives thereof such as hydrolysed guar gum and more preferably guar gum.

The total galactomannan or polysaccharide gum content of the powder is preferably no more than 10 g per serving (such as no more than 8 g per serving or no more than 7 g per serving) and preferably at least 1 g per serving such as at least 2 g per serving or at least 3 g per serving and most preferably in the range of from 4 g to 6 g per serving.

In order to obtain the optimum result in modifying the post-prandial glucose profile the drink is preferably administered to the subject suffering diabetes or IGT no more than 30 minutes prior to ingestion of a meal, preferably no more than 15 minutes prior to ingestion of a meal and most preferably in the range of from half a minute to 15 minutes before ingestion of a meal.

The powder may be mixed with an aqueous liquid by combining the two and stirring or by shaking (preferably in a closed container). In one set of embodiments the powder is mixed with an aqueous liquid by shaking the powder and liquid together in a container having a closure and preferably having a volume at least 20% more preferably at least 50% greater than the volume of the combined liquid and powder and still more preferably in the range of from 50% to 200% greater than the volume of liquid and powder.

In this set of embodiments the method of forming the composition for consumption by the subject suffering IGT or diabetes preferably comprises adding the powder and liquid to an elongated container, sealing the container with the closure and shaking the container with the longest dimension held sideways and shaken using a side to side movement.

In cases where the drink undergoes a significant increase in viscosity following mixing of the powder and aqueous liquid is generally preferred to administer the composition to the subject suffering diabetes or IGT within 5 minutes of commencement of mixing of the powder and aqueous liquid.

The shear banding test as hereafter described in a preferred embodiment produces a region of rapid flow adjacent a rotating cylinder and an outer torroid region spaced at a distance from the rotating cylinder in which the flow is reduced so as to produce shear banding.

We have found that compositions which provide a certain distance of the shear banding interface from the surface of the driven rotating cylinder (under the conditions of the shear banding test) have particularly efficaceous results in reducing postprandial glucose. Without wishing to be bound by theory, we believe that the positioning of the interface may correlate with the integrity of the static layer adjacent the gut wall which may be beneficial in enhancing the reduction in postprandial glucose.

In the preferred embodiments of the invention, the shear banding tests provides a shear banding interface (determined as hereinafter described) at a distance from the rotating cylinder of 12 mm diameter which is at least 2.5 mm, preferably at least 5 mm and more preferably at least 7 mm, such as at least 10 mm or at least 12 mm. The test is conducted in a dish of 90 mm diameter with a dye drop placed 20 mm from the dish wall. In compositions of the invention the dye drop is in the torroid region in which liquid shear is sufficiently low to produce a shear banding result.

Typically the distance of the interface is no more than 18 mm from the rotating cylinder and more preferably no more than 16 mm from the rotating cylinder. The interface is, in one set of embodiments, in the range of from 2.5 to 18 mm, preferably from 5 mm to 16 mm and more preferably from 7 mm to 16 mm, such as 10 mm to 16 mm or 12 mm to 16 mm.

The method of treatment of subjects suffering IGT or diabetes is particularly suited to such subjects receiving treatment with diabetes medication preferably comprising at least one selected from the group consisting of biguanides (such as metformin), enzyme inhibitors (such as angiotensin converting enzyme inhibitors (ACEI) and alpha-glucosidase inhibitors), Sulfonylureas (such as glyburide, glipizide, glimepiride, tolbutamide, chlorpropamide, acetohaxamide and tolazamide), meglitinides (such as repaglinide), thiazolidinediones (such as troglitazone, pioglitazone and rosiglitazone) and insulin and insulin analogues (such as lispro) and wherein the treatment with diabetes medication is continued concomitently with said drink. Preferably the medication is consumed with the meal, and the drink is taken before the meal/medication event. Where the diabetes medication is metformin, the drink may be taken before the metformin/meal event once or twice per day. If metformin is taken once a day, the drink may be taken before a metformin/meal event wherein the amount of metformin may be in the range 500-1000 mg. If metformin is taken twice a day, the drink may be taken before these 2 metformin/meal events or before one metformin/meal events wherein the amount of metformin may be in the range 500-1000 mg.

In a preferred set of embodiments the subject suffering diabetes or IGT concomitantly receives treatment with diabetes combination drug therapy (such as combinations of Sufonyl ureas and metformin, repaglinide and metformin, thiazolidinediones and metformin and enzyme inhibitors and metformin).

It has been found the drinks of the invention are particularly effective in reducing the post-prandial blood glucose profile if the meal comprises gluten or a gluten containing carbohydrate. Examples of gluten containing materials include products made from wheat flour such as bread, pizza, cakes, biscuits, cereals and pastries. The drinks of the invention are even more effective if the meal substantially comprises one or more of bread, toast, sandwiches and cereals In one set of embodiments there is provided a kit for providing a serving of a drink for moderating blood glucose levels following a meal in a human subject suffering diabetes or impaired glucose tolerance (IGT) the kit comprising:
  at least one serving of water soluble or water dispersible material selected from the group consisting of amino acids, peptides and proteins in a total amount of at least 8 g on a dry weight basis per serving of drink;
  a container having a level indicating a liquid volume of from 70 ml to 400 ml;
  a closure for the container; and
  a space within the container above the level to allow vigorous mixing prior to consumption wherein the mixing of the powder with water filled to the level provides a drink which exhibits shear banding on a standard rotating cylinder shear banding test as herein described.

The amount of water soluble or water dispersible compound selected from the group of amino acids, peptides and protein (preferably protein) is at least 8 g per serving on a dry weight basis. The preferred amount is at least 15 g total on a dry weight basis. The range of 8 g to 40 g is preferred particularly 10 g to 35 g, more preferably 10 g to 25 g and most preferably 15 g to 25 g. In the most preferred embodiments the water soluble or water dispersible compound is a water soluble or water dispersible protein and the water soluble or water dispersible protein is present in an amount in the range of 8 g to 40 g, preferably 10 g to 35 g, more preferably 10 g to 25 g and most preferably 15 g to 25 g on a dry weight basis per serving.

The preferred protein may be selected from water soluble or water dispersible protein of plant or animal origin and preferably from the group consisting casein and salts thereof and whey and hydrolysis products of whey, more preferably selected from dairy whey and derivatives thereof such as hydrolysed dairy whey.

In one set of embodiments the powder further comprises a polysaccharide such as a galactomannan gum such as selected from guar gum and derivatives thereof. The total galactomannan gum content is in one set of embodiments no more than 10 g per serving (such as no more than 8 g per serving or no more than 7 g per serving) and preferably at least 1 g per serving such as at least 2 g per serving or at least 3 g per serving and most preferably in the range of from 4 g to 6 g per serving.

The container may have a volume at least 20% (preferably at least 50%) greater than the volume of the liquid and powder and preferably in the range of from 50% to 200% greater than the combined volume of liquid and powder.

In one set of embodiments there is provided use of a water dispersible dry powder comprising at least one water soluble or water dispersible compound selected from the group consisting of amino acids, peptides and proteins and aqueous liquid in manufacture of a drink composition for management of diabetes or Impaired Glucose Tolerance wherein the use comprises mixing a serving of the dry powder comprising at least one water soluble or water dispersible compound in a total amount of at least 8 g on a dry weight basis per serving of drink with aqueous liquid in an amount of from 70 to 400 g per serving, wherein the drink mixture exhibits shear banding on a standard rotating cylinder shear banding test as herein described.

The amount of water soluble or water dispersible compound selected from the group of amino acids, peptides and protein (preferably protein) is at least 8 g per serving on a dry weight basis. The preferred amount is at least 15 g total on a dry weight basis. The range of 8 g to 40 g is preferred particularly 10 g to 35 g, more preferably 10 g to 25 g and most preferably 15 g to 25 g. In the most preferred embodiments the water soluble or water dispersible compound is a water soluble or water dispersible protein and the water soluble or water dispersible protein is present in an amount in the range of 8 g to 40 g, preferably 10 g to 35 g, more preferably 10 g to 25 g and most preferably 15 g to 25 g on a dry weight basis per serving.

The protein is generally selected from soluble and colloidal protein of plant or animal origin and preferably from the group consisting casein and salts thereof and whey and hydrolysis products of whey. Examples of soluble or colloidal protein of plant origin include such protein from soy bean. More preferably the soluble or colloidal protein is selected from dairy whey and derivatives thereof such as hydrolysed dairy whey.

The powder may and preferably will further comprise a polysaccharide, particularly galactomannan gum such as selected from guar gum and derivatives thereof.

The total polysaccharide, particularly galactomannan gum, content of the powder is preferably no more than 10 g per serving (such as no more than 8 g per serving or no more than 7 g per serving) and preferably at least 1 g per serving such as at least 2 g per serving or at least 3 g per serving and most preferably in the range of from 4 g to 6 g per serving.

In order to obtain the optimum result in modifying the post-prandial glucose profile the drink is preferably administered to the subject suffering diabetes or IGT no more than 30 minutes prior to ingestion of a meal, preferably no more than 15 minutes prior to ingestion of a meal and most preferably in the range of from half a minute to 15 minutes before ingestion of a meal.

The powder may be mixed with an aqueous liquid by combining the two and stirring or by shaking (preferably in a closed container). In one set of embodiments the powder is mixed with an aqueous liquid by shaking the powder and liquid together in a container having a closure and preferably having a volume at least 50% greater than the volume of the combined liquid and powder and preferably in the range of from 50% to 200% greater than the volume of liquid and powder.

In this set of embodiments the method of forming the composition for consumption by the subject suffering IGT or diabetes preferably comprises adding the powder and liquid to an elongated container, sealing the container with the closure and shaking the container with the longest dimension held sideways and shaken using a side to side movement.

In cases where the drink undergoes a significant increase in viscosity following mixing of the powder and aqueous liquid is generally preferred to administer the composition to the subject suffering diabetes or IGT within 5 Minutes of commencement of mixing of the powder and aqueous liquid.

The method of treatment of subjects suffering IGT or diabetes is particularly suited to such subjects receiving treatment with diabetes medication preferably comprising at least one selected from the group consisting of biguanides (such as metformin), enzyme inhibitors (such as angiotensin converting enzyme inhibitors (ACEI) and alpha-glucosidase inhibitors), Sulfonylureas (such as glyburide, glipizide, glimepiride, tolbutamide, chlorpropamide, acetohaxamide and tolazamide), meglitinides (such as repaglinide), thiazolidinediones (such as troglitazone, pioglitazone and rosiglitazone) and insulin and insulin analogues (such as lispro) and wherein the treatment with diabetes medication is continued concomitently with said drink.

In a preferred set of embodiments the subject suffering diabetes or IGT concomitantly receives treatment with diabetes combination drug therapy (such as combinations of Sufonyl ureas and metformin, repaglinide and metformin, thiazolidinediones and metformin and enzyme inhibitors and metformin).

The drink and powder preferably have a low calorie value, such as less than about 25 g protein calorie equivalent.

In a preferred set of embodiments the drink is prepared by combination of a powder comprising the protein and optionally other components such as the gum. The drink may be prepared by adding the aqueous liquid to powder in a container or alternatively aqueous liquid (preferably low calorie aqueous material) can be added to powder to make the drink.

The aqueous liquid may be an aqueous beverage such as fruit juice, milk, soup or broth or the like. The most preferred aqueous liquid is water although it will be understood that alternative aqueous liquids may be used without detracting from the ability to provide shear banding with an appropriately formulated powder by making any allowances necessary for the components present in the aqueous liquid such as protein or thickeners which may contribute to formation of a shear banding mixture.

In one preference the aqueous liquid is water, added to a container prior to the addition of the powdered materials (i.e. powdered material is added to water rather than vice-versa).

In another preference the powdered material is provided inside a container provided with a closure. The container may be disposable, transparent or partially transparent container. The container may have a level indicator to act as a guide for the amount of water that needs to be added. This method of forming the drink is referred to as the "shake and take method".

In another preference the shake and take bottle is elongated. It may have a circular or square or other shaped cross section. In one set of embodiments the vertical dimension of the bottle is significantly greater than the width of the bottle (i.e. the bottle is an elongated bottle). In another preference the cross section of the elongated bottle enables close and efficient packing of multiple bottles in a bottle pack.

In another preference, the profile of the bottle (with the closure on the top) is such that the walls of the bottle are tapered so that the width of the bottle near the closure is greater than the width of the bottle near the base.

In another preference a plurality of disposable containers are presented and at least two distinct flavours are included—this is to prevent a regular consumer becoming bored with the taste.

Preferably the volume of the shake and take bottle is at least 200 ml and preferably at least 250 ml. The volume may be significantly greater than 250 ml.

It is preferred that the walls of the bottle do not create a groove or valley in the region where they connect with the base of the bottle—this is because powder may become lodged in said groove or valley and dissolution of the powder in the drink may be inhibited. The bottle preferably has a flat base. Preferably the base and side wall are joined by a gradually curved portion which avoids retention of deposited powder and facilitates resuspension of deposited powder into the bulk of the drink.

It is also preferred that the bottle containing dry drink powder material should be shaken before addition of the drink liquid, so that powder packing and powder bridging is minimised. For elongated bottles it is preferred that after the aqueous liquid is added to the bottle and that after the closure is fastened, the bottle is oriented so that the long axis is horizontal and the shaking action which is used to homogenise the contents of the bottle is a side to shaking motion along the horizontal axis. It has been found that the homogeneity of the drink formed using the above method, is significantly better than if the long axis of the bottle is vertical and the shaking motion is up and down.

It has also been found that the reproducibility of the post-prandial blood glucose profile obtained with the drink of the invention is significantly improved using the shake and take method (relative to reconstitution in a container supplied by the consumer). The reproducibility of the post-prandial blood glucose profile is even better when an elongated bottle is held in a horizontal orientation with side-to-side shaking.

When a shear banding drink is made, for example combing whey protein concentrate with guar gum powder, the use of a very fine guar gum powder (i.e. less than 30 microns) and a fine whey protein concentrate powder (i.e. less than 100 microns) leads to a relatively rapid development of a high viscosity in the drink. Some consumers find such high viscosity drinks unpalatable. It is preferred that the drink is formulated so that the viscosity increase occurs over a longer period of time e.g. 3 minutes rather than 1 minute. One of the ways this can be achieved is to provide the guar in the form of a coarser granule.

In a particularly preferred embodiment of the invention the powder portion of the drink consists of:
dispersed protein selected from water soluble and water dispersible protein in an amount of from 15 g to 30 g total of soluble and colloidal protein on a dry weight basis per serving of drink; and
guar gum in an amount of from 3.5 g to 6 g per serving; optionally at least one of flavouring and colouring.

The aqueous liquid used in formulating the drink preferably consists of water in an amount of from 100 to 250 ml per serving, and preferably 125-175 ml per serving.

Examples of further functional material which may be used in the composition include:
Chlorogenic acid, proposed to be responsible for the reduction in diabetes risk associated with heavy coffee intake.

Glucose uptake inhibitors, which slow the absorption of glucose and include viscosifying agents such as vegetable fibre. Specific examples include glucomannam, psyllium husk fibre, and guar gum.

Peptide analogues, such as incretin mimetics, glucagon-like analogues and agonists, amylin analogues. The main incretins are glucagon-like peptide-1 (GLP-1) and gastric inhibitory peptide (glucose-dependent insulinotropic peptide), designated GIP. GLP agonists include Exenatide, Liraglutide and Taspoglutide (not food grade). A common side effect (possibly associated with decreased gastric motility) is nausea.

Protein hydrolysate, optionally with supplementation of leucine (US patent application 20090305945).

Alternative medicine and nutritional materials (not discussed above). These include:

Myrcia root extracts, commercialised as pedra hume de kaa.

Garlic, and particularly deodorised or odour-free garlic

Cinnamon (*Cassia*), and cinnamon bark extract

Curcurmin/turmeric

Magnesium. Recent testing has shown that magnesium (as magnesium chloride) shows promise for TYPE 2 DIABETES. Measurement of blood magnesium can establish the bioavalability of magnesium. Epedmiological studies show that high daily magnesium intake is predictive of lower TYPE 2 DIABETES in men and women.

Zinc

Coriander

Eucalyptus

Juniper

Biotin

Mulberry including mulberry leaf extract

Dark chocolate (rich in flavonols)

Flavanols, a class of class of polyphenolic antioxidant that includes epichatechin.

Caiapo, which is derived from the skin of a variety of white sweet potato (*Ipomoea batas*). It is commercially available throughout Japan without prescription for treating type 2 diabetes. Several studies have been done, some concluding that HbA1c reductions are comparable with Acarbose.

Fenugreek (including Fenugreek extract, fibre, seed and mucilage) which contains 4-hydroxyisoleucine (believed to be the principal bioactive compound, and has been found to exhibit insulinotrpic activity). Several studies (2 g per day) have been done in diabetic cohorts, with evidence of efficacy.

Bitter melon (*Mormordica charantia*), also known as karela and bitter gourd, wild cucumber, ampalaya and cundeamor. Glucose lowering has been documented in animal models of diabetes, and antidiabetic components include charantin and vicine. Several modes of action have been proposed, including inhibition of glucose absorption in the gut, stimulation of insulin secretion, and the stimulation of hepatic glycogen synthesis.

Gurmar (*Gymnema sylvestre*). Small studies imply efficacy in type 1 diabetes and type 2 diabetes.

Prickly pear cactus (Opuntia, Nopal). Mainly reported in Spanish literature. Reported improved glycemic control (lower serum glucose) and improved insulin sensitivity (decreased serum insulin) following a single dose (500 g broiled or grilled nopal stems) in patients with type 2 diabetes. No effect in healthy individuals.

Coccinia indica. Double blind, placebo-controlled trial showed significant improvement in glucose tolerance.

Ginseng Panax). One study shows 200 mg dose decreases HbA1c by 0.5%.

Aloe vera. Tests show reduced fasting glucose in type 2 diabetes patients both in the presence and absence of concomitant sulfonylurea therapy.

Traditional Chinese Medecine has identified type 1 diabetes as "wasting and thirsting syndrome" and type 2 diabetes as "sugar urine illness". There are established treatments within TCD.

Lipoic acid (LA) also known as alpha lipoic acid (ALA),

L-Arginine, which has been classified as a "semi-essential amino acid". L-Arginine serves as a direct precursor for the biosynthesis of NO (L-Arginine is acted on by the enzyme nitric oxide synthase). The evidence appears to be positive for a role in human cardiovascular health.

Vitamin D

Coenzyme Q10. A study on patients with heart disease showed reduced plasma glucose, insulin and lipid peroxides (the latter a marker of oxidative stress). Statins (HMG-CoA reductase inhibitors, taken by many type 2 diabetes patients) can reduce serum coenzyme Q10 by up to 40%.

Polyclonal antibodies—see next section.

Polyclonal Antibodies

Yaron Ilan et al (WO 2009113065, filed 2008) "Immunomodulating compositions for the treatment of immune-mediated disorders" describe an anti-insulin antibody for use in an oral therapy to manage symptoms of type 2 diabetes. The antibody is made from bovine colostrum.

Yaron et al. (WO 2010125565, filed 2009) "Anti-LPS enriched immunoglobulin preparation for use in treatment and/or prophylaxis of a pathologic disorder" describe the use of anti-LPS antibodies for use in an oral therapy to treat disorders associated with liver disease (this includes metabolic syndrome and type 2 diabetes).

Ching-San Lai (U.S. Pat. No. 5,747,532, filed 1995) "Combinational therapeutic methods employing nitric oxide scavengers and compositions useful therefore", teaches that the overproduction of nitric oxide (NO) is associated with a wide variety of disease states that include diabetes as well as septic shock, ischemia, ulcers, inflammatory bowel disease, arthritis, asthma, Alzheimer's disease, Parkinson's disease, multiple sclerosis, cirrhosis, encephalomyelitis, meningitis, pancreatitis, peritonitis, vasculitis, liver inflammation, renal inflammation, shock, chronic fatigue syndrome, burn infection, stroke and cancers. The invention is a method to treat overproduction of NO by using a combination of (a) an agent which inactivates species that induce NO production and (b) an agent (limited to a dithiocarbamate-containing agent) that scavenges NO. A given example of an agent in category (a) is an anti-endotoxin agent such as an antibody to endotoxin. The text of the patent discloses oral administration as a treatment option.

Particularly preferred functional meterials include Vitamin D, magnesium, biotin,cinnamon, caiapo (which is derived from the skin of a variety of white sweet potato (*Ipomoea batas*)) garlic, turmeric/curcurmin and anti-lipopolysaccharide antibody.

The invention will now be described with reference to the following examples. It is to be understood that the examples are provided by way of illustration of the invention and that they are in no way limiting to the scope of the invention.

EXAMPLES

The specification and claims refer to a measure of shear banding. The method for determining shear banding referred to herein will now be discussed with reference to the attached drawings.

BRIEF DESCRIPTION OF THE DRAWINGS

In the drawings:

FIG. 9 is a graph of the post-prandial blood sugar measurements referred to in Example 5 (Control). The subject is subject 1 in Table 1. No pre-meal drink was taken (so that there is no reference to Table 2 and Table 4. The blood test protocol was TP1 in Table 5. This information is consolidated in Table 6.

FIG. 10 is a graph of the post-prandial blood sugar measurements referred to in Example 5 Part 2. The subject is subject 1 in Table 1. The premeal drink powder ingredients are as designated F2 in Table 2, the drink reconstitution protocol is as designated DPP1 in Table 4, and the blood test protocol was as designated TP2 in Table 5.

FIG. 11 is a graph of the post-prandial blood sugar measurements referred to in Example 5 Part 4. The subject is subject 1 in Table 1. The premeal drink powder ingredients are as designated F3 in Table 2, the drink reconstitution protocol is as designated DPP1 in Table 4, and the blood test protocol was as designated TP3 in Table 5.

FIG. 12 is a graph of the post-prandial blood sugar measurements referred to in Example 5 Part 3. The subject is subject 1 in Table 1. The premeal drink powder ingredients are as designated F5 in Table 2, the drink reconstitution protocol is as designated DPP1 in Table 4, and the blood test protocol was as designated TP2 in Table 5.

FIG. 13 is a graph of the post-prandial blood sugar measurements referred to in Example 5 Part 1. The subject is subject 1 in Table 1. The premeal drink powder ingredients are as designated F6 in Table 2, the drink reconstitution protocol is as designated DPP1 in Table 4, and the blood test protocol was as designated TP4 in Table 5.

FIG. 14 is a graph of the post-prandial blood sugar measurements referred to in Example 6 (Control). The subject is subject 2 in Table 1. No pre-meal drink was taken (so that there is no reference to Table 2 and Table 4. The blood test protocol was TP5 in Table 5. This information is consolidated in Table 6.

FIG. 15 is a graph of the post-prandial blood sugar measurements referred to in Example 6 (Part 2). The subject is subject 2 in Table 1. The premeal drink powder ingredients are as designated F9 in Table 2, the drink reconstitution protocol is as designated DPP1 in Table 4, and the blood test protocol was as designated TP2 in Table 5.

FIG. 16 is a graph of the post-prandial blood sugar measurements referred to in Example 6 (Part 1). The subject is subject 2 in Table 1. The premeal drink powder ingredients are as designated F10 in Table 2, the drink reconstitution protocol is as designated DPP1 in Table 4, and the blood test protocol was as designated TP6 in Table 5.

FIG. 17 is a graph of the post-prandial blood sugar measurements referred to in Example 9 (Control). The subject is subject 2 in Table 1. No pre-meal drink was taken (so that there is no reference to Table 2 and Table 4). The blood test protocol was TP12 in Table 5 (this is a metformin experiment). This information is consolidated in Table 6.

FIG. 18 is a graph of the post-prandial blood sugar measurements referred to in Example 9 (Part 1). The subject is subject 2 in Table 1. The premeal drink powder ingredients are as designated F9 in Table 2, the drink reconstitution protocol is as designated DPP3 in Table 4, and the blood test protocol was as designated TP13 in Table 5 (this is a metformin experiment).

FIG. 19 is a graph of the post-prandial blood sugar measurements referred to in Example 10 (Control). The subject is subject 2 in Table 1. No pre-meal drink was taken (so that there is no reference to Table 2 and Table 4. The blood test protocol was TP16 in Table 5 (this is an acarbose experiment). This information is consolidated in Table 6.

FIG. 20 is a graph of the post-prandial blood sugar measurements referred to in Example 10 (Part 1). The subject is subject 2 in Table 1. The premeal drink powder ingredients are as designated F9 in Table 2, the drink reconstitution protocol is as designated DPP3 in Table 4, and the blood test protocol was as designated TP20 in Table 5 (this is an acarbose experiment).

FIG. 21 is a graph of the post-prandial blood sugar measurements referred to in Example 10 (Part 2). The subject is subject 2 in Table 1. The premeal drink powder ingredients are as designated F9 in Table 2, the drink reconstitution protocol is as designated DPP3 in Table 4, and the blood test protocol was as designated TP19 in Table 5 (this is an acarbose experiment FIG. 22 is a graph of the post-prandial blood sugar measurements referred to in Example 11 (Control). The subject is subject 2 in Table 1. No pre-meal drink was taken (so that there is no reference to Table 2 and Table 4. The blood test protocol was TP24 in Table 5 (This is a Glicalazide experiment). This information is consolidated in Table 6.

FIG. 23 is a graph of the post-prandial blood sugar measurements referred to in Example 11. The subject is subject 2 in Table 1. The pre-meal drink powder ingredients are as designated F9 in Table 2, the drink reconstitution protocol is as designated DPP3 in Table 4, and the blood test protocol was as designated TP23 in Table 5 (this is a Glicalazide experiment).

FIG. 24 is a graph of the post-prandial blood sugar measurements referred to in Comparative Example 11 (Part 6/Control). The subject is subject 3 in Table 1. No pre-meal drink was taken (so that there is no reference to Table 2 and Table 4. The blood test protocol was TP1 in Table 5. This information is consolidated in Table 6.

FIG. 25 is a graph of the post-prandial blood sugar measurements referred to in Comparative Example 11 (Part 7). The subject is subject 3 in Table 1. The pre-meal drink powder ingredients are as designated F2 in Table 2, the drink reconstitution protocol is as designated DPP1 in Table 4, and the blood test protocol was as designated TP2 in Table 5.

FIG. 26 is a graph of the post-prandial blood sugar measurements referred to in Comparative Example 11 (Part 8). The subject is subject 3 in Table 1. The pre-meal drink powder ingredients are as designated F6 in Table 2, the drink reconstitution protocol is as designated DPP1 in Table 4, and the blood test protocol was as designated TP4 in Table 5.

FIG. 27 is a graph of the post-prandial blood sugar measurements referred to in Comparative Example 11 (control) The subject is subject 4 in Table 1. No pre-meal drink was taken (so that there is no reference to Table 2 and Table 4. The blood test protocol was TP25 in Table 5. This information is consolidated in Table 6.

FIG. 28 is a graph of the post-prandial blood sugar measurements referred to in Comparative Example 11 (Part 2). The subject is subject 4 in Table 1. The pre-meal drink powder ingredients are as designated F2 in Table 2, the drink reconstitution protocol is as designated DPP1 in Table 4, and the blood test protocol was as designated TP26 in Table 5.

FIG. 29 is a graph of the post-prandial blood sugar measurements referred to in Comparative Example 11 (Part 3). The subject is subject 4 in Table 1. The pre-meal drink powder ingredients are as designated F6 in Table 2, the drink reconstitution protocol is as designated DPP1 in Table 4, and the blood test protocol was as designated TP27 in Table 5.

FIG. 30 is a graph of the post-prandial blood sugar measurements referred to in Comparative Example 11 (Part 4). The subject is subject 4 in Table 1. The pre-meal drink powder ingredients are as designated F9 in Table 2, the drink reconstitution protocol is as designated DPP1 in Table 4, and the blood test protocol was as designated TP28 in Table 5.

FIG. 31 is a graph of the post-prandial blood sugar measurements referred to in Comparative Example 11 (Part 5). The subject is subject 4 in Table 1. The pre-meal drink powder ingredients are as designated F10 in Table 2, the drink reconstitution protocol is as designated DPP1 in Table 4, and the blood test protocol was as designated TP29 in Table 5.

FIG. 32 is a graph of the post-prandial blood sugar measurements referred to in Example 7 (Control). The subject is subject 5 in Table 1. No pre-meal drink was taken (so that there is no reference to Table 2 and Table 4. The blood test protocol was TP30 in Table 5. This information is consolidated in Table 6.

FIG. 33 is a graph of the post-prandial blood sugar measurements referred to in Example 7 (Part 1). The subject is subject 5 in Table 1. The pre-meal drink powder ingredients are as designated F9 in Table 2, the drink reconstitution protocol is as designated DPP3 in Table 4, and the blood test protocol was as designated TP31 in Table 5.

FIG. 34 is a graph of the post-prandial blood sugar measurements referred to in Example 7 (Part 2). (Control). The subject is subject 5 in Table 1. No pre-meal drink was taken (so that there is no reference to Table 2 and Table 4. The blood test protocol was TP32 in Table 5. This is a multi-medication experiment. This information is consolidated in Table 6.

FIG. 35 is a graph of the post-prandial blood sugar measurements referred to in Example 7 (Part 3). The subject is subject 5 in Table 1. The pre-meal drink powder ingredients are as designated F9 in Table 2, the drink reconstitution protocol is as designated DPP3 in Table 4, and the blood test protocol was as designated TP33 in Table 5. This is a multi-medication experiment.

FIG. 36 is a graph of the post-prandial blood sugar measurements referred to in Example 8 (Control). The subject is subject 6 in Table 1. No pre-meal drink was taken (so that there is no reference to Table 2 and Table 4. The blood test protocol was TP34 in Table 5. This is a type 1 diabetes experiment. This information is consolidated in Table 6.

FIG. 37 is a graph of the post-prandial blood sugar measurements referred to in Example 8 (Part 1). The subject is subject 6 in Table 1. The pre-meal drink powder ingredients are as designated F9 in Table 2, the drink reconstitution protocol is as designated DPP3 in Table 4, and the blood test protocol was as designated TP35 in Table 5. This is a type 1 diabetes experiment.

FIG. 38 is a graph of the post-prandial blood sugar measurements referred to in Example 8 (Part 2). The subject is subject 6 in Table 1. The pre-meal drink powder ingredients are as designated F9 in Table 2, the drink reconstitution protocol is as designated DPP3 in Table 4, and the blood test protocol was as designated TP35 in Table 5. This is a type 1 diabetes experiment that is a repeat of the experiment of FIG. 37.

Figure 1:
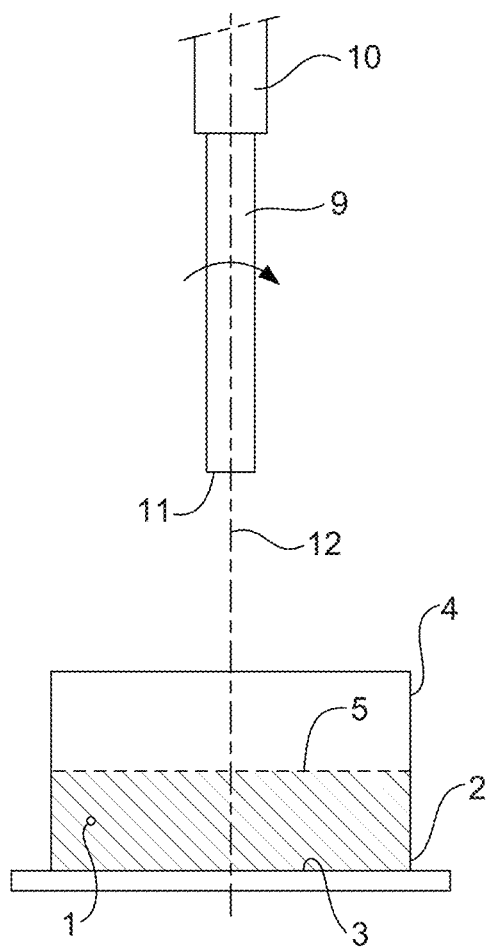
FIG. 1 is a schematic view an apparatus used to measure shear banding in accordance with the invention showing the rotating spindle and liquid sample.
Figure 2:
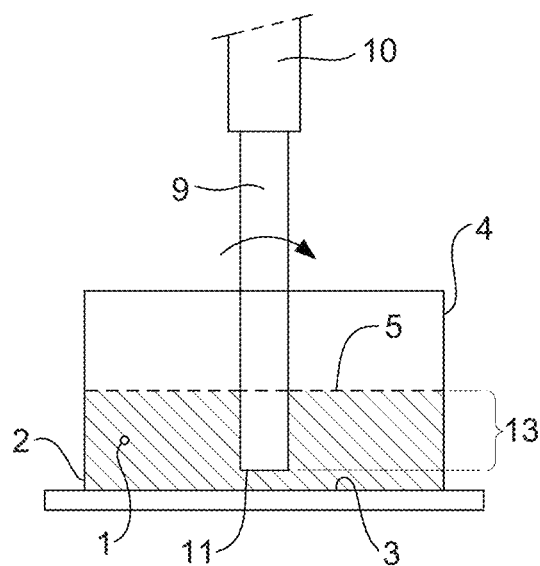
FIG. 2 is a schematic view of the apparatus of FIG. 1 during measurement of shear banding.
Figure 3:
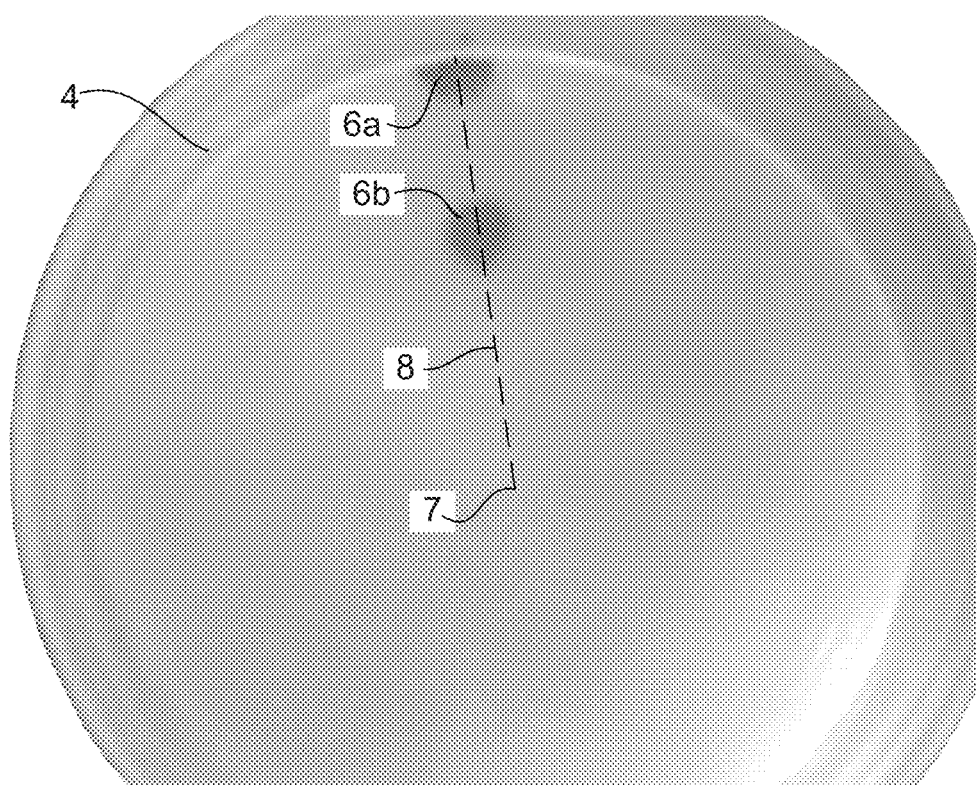
FIG. 3 is a view from above of a liquid sample prior to measurement of shear banding with dye marks placed adjacent the container wall and 20 mm from the container wall.
Figure 4:
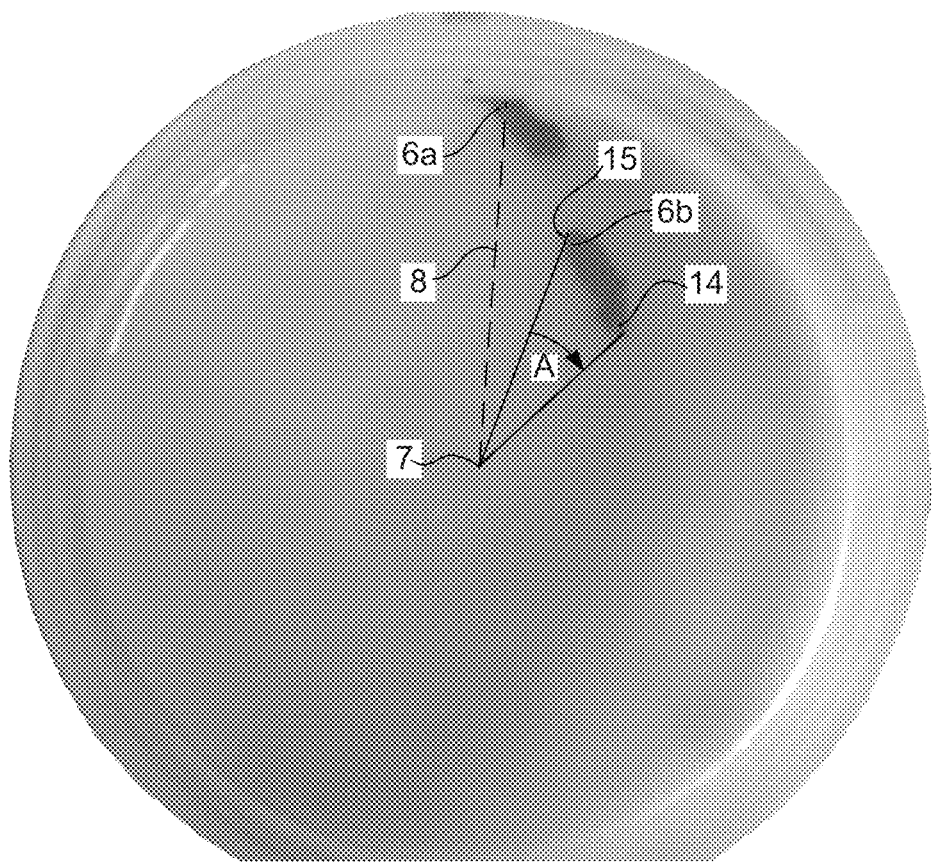
FIG. 4 is a view from above of a drink sample prepared according to Example 1 showing the result of the shear banding test identifying angle "A") (25°) subtended at the centre of the circular container by the front and rear edges of the inner dye drop.
Figure 5:
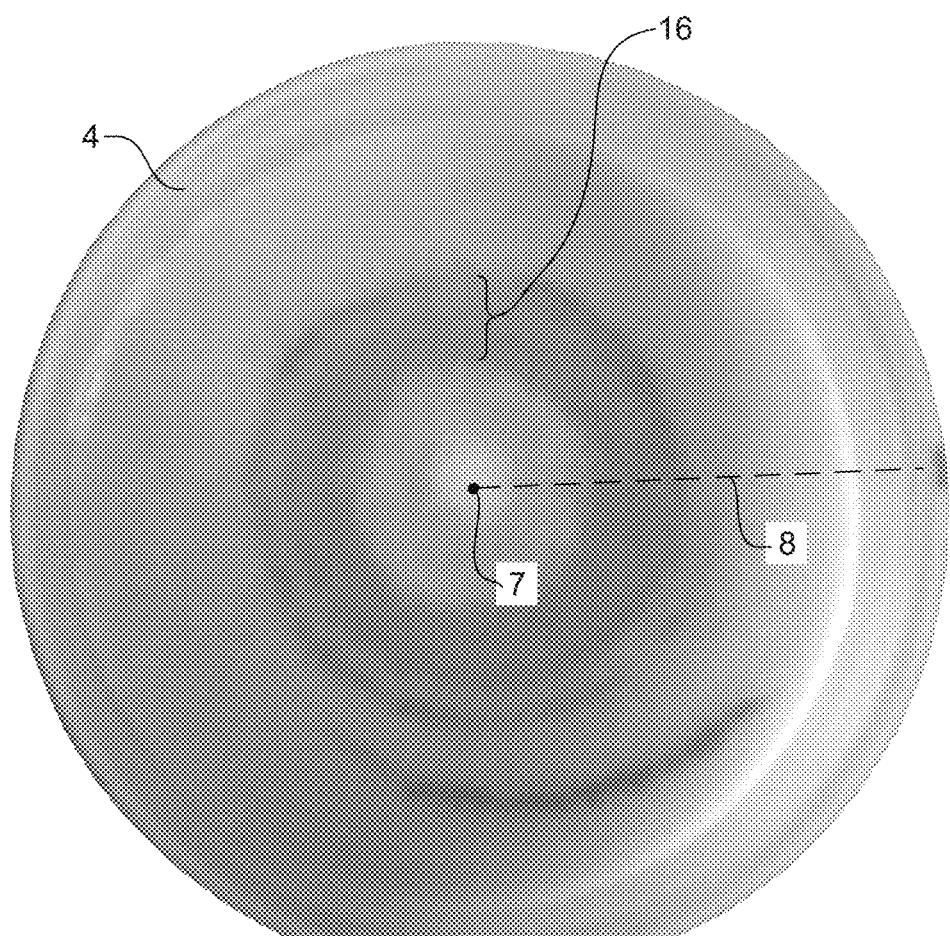
FIG. 5 is a view from above of a drink sample prepared in accordance with Comparative Example 3 showing the result of the shear banding test and the multiple rotations of dye marker.

In the Examples the term "WPC80" or "whey protein concentrate 80" refers to whey protein concentrate having a nominal protein content of 80% w/w of the whey protein content is in the range of from 76% w/w to 81% w/w of the whey protein concentrate.

In the Examples "WP190" or "whey protein isolate 90" refers to whey protein isolate in which the protein concentration is nominally 90% by weight of the whey protein isolate composition. It will be understood that the concentrations may vary slightly such as from 86% to 22% w/w of the composition.

Shear Banding Protocol: Objective Measurement of Shear Banding in a Drink

Referring to FIGS. 1 to 5 and 8 a quantity of test drink (1) containing 150 mls of water (e.g. 175 total drink weight g) is well stirred and poured into a circular flat-bottomed container (2) with a base (3) and cylindrical wall (4). The container has a diameter of 90 mm and a wall (4) height of 50 mm. The height of the surface (5) drink (1) in the container (2) is 25 mm. A drop of water-soluble dye (6a) is placed on the surface of the drink (5) close to the wall of the container (4) and a notional line on the surface of the drink from the centre (7) of the circular container and this mark (6a) is chosen as a reference diameter (8). Another drop of dye (6b) is placed on the reference diameter (8) at a point 20 mm in from the wall (4) of the container. This drop of dye (6b) will be used to define angle A as described below to determine whether shear banding is exhibited by the sample. A smooth wooden cylinder (9) of diameter 12 mm is mounted in a rotatable chuck (10) with the axis of the cylinder (9) vertical, and the flat base of the cylinder (9) is located above the drink surface in such a way that the (vertical) axis (12) of the cylinder (9) is coincident with the (vertical) axis (12) of the circular flat-bottomed container (2). The cylinder(9) is rotated at 850 rpm.

The driven-flow aspect of the measurement is initiated by lowering the rotating cylinder (9) into the drink to a depth (13) of 20 mm below the drink surface (5). After 90 seconds, the rotation of the cylinder (9) is arrested, and the cylinder (9) is slowly withdrawn from the drink.

Quantitative Definition of Shear Banding in Terms of Angle A

After driving the drink (1) in the container (2) by lowering the rotating cylinder (9) for 90 seconds the inner dye droplet (6b) is inspected. The resulting droplet may be highly elongated with a front edge and a trailing edge (see FIG. 5 in which the leading edge of inner dye mark (6b) has become highly elongated extending through multiple revolutions about the centre as is evident from the band width of dye (16). Alternatively the droplet may have relatively minor elongation (so that the angle subtended at the centre of the circular container is small (see FIG. 2). The angle (A) subtended at the centre of the circular container by the front (14) and a rear edge (15) of the drop is designated angle A (see FIG. 4). If angle A is less than 40° then the liquid is considered to exhibit shear banding behaviour. The angle A (see FIG. 4) may be measured by protractor or other suitable angle measurement apparatus. In the case of the drink of the invention of Example 1 (FIG. 4) the angle A is determined to be 25°. In the case of the drink of Comparative Example 3 (not in accordance with the invention) the testing produces a result shown in FIG. 5 in which the reference dye droplet (6b) is elongated through many revolutions.

Protocol for Determination of Shear Banding Interface Distances

The shear banding test provides an annular band region of flow driven by the central rotating cylinder. Compositions of the invention when subject to the above described shear banding test, exhibit distinct band or regions including an inner band or region about the rotating cylinder of relatively high shear and rapid flow and an outer band or torroid region adjacent the wall of the container in which the shear and flow is significantly reduced when compared with the inner high shear rapid flow region adjacent the rotating cylinder. In compositions of the invention the outer band or torroid region of relatively low shear and reduced flow will include the dye drop and produce the shear banding result as hereinbefore defined.

The interface between the two regions can be readily determined by visual inspection while conducting the test and the distance of the interface from the rotating cylinder determined.

The interface between inner band or region of relatively rapid flow and the outer band or torroid region of low shear and reduced flow will be described with reference to FIG. 8.

Figure 8:
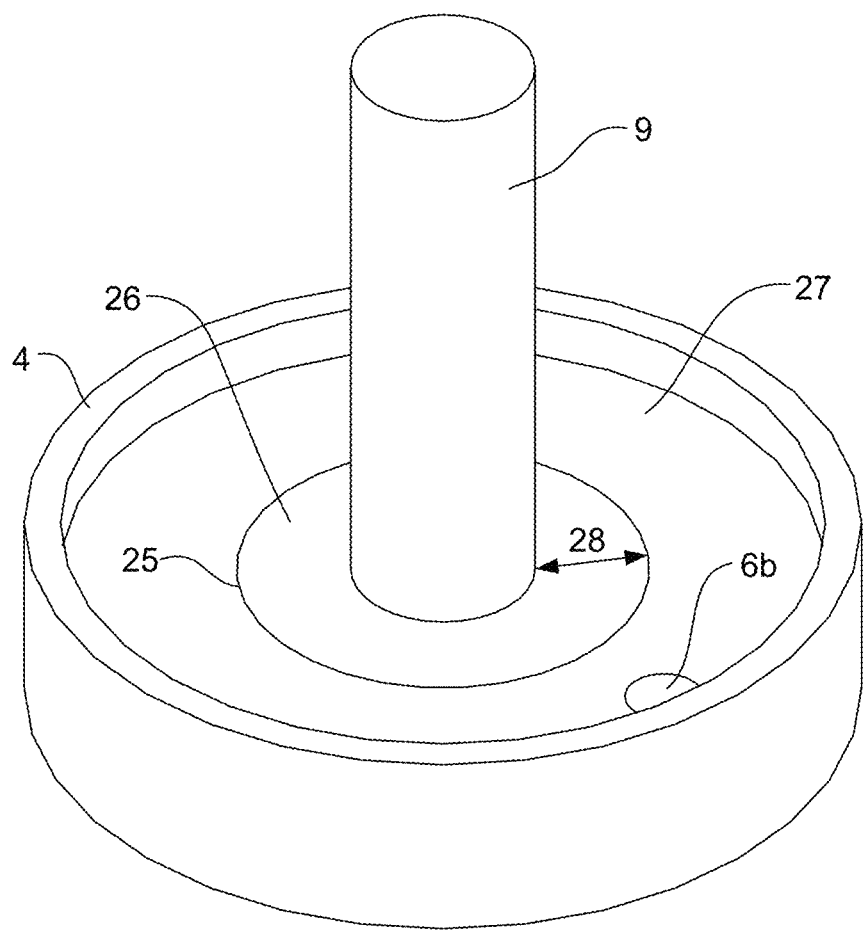
FIG. 8 is a perspective view from above of an apparatus of FIG. 1 during measurement of shear banding showing an inner annular region of high shear relatively rapidly flowing liquid, a torroidal region (outboard of the annular region) in which the shear and flow is significantly reduced and the interface between the two regions.

Referring to FIG. 8 the interface (25) between inner rapid flow region (26) adjacent the rotating cylinder (9) and the outer torroid region (which has a shear flow sufficiently low to produce a shear banding result) is visually evident to the naked eye and the distance (28) of the interface (25) from the rotating cylinder may be measured using a ruler placed adjacent the side of the rotating cylinder (9).

We have found that compositions which are most efficacious in moderating blood glucose levels have an annular interface spaced from the rotating cylinder by at least 2.5 mm, preferably at least 5 mm, more preferably at least 7 mm, such as at least 10 mm or at least 12 mm.

The interface will be at least 10 mm inside of the diameter at which the dye drop is placed (20 mm in from the wall). The interface is preferably no more than 18 mm from the rotating cylinder and more preferably no more than 16 mm. Accordingly, the interface will typically fall in a distance of from 2.5 mm to 18 mm from the rotating cylinder, more preferably 5 mm to 16 mm, still more preferably 7 mm to 16 mm such as 70 mm to 16 mm or from 12 mm to 16 mm.

Shear Banding Testing of Drinks Prepared from Mixing a Powder with Aqueous Liquid Many drinks made from reconstituted drink powder have time-variant flow characteristics. For such drinks, the following standard time sequence should be used to implement the above process. Step 1—reconstitute the drink in 150 mls of water and allow the reconstituted drink to rest for 7 minutes. Step 2—stir the rested drink and pour the drink into the above-described circular flat-bottomed container (2). After 2 minutes apply the dye drops (6a, 6b) described above to the surface (5) of the drink (1), and lower the rotating cylinder (9) into the drink (1).

The above protocol always leads to the formation of a layer of liquid that manifests local shear immediately proximal to the surface of the rotating cylinder.

In many driven drinks the shearing layer grows radially outwards from the surface of the rotating cylinder and extends throughout the liquid (although the tangential velocity of the driven drink will be significantly slower at positions further from the rotating cylinder and closer to the wall of the container). However, in drinks that exhibit shear band formation (i.e. drinks according to the current invention), a locally static layer (adjacent the wall) of significant thickness (e.g. 15-20 mm or even more) develops further out from the cylinder, and this locally static outer layer coexists with the shearing inner layer. The term locally static layer means no shear is exhibited within said layer. The simultaneous existence of an extensive shearing band and an extensive locally static band in a steady-state driven flow scenario is the characteristic feature of shear band formation.

In more general terms, shear band formation occurs in a driven-flow scenario when there is co-existence of (a) an extensive region of drink material that exhibits no local shear, and (b) an extensive region of drink material that exhibits significant local shear.

The above protocol provides a very sensitive test of shear band formation because an extensive shearing/rotating band is always found near the surface of the rotating cylinder, and because the shape of the red dye drop is very sensitive to the existence of local shear. Shear band formation can be detected in the above protocol whenever the liquid dye drop substantially maintains its starting shape (generally circular). In the presence of even small amounts of local shear, the liquid dye drop becomes significantly elongated in response to the local shear. This liquid-drop test for local shear is significantly more sensitive than can be achieved by introducing high-contrast solid particles to the drink (as flow markers)—this is because a solid marker will move according to the resultant of all forces on the solid, and local shear can be inferred only by comparing one particle of solid marker with a separate particle of marker.

Shake-and-Take Process for Consumer Use

Figure 6:
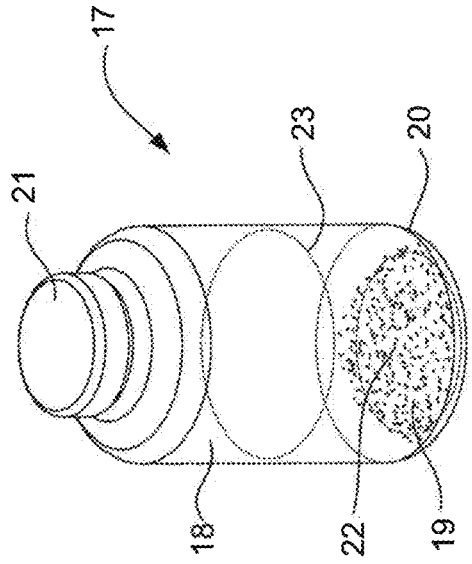
FIG. 6 is a drawing showing a container for preparing a drink of the invention following addition of powder and water.

FIG. 6 shows a container (17) of the type which may be used in preparation of drink composition for consumption by subject. Although the drink may be prepared by mixing in conducting the shear banding test, we have found it to be particularly convenient for untrained consumers of the drink to prepare it by a shake-and-take method such as demonstrated in the protocol of Table 4 protocol TP14.

The shake-and-take method uses a container (17) having a side wall (18) and a flat bottom wall (19) joined to the side wall (18) by a smooth curved transition portion (20) to avoid recesses in which a deposit of powder may be resistant to being suspended in added water.

The container is provided with a closure (21) which is close filling to inhibit leakage of liquid during shaking. The container and closure may have co-operating threaded portions to provide sealing.

The container may be of volume such as 200 ml to 600 ml depending on the volume of drink which is generally no more than half the volume of the bottle.

In the shake-and-take process, a container (17) provided with powder (22) such as containing 15 g to 35 g protein and 2 g to 8 g gallactomannan gum is preferably first shaken to disrupt any settlement or packing during storage and aqueous liquid such as water is added in a volume (23) such as 100 to 250 ml which generally no more than half fills the container (17).

The container closure (21) is sealed on the container and the container is vigorously shaken. It may be shaken vertically, i.e. with the container closure facing up or down and preferably the longest axis of the container generally vertical.

Figure 7:
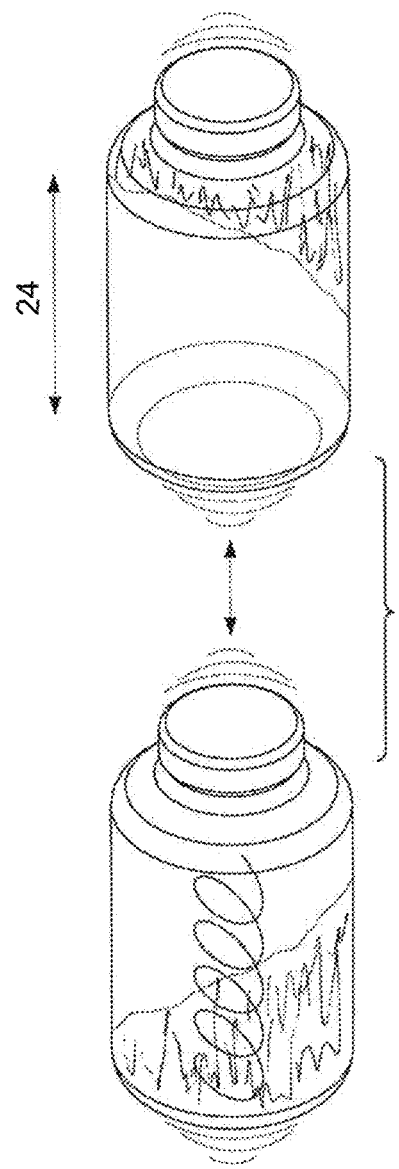
FIG. 7 is a drawing showing the preferred shaking orientation of the container to suspend powder in aqueous liquid within the container.

However, in a further and more preferred embodiment shown in FIG. 7 the container is shaken with the longest dimension (24) of the container disposed sideways and with a side-to-side motion until the powder is well suspended (generally from several seconds to 30 seconds (typically 5 to 20 seconds).

COMPARATIVE EXAMPLES 1 to 10 and EXAMPLES 1 to 4

These Examples examine the variation in sheer banding test results for protein powders of different composition when vigorously mixed with water and prepared according to Step 1 and Step 2 and subsequently measuring angle A using the sheer banding test described above.

COMPARATIVE EXAMPLE 1

When a drink comprising of 3.3% w/v guar gum (this corresponds to 5 grams guar gum in 150 ml of water) is tested for shear banding, Angle A is found to be less than 40°, the drink exhibits shear banding behaviour when measured 7 minutes after vigorous mixing. However this drink is not a drink according to the invention because it does not contain at least 10 g of protein per individual serve.

COMPARATIVE EXAMPLE 2

When a drink comprising of 3.3% w/v psyllium husk powder (this corresponds to 5 grams psyllium husk powder in 150 ml of water) is tested for shear banding, Angle A is found to be greater than 360°, the drink does not exhibit shear banding behaviour when measured 7 minutes after vigorous mixing. This is not a drink according to the invention. It is important to note that both psyllium husk powder and guar gum are both common gel forming fibres in the food industry.

EXAMPLE 1

When a drink comprising of 20 g of whey protein concentrate (WPC80) and 5 g guar gum powder and 150 ml water is tested for shear banding, Angle A is found to be approximately 25°, this is significantly less than 40°. The drink exhibits shear banding behaviour. This is a drink according to the invention (see Tables 2 and 3).

EXAMPLE 2

When a drink comprising 10 g of whey protein concentrate (WPC80) and 5 g guar gum powder and 150 ml water is tested for shear banding, Angle A is found to be approximately 13°, this is significantly less than 40°. The drink exhibits shear banding behaviour. This is a drink according to the invention (see Tables 2 and 3).

COMPARATIVE EXAMPLE 3

When a drink comprising 20 g of whey protein concentrate (WPC80) and 5 g psyllium husk powder to 150 ml water is tested for shear banding, Angle A is found to be 339°, this is significantly higher than 40°. The drink does not exhibit shear banding/quasi-shear banding behaviour. This is not a drink according to the invention. It is important to note that both psyllium husk powder and guar gum are both common gel forming fibres in the food industry (see Tables 2 and 3).

COMPARATIVE EXAMPLE 4

When a comprising 10 g of whey protein concentrate (WPC80) and 5 g psyllium husk powder to 150 ml water is tested for shear banding, Angle A is found to be greater than 360°, the drink does not exhibit shear banding/quasi-shear banding behaviour. This is not a drink according to the invention. It is important to note that both psyllium husk powder and guar gum are both common gel forming fibres in the food industry (see Tables 2 and 3).

COMPARATIVE EXAMPLE 5

When a drink comprising 20 g of whey protein concentrate (WPC80), 2.5 g psyllium husk powder and 2.5 g guar gum powder to 150 ml water is tested for shear banding, Angle A is found to be greater than 360°, the drink does not exhibit shear banding/quasi-shear banding behaviour. This is not a drink according to the invention. The shear banding characteristics of a complex drink formulation cannot be predicted from the individual ingredients.

COMPARATIVE EXAMPLE 6

When a drink comprising 20 g of whey protein concentrate (WPC80), 5 g guar gum powder and 5 g Fibrulose 97 (Company-Cosucra: Soluble Chicory Fibre) to 150 ml water is tested for shear banding, Angle A is found to be approximately 90°, this is significantly more than 40°. The drink does not exhibit shear banding/quasi-shear banding behaviour. When this result is compared with a drink comprising 20 g WPC80 and 5 g guar it is apparent that the further addition of Fibrulose 97 fibre leads to the loss of shear banding behaviour. The shear banding characteristics of a complex drink formulation cannot be predicted from individual ingredients.

COMPARATIVE EXAMPLE 8

When a drink comprising 10 g of whey protein concentrate (WPC80) to 150 ml water is tested for shear banding, Angle A is found to be greater than 360°, the drink does not exhibit shear banding behaviour when measured 7 minutes after vigorous mixing. This is not a drink according to the invention (see Tables 2 and 3).

COMPARATIVE EXAMPLE 9

When a drink made comprising 20 g of whey protein concentrate (WPC80) to 150 ml water is tested for shear banding, Angle A is found to be greater than 360°, the drink does not exhibit shear banding behaviour when measured 7 minutes after vigorous mixing. This is not a drink according to the invention.

COMPARATIVE EXAMPLE 10

When a drink comprising 20 g of whey protein concentrate (WPC80) and 2.5 g guar gum powder to 150 ml water is tested for shear banding, Angle A is found to be greater than 360°, the drink does not exhibit shear banding behaviour when measured 7 minutes after vigorous mixing. This is not a drink according to the invention.

EXAMPLE 4

When a drink comprising 20 g of whey protein concentrate (WPC80) and 3.5 g guar gum powder to 150 ml water is tested for shear banding, Angle A is found to be less than 40°, the drink does exhibit shear banding behaviour. This is a drink according to the invention.

USE EXAMPLES

The following demonstrate the use of drink compositions of the invention and relevant comparisons in different human subjects.

TABLE 1

Describes the human subjects used in drink trials. Includes subjects with pre-diabetes (IGT), type 2diabetes, Type 1diabetes and healthy (non-diabetic subjects).

| | |
|---|---|
| Subject 1 | Health Status - Pre-diabetic (managed by diet and exercise): Age - 59: Sex - Male: Ethnicity: Caucasian |
| Subject 2 | Health Status - Pre-diabetic (managed by diet and exercise): Age - 57: Sex - Male: Ethnicity: Caucasian |
| Subject 3 | Health Status - Non-Diabetic: Age - 57: Sex - Female: Ethnicity - Caucasian |
| Subject 4 | Health Status - Non-Diabetic: Age - 26: Sex-Male: Ethnicity - Asian/Caucasian |
| Subject 5 | Health Status - Type 2 Diabetic (managed by multitherapy): Age - 62: Sex - Female: Ethnicity - Caucasian |
| Subject 6 | Health Status - Type 1 Diabetic (managed by insulin injections): Age - 50: Sex - Male: Ethnicity - Caucasian |
| Subject 7 | Health Status - Pre-diabetic (managed by diet and exercise): Age - 60: Sex - Male: Ethnicity: Caucasian |

EXAMPLE 5

(Control) Shear banding protein drink is effective in lowering post-prandial blood sugar (pre-diabetic).

Figure 9:
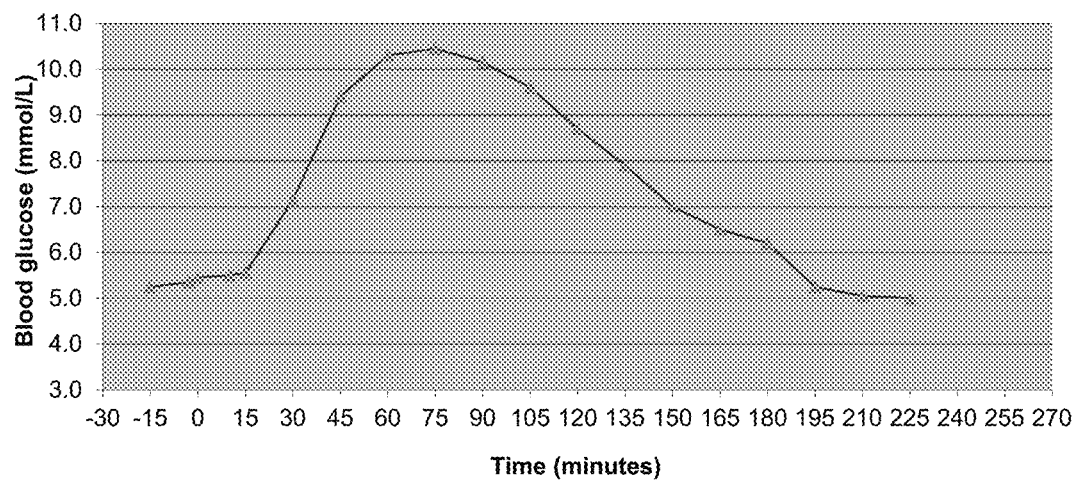
FIGS. 9-38 are curves of blood sugar versus time for individual subjects. For each of FIGS. 9-38, the following information is important:
The identity of the subject (refer to Table 1)
The drink powder ingredients (refer to Table 2): In the event that no pre-meal drink was taken, there is no reference to this table.
The drink powder protocol (refer to Table 4). This protocol refers to the amount of water and the details of the reconstitution vessel used to make the drink. In the event that no pre-meal drink was taken, there is no reference to this table.
The blood test protocol (refer to Table 5). This protocol refers to details such as the time of taking blood sugar readings, the time and nature of drink reconstitution activities, the nature and consumption time of diabetes medications, and the duration of the experiment.

A subject with impaired glucose tolerance (Subject 1) consumed a meal comprising of 4 slices white bread (see TP1 of Table 5). There was no pre-meal drink. Post-prandial blood sugar measurements are shown in FIG. 9. Note that t=120 minute blood sugar value was significantly greater than baseline. Notice that the peak blood sugar value (t=75 min) was 10.5 mmol/L. Notice further that the blood sugar values were elevated above 8.0 mmol/L for a significant period of time (100 minutes).

Figure 13:
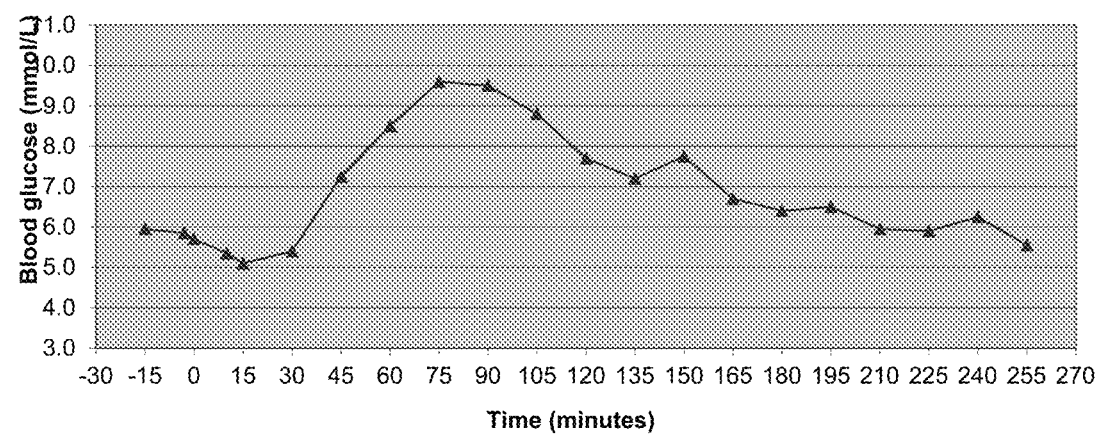

(Part 1) In another experiment the same subject (Subject 1) was given a drink (see F6 in Formulation Table and DPP1 in Drink Powder Protocol Table 4) before a bread meal (see TP4 Table 5). Post-prandial blood sugar measurements are shown In FIG. 13. Notice that the peak blood sugar value (t=75 min) was 9.6 mmol/L. Notice further that the blood sugar values were elevated above 8.0 mmol/L for a significant interval of 55 minutes. The drink in this experiment did not exhibit shear banding behaviour (see Drink 7 in Shear banding Results Table)

Figure 10:
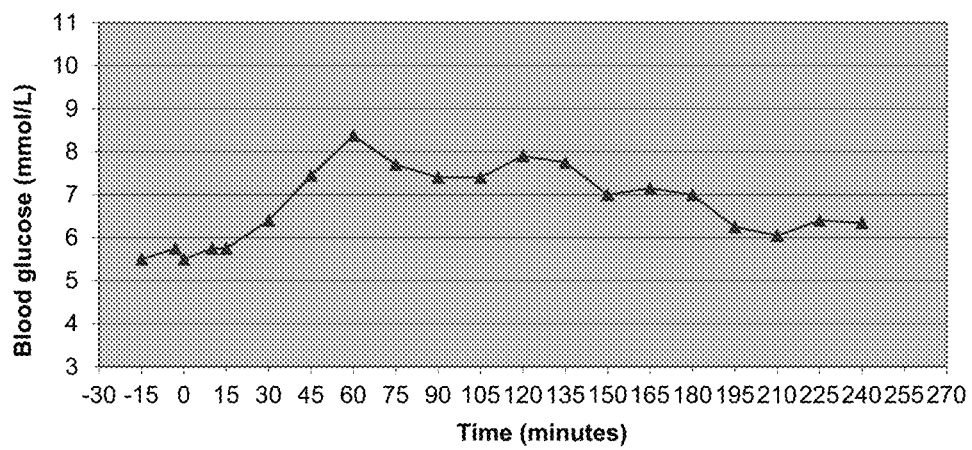

(Part 2) In another experiment the same subject (Subject 1) was given a drink (see F2 in Formulation Table 2 and DPP1 in Drink Powder Protocol Table 4) before a bread meal (see TP2 in Table 5). Post prandial blood sugar measurements are shown FIG. 10. Notice that the peak blood sugar value (t=60 min) was 8.4 mmol/L. Notice further that the blood sugar values were elevated above 8.0 mmol/L for a negligible period of time. The drink in this experiment did exhibit shear banding behaviour (see Drink 6 in Shear banding Results Table).

Figure 12:
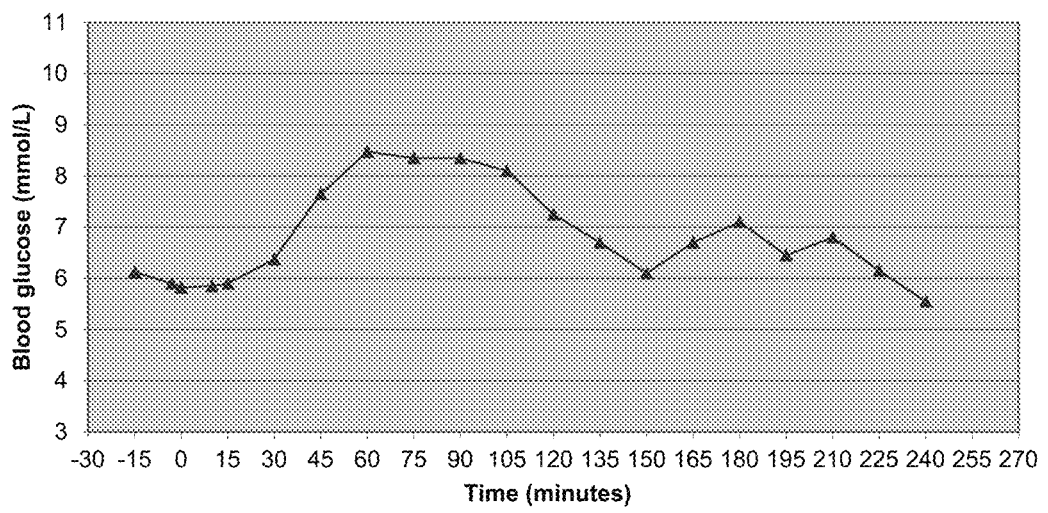

(Part 3) In another experiment the same subject (Subject 1) was given a drink (see F5 in Formulation Table 2 and DPP1 in Drink Powder Protocol Table 4) before a bread meal (see TP2 Table 5). Post prandial blood sugar measurements are shown FIG. 12. Notice that the peak blood sugar value (t=60 min) was 8.5 mmol/L. Notice further that the blood sugar values were elevated above 8.0 mmol/L for a significant interval of 55 minutes. The drink in this experiment did exhibit shear banding behaviour (see Drink 5 in Shear banding Results Table). However no protein was included in the formulation of the drink. This is not a drink according to the invention.

(Part 4) In another experiment subject 1 was given a drink (see F3 in Formulation Table 2 and DPP1 in Drink Powder Protocol Table 4) before a bread meal (see TP3 in Table 5).

Figure 11:
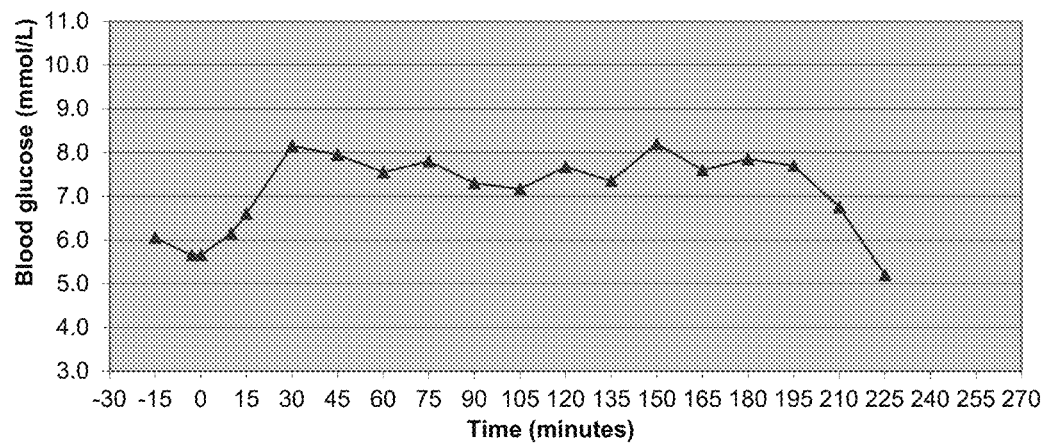

Post-prandial blood sugar measurements are shown in FIG. 11. Notice that the peak blood sugar value (t=30, 150 min) was 8.2 mmol/L. Notice that blood sugar did not return to baseline for a significant time (195 minutes). Notice that the period of elevated blood glucose is much longer than in FIG. 9. The drink in this experiment did not exhibit shear banding behaviour (see Drink 8 in Shear banding Results Table).

CONTROL EXAMPLE AND EXAMPLE 6

Figure 14:
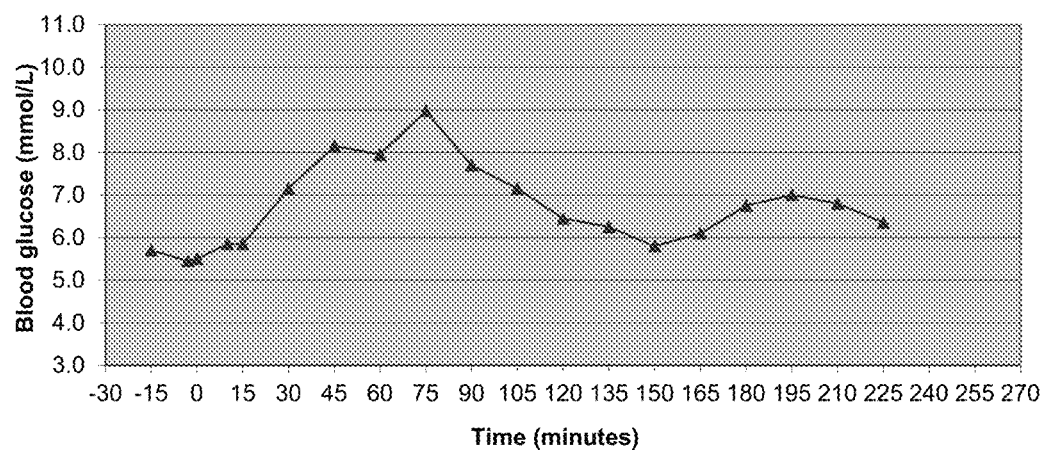

IGT Subject (Control) A subject with impaired glucose tolerance (Subject 2) consumed a meal comprising of 4 slices white bread (see TP5 in Table 5). There was no pre-meal drink. Post prandial blood sugar measurements are shown in FIG. 14. Note that t=120 minute blood sugar value was greater than the baseline value. Notice that the peak blood sugar value (t=75 min) was 9 mmol/L. Notice further that the blood sugar values were elevated above 7 mmol/L for a significant period of time, an interval of 65 minutes. Note that this subject has a more healthy blood glucose response than (Subject 1).

Figure 16:
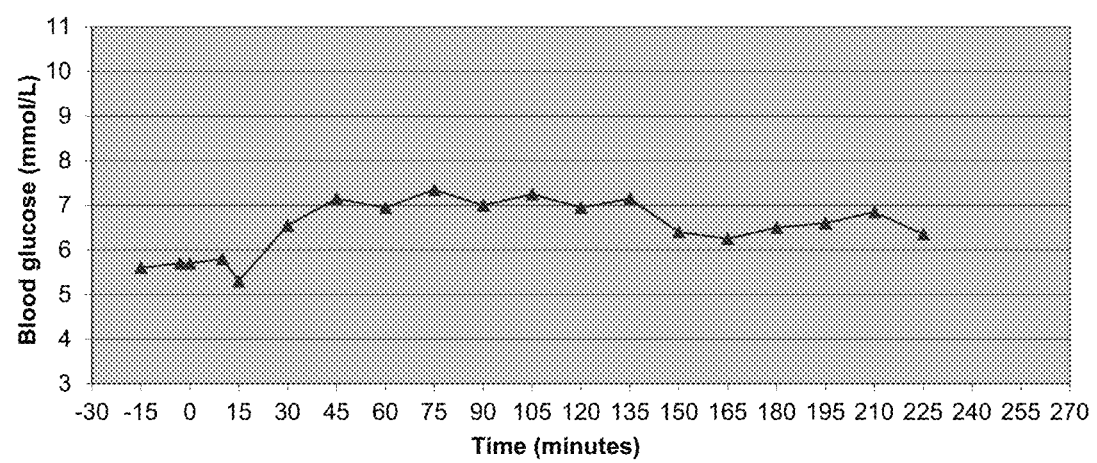

(Part 1) In another experiment the same subject (Subject 2) was given a drink (see F10 in Formulation Table 2 and DPP1 in Drink Powder Protocol Table 4) before a bread meal (see TP6 in Table 5). Post-prandial blood sugar measurements are shown in FIG. 16. Notice that the peak blood sugar value (t=75 min) was 7.4 mmol/L. Notice further that the blood sugar values were elevated at or above 7.0 mmol/L for a significant interval of 90 minutes. The drink in this experiment did not exhibit shear banding behaviour (see Drink 4 in Shear banding Results Table).

Figure 15:
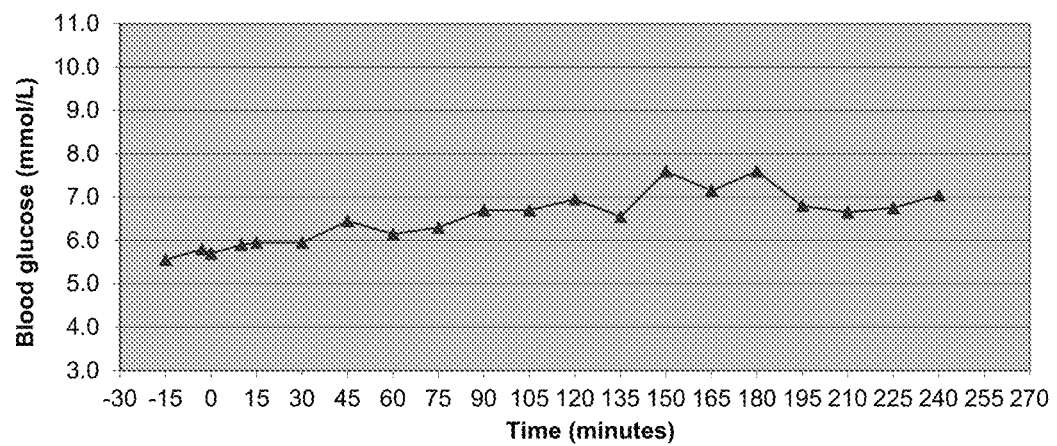

(Part 2) In another experiment the same subject (Subject 2) was given a drink (see F9 in Formulation Table 2 and DPP1 in Drink Powder Protocol Table 4) before a bread meal (see TP2 in Table 5). Post-prandial blood sugar measurements are shown FIG. 15. Notice that the peak blood sugar value (t=120 min) was 7.0 mmol/L. Notice further that the blood sugar values were elevated above 7.0 mmol/L for a negligible period of time. The drink in this experiment did exhibit shear banding behaviour (see Drink 3 in Shear banding Results Table).

CONTROL EXAMPLE AND EXAMPLE 7

Type 2 Diabetes Subject (Control) A subject with type 2 diabetes (Subject 5 in Table 1) on a regime of JANUVIA 100 mg (Sitagliptin MSD) 1 tablet daily ACTOS 30 mg (Pioglitazone) 1 tablet daily DIMIRIL 4 mg (glimepiride) 1 tablet daily. In this control experiment, the subject did not take any medications on the day of the experiment (until after the experiment was carried out). The subject consumed a meal comprising of 4 slices of gluten free bread (see TP30 in Test Protocol Table 5). There was no pre-meal drink. Post prandial blood sugar measurements are shown FIG. 32. Note that there was a significant blood glucose rise and that there was no sign of a declining blood glucose during the test period. The maximum post-prandial blood glucose value was 16.8 mmol/L (t=120 min). At the start of the experiment the subject's blood sugar was 9.8 mmol/L. The highest measured blood sugar value (t=120 min) was 16.8 mmol/L.

(Part 1) In another experiment the same subject (Subject 5) was given a drink (see F9 in Formulation Table 2, DPP3 in Drink Powder Protocol Table 4) before a meal of 4 slices of gluten free bread (see TP31 in Table 5). Post-prandial blood sugar measurements are shown FIG. 33. Note that the figure appears to be declining after (t=90 min). The maximum post-prandial blood glucose value was 14.1 mmol/L (t=90 min). At the start of the experiment the subject's blood sugar was 9.4 mmol/L. The highest measured blood sugar value (t=90 min) was 14.1 mmol/L. Note that the area under the curve, measured in terms of rise above baseline at t=120 min is significantly less when compared to graph in FIG. 32. The drink in this experiment did exhibit shear banding behaviour (see Drink 3 in Shear banding Results Table).

Figure 32:
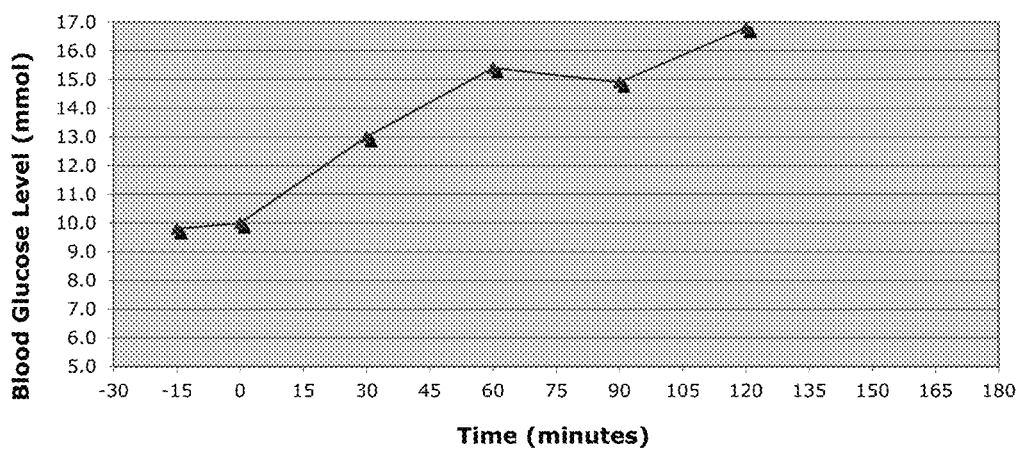
Figure 33:
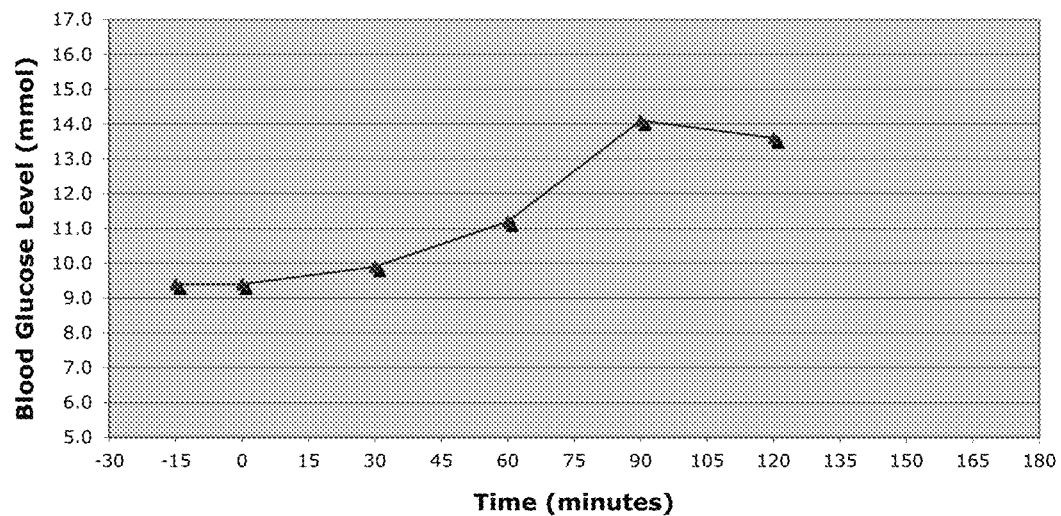
Figure 34:
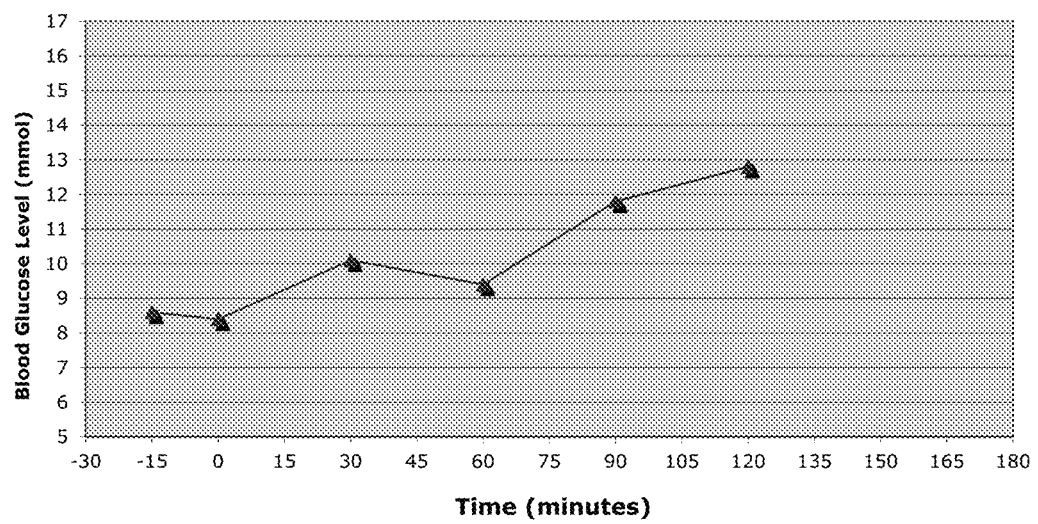

(Part 2) (Control) In another experiment the same subject (Subject 5 in Table 1) consumed a meal comprising of 4 slices of gluten free bread (see TP32 in Test Protocol Table 5) that included taking medication at the start of the meal. The medication was JANUVIA 100 mg (Sitagliptin MSD) 1 tablet ACTOS 30 mg (Pioglitazone) 1 tablet DIMIRIL 4 mg (glimepiride) 1 tablet. There was no pre-meal drink. Post-prandial blood sugar measurements are shown in FIG. 34. Note that blood sugar elevation was less than when no medication was taken (FIG. 32). Note that there was a significant blood glucose rise, though less than without taking medication (FIG. 32). There was no sign of declining blood glucose during the test period. The maximum post-prandial blood glucose value was 12.8 mmol/L (t=120 min). At the start of the experiment the subject's blood sugar was 8.6 mmol/L. The highest measured blood sugar value (t=120 min) was 12.8 mmol/L.

Figure 35:
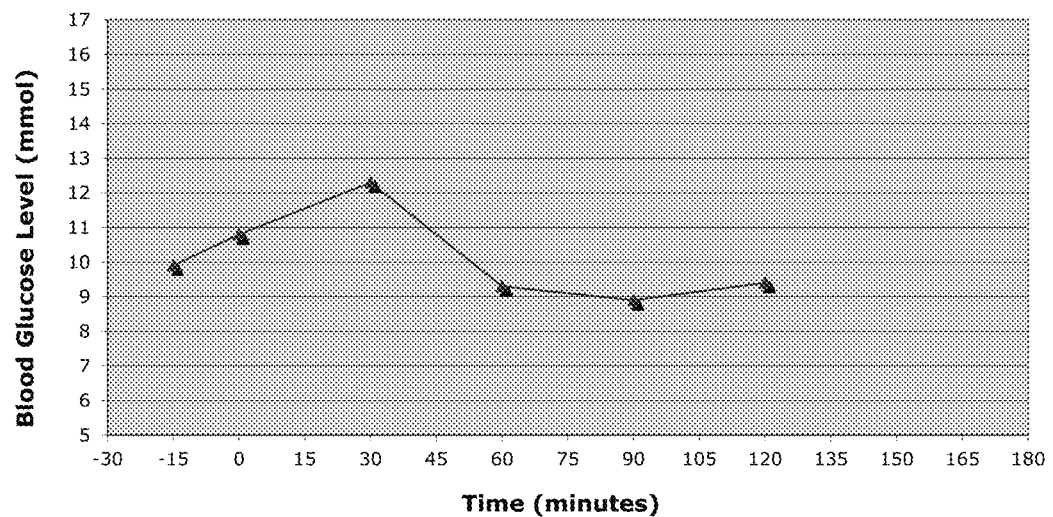

(Part 3) In another experiment the same subject (Subject 5 in Table 1) was given a drink (see F9 in Formulation Table 2, DPP3 in Drink Powder Protocol Table 4) before a meal consisting of 4 slices of gluten free bread (see TP33 in Test Protocol Table 5). Medication was taken at the start of the meal. The medication was JANUVIA 100 mg (Sitagliptin MSD) 1 tablet ACTOS 30 mg (Pioglitazone) 1 tablet DIMIRIL 4 mg (glimepiride) 1 tablet. Post-prandial blood sugar measurements are shown in FIG. 35. There is a significant decline in blood glucose levels after (t=30 min). At the start of the experiment the subject's blood sugar was 9.9 mmol/L. The highest measured blood sugar value at (t=30 min) was 12.3 mmol/L. Note that the blood glucose values after 45 minutes were all below 9.0 mmol/L. Note further that the maximum elevation above baseline blood glucose was 2.0 mmol/L. The drink in this experiment did exhibit shear banding behaviour (see Drink 3 in Shear banding Results Table).

CONTROL EXAMPLE AND EXAMPLE 8

Figure 36:
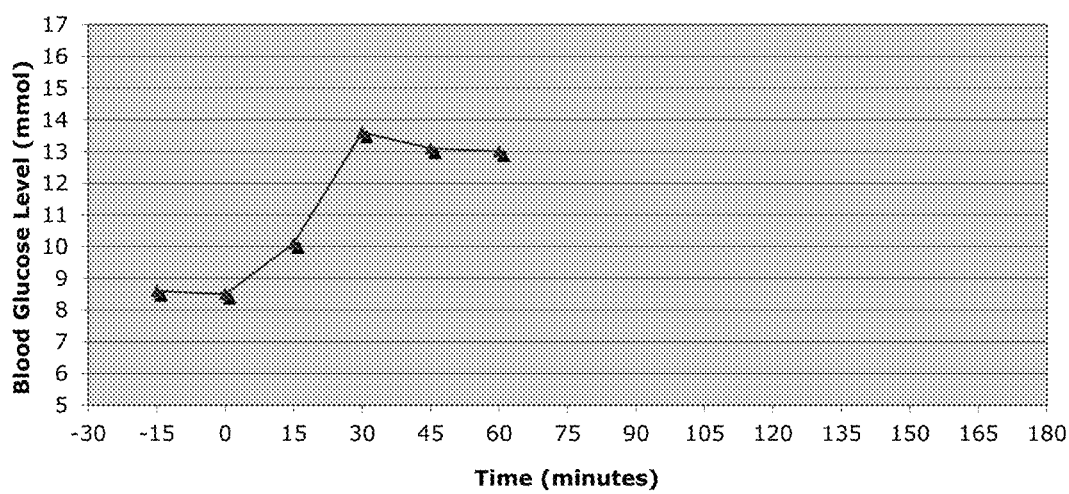

Diabetic Subject on Insulin Medication (Control) A subject with type 1 diabetes (Subject 6 in Table 1) controlled by insulin injections consumed a meal comprising of 4 slices of white bread (see TP34 in Test Protocol Table 5). There was no pre-meal drink. No insulin was taken before the meal. Post-prandial blood sugar measurements are shown (FIG. 36). Note that there was a significant blood glucose rise reaching 13.6 mmol/L at (t=30 min).

Figure 37:
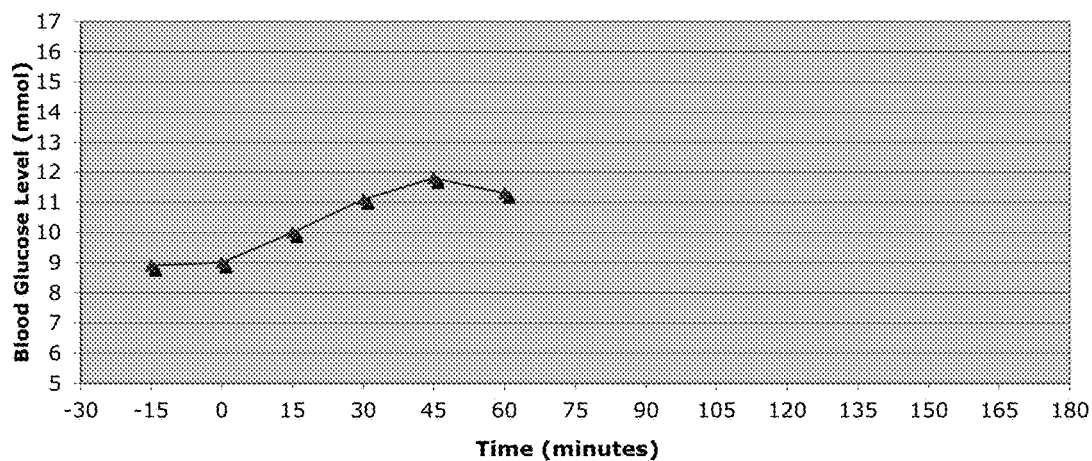

(Part 1) In another experiment the same subject (Subject 6 in Table 1) was given a drink (see F9 in Formulation Table 2, DPP3 in Drink Powder Protocol Table 4) before a meal comprising of 4 slices of white bread (see TP35 in Test Protocol Table 5). No insulin was taken before the meal. Post prandial blood sugar measurements are shown FIG. 37. Note that the maximum post-prandial blood glucose value was 11.8 mmol/L at (t=45 min). This represents a significantly slower rate of rise than when compared to (FIG. 36.) The drink in this experiment did exhibit shear banding behaviour (see Drink 3 in Shear banding Results Table).

Figure 38:
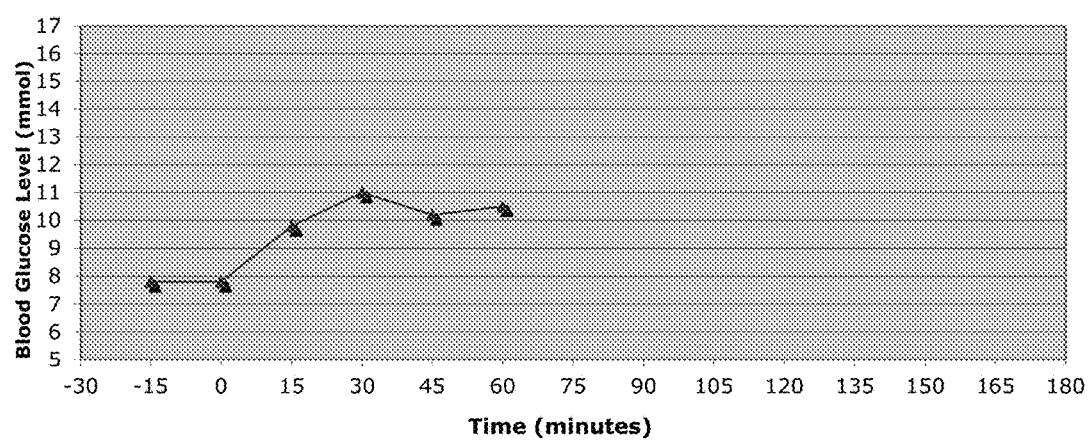

(Part 2) In another experiment the same subject (Subject 6 in Table 1) was given a drink (see F9 in Formulation Table 2, DPP3 in Drink Powder Protocol Table 4) before a meal comprising of 4 slices of white bread (see TP35 in Test Protocol Table 5). No insulin was taken before the meal. Post prandial blood sugar measurements are shown FIG. 38. Note that the maximum post-prandial blood glucose value was 11.0 mmol/L at (t=30 min). This represents a significantly slower rate of rise than when compared to (FIG. 36.) The drink in this experiment did exhibit shear banding behaviour (see Drink 3 in Shear banding Results Table).

Summary Statement For Examples 5-8 (People with Diabetes or Pre-diabetes/IGT)

Shear-banding drinks taken before a standard bread meal by patients with diabetes or pre-diabetes/IGT were found to be effective in reducing post-prandial blood sugar values. It was found that these shear banding drinks were significantly more effective than non-shear banding drinks made with comparable levels of viscosifying agent.

COMPARATIVE EXAMPLE 11

Healthy Subjects

This example examines the effect of shear banding compositions of the invention on healthy subjects.

Figure 27:
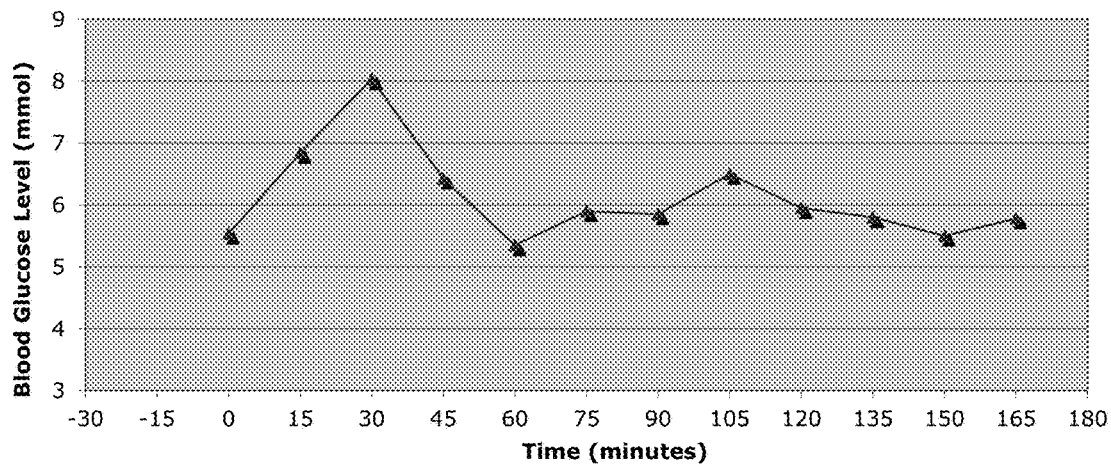

(Control) A healthy subject (Subject 4 in Table 1) was given a bread meal (see TP25 in Test Protocol Table 5). Post-prandial blood sugar measurements are shown in FIG. 27. Notice that the peak blood sugar value (t=30 min) was 8.03 mmol/L. Return to baseline was at t=60 minutes. There is a lesser secondary blood glucose peak of 6.5 mmol/L at t=105 minutes.

Figure 28:
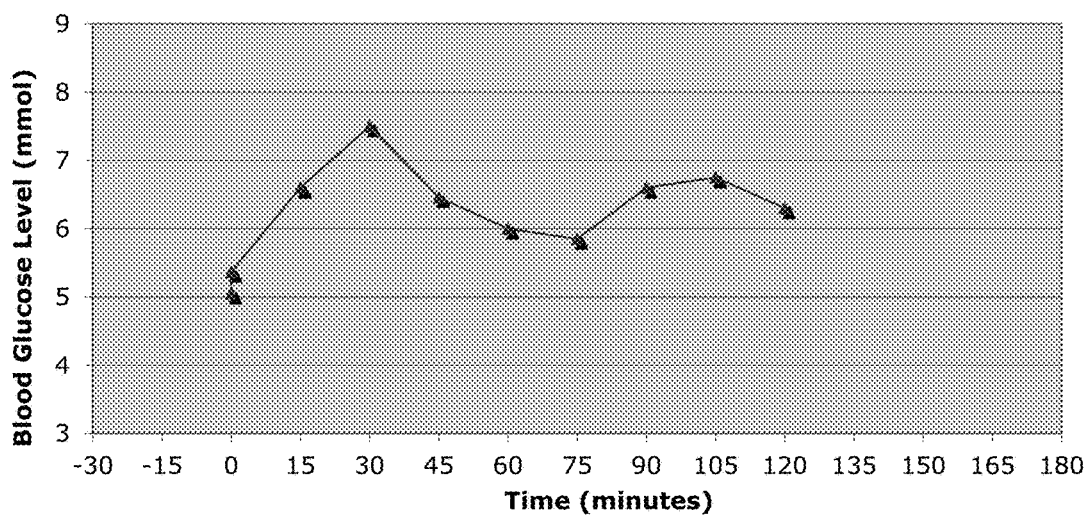

(Part 2) In another experiment the same subject (Subject 4 in Table 1) was given a drink (see F2 in Formulation Table 2, DPP1 in Drink Powder Protocol Table 4) before a bread meal (see TP26 in Test Protocol Table 5), this drink does exhibit shear banding behaviour (see Drink 6 in Shear banding Results Table). Post-prandial blood sugar measurements are shown in FIG. 28. Notice that the peak blood sugar value (t=30 min) was 7.5 mmol/L. There is a lesser secondary blood glucose peak of 6.75 mmol/L at t=105 minutes. Compare to (FIG. 27).

Figure 29:
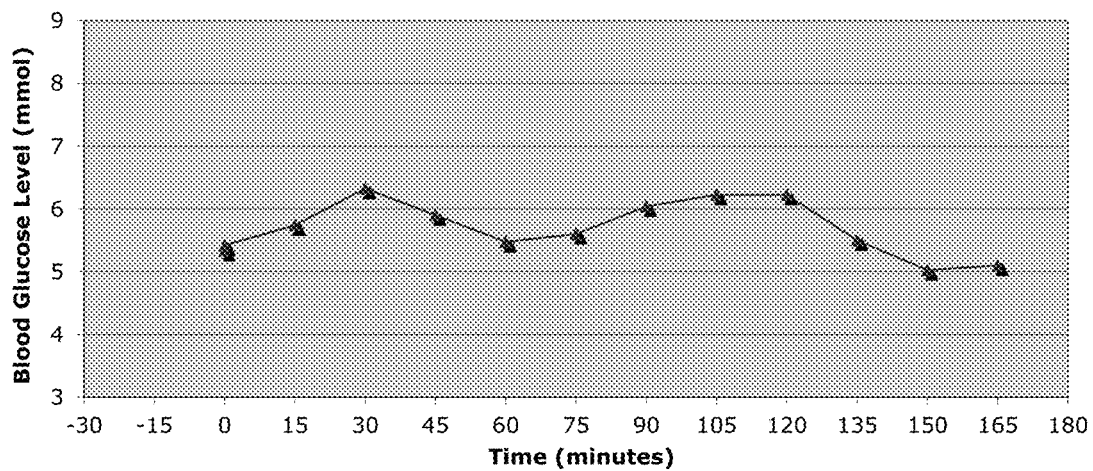

(Part 3)In another experiment the same subject (Subject 4) was given a drink (see F6 in Formulation Table 2, DPP1 in Drink Powder Protocol Table 4) before a bread meal (see TP27 in Test Protocol Table 5), this drink does not exhibit shear banding behaviour (see Drink 7 in Shear banding Results Table). Post-prandial blood sugar measurements are shown in FIG. 29. There is a modest decrease in post-prandial blood sugar at t=30 minutes in comparison to (FIG. 27).

The shear banding drink is not more effective than the non-shear banding drink in Subject 4.

Figure 30:
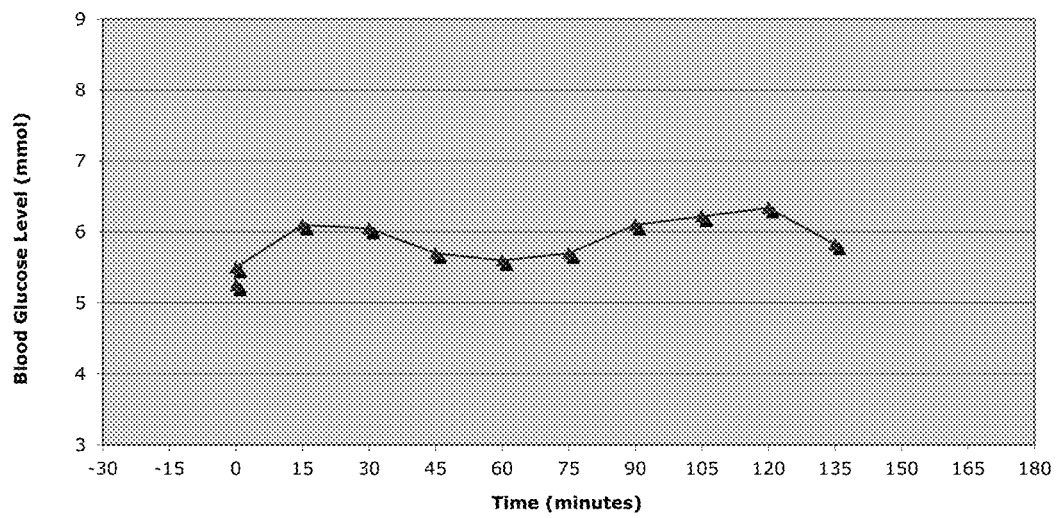
Figure 31:
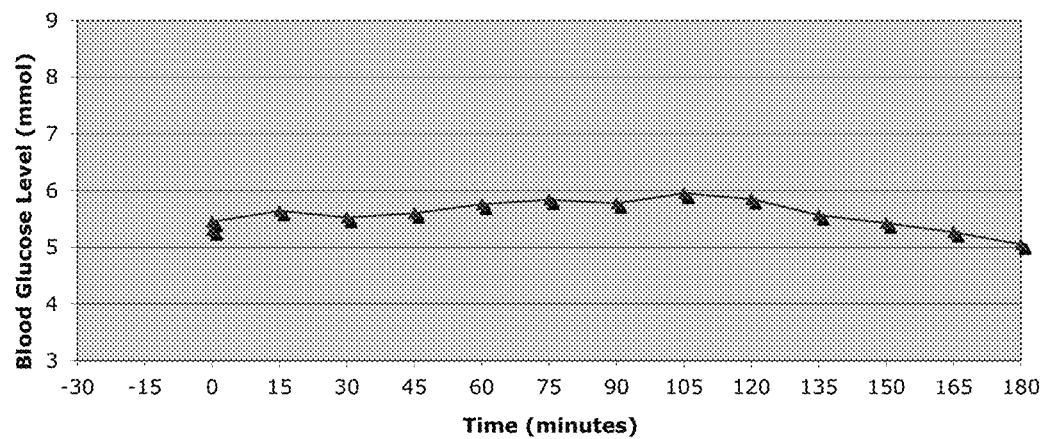

(Part 4) In another experiment the same subject (Subject 4 in Table 1) was given a drink (see F9 in Formulation Table 2, DPP1 in Drink Powder Protocol Table 4) a bread meal (see TP28 in Test Protocol Table 5), this drink exhibits shear banding behaviour (see Drink 3 in Shear banding Results Table). Post-prandial blood sugar measurements are shown in FIG. 30. There is a modest decrease in post-prandial blood sugar at t=30 minutes in comparison to (FIG. 31).

(Part 5) In another experiment the same subject (Subject 4 in Table 1) was given a drink (see F10 in Formulation Table 2, DPP1 in Drink Powder Protocol Table 4) and before a bread meal (see TP29 in Test Protocol Table 5), this drink does not exhibit shear banding behaviour (see Drink 4 in Shear banding Results Table). Post-prandial blood sugar measurements are shown in FIG. 31.

There is a significant decrease in post prandial blood sugar at t=30 minutes in comparison to (FIG. 30).

The shear banding drink is not more effective than the non-shear banding drink in Subject 4.

(Part 6) (Control) Another healthy subject (Subject 3 in Table 1) was given a bread meal (see Test Protocol 1 in Table 5). There was no pre-meal drink. Post-prandial blood sugar measurements are shown FIG. 24. Notice that the peak blood sugar value (t=45 min) was 9.4 mmol/L. There is a significant reduction of blood glucose levels t=75 minutes to 6.8 mmol/L.

Figure 24:
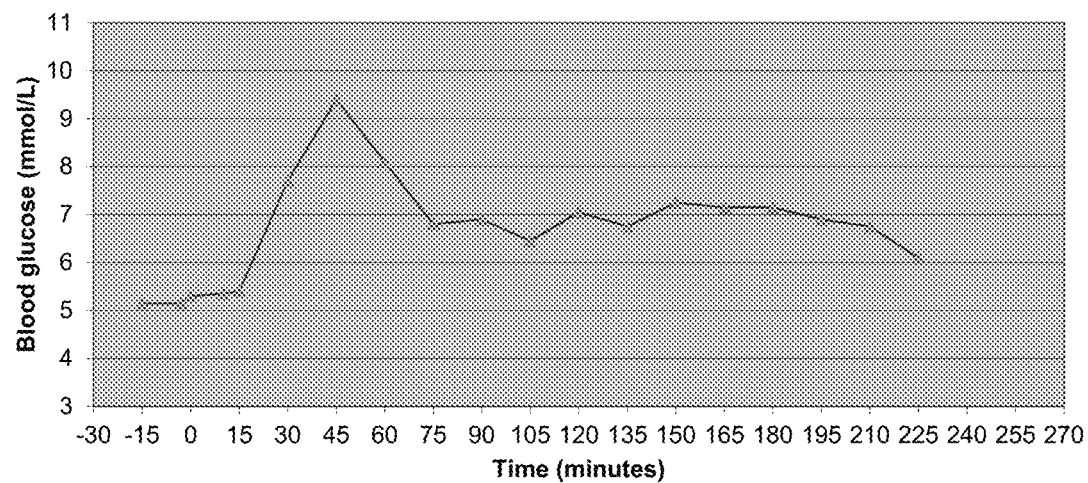
Figure 25:
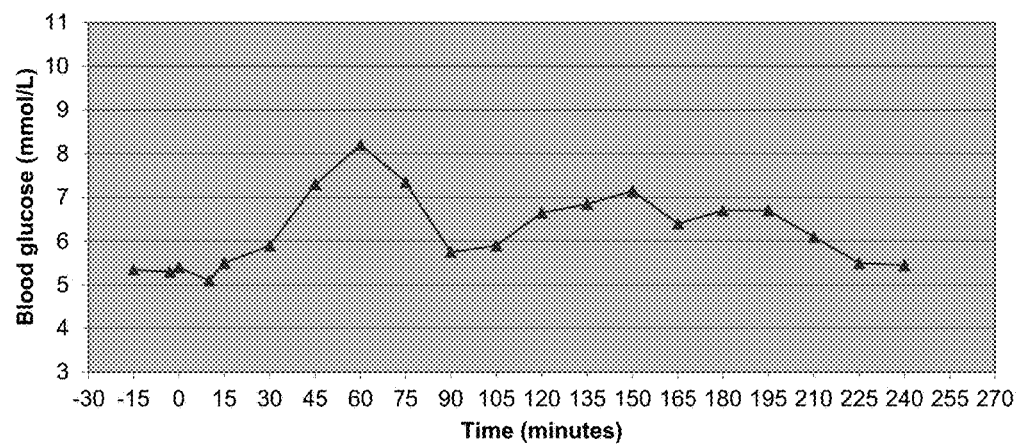

(Part 7) In another experiment the same subject (Subject 3 in Table 1) was given a drink (see F2 in Formulation Table 2, DPP1 in Drink Powder Protocol Table 4) before a bread meal (see TP2 in Test Protocol Table 5). This drink does exhibit shear banding behaviour (see Drink 6 in Shear banding Results Table). Post-prandial blood sugar measurements are shown in FIG. 25. Notice that the peak blood sugar value (t=60 min) was 8.2 mmol/L. This is only a modest reduction when compared to figure (FIG. 24).

Figure 26:
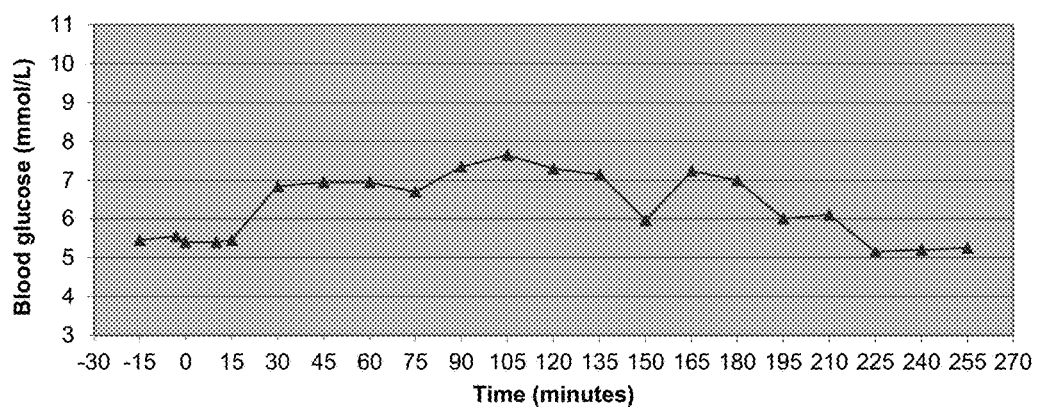

(Part 8) In another experiment the same subject (Subject 3 in Table 1) was given a drink (see F6 in Formulation Table 2, DPP1 in Drink Powder Protocol Table 4) before a bread meal (see TP4 in Test Protocol Table 5). This drink does not exhibit shear behaviour (see Drink 7 in Shear banding Results Table). Post-prandial blood sugar measurements are shown (FIG. 26). When compared to graph the blood glucose peak period of t=30 to t=75 minutes has significantly reduced.

The shear banding drink is not more effective than the non-shear banding drink in Subject 3.

Summary

From an examination of figures involving healthy people (Subjects 3 and 4) shear banding drinks are not more effective than non-shear banding drinks in reducing post-prandial blood glucose profiles.

CONTROL AND EXAMPLE 9

IGT Subject on Metformin Medication (Control) A subject with impaired glucose tolerance (Subject 2 in Table 1) consumed a meal comprising of 4 slices of white bread and 850 mg Metformin (see TP12 in Test Protocol Table 5). There was no pre-meal drink. Post-prandial blood glucose measurements are shown FIG. 17. Note that t=120 minutes blood sugar value was greater than the baseline value. Notice that the peak blood sugar value (t=45 min) was 8.2 mmol/L. Notice further that there is a significant reduction in blood glucose at t=90 minutes, 5.7 mmol/L.

Figure 17:
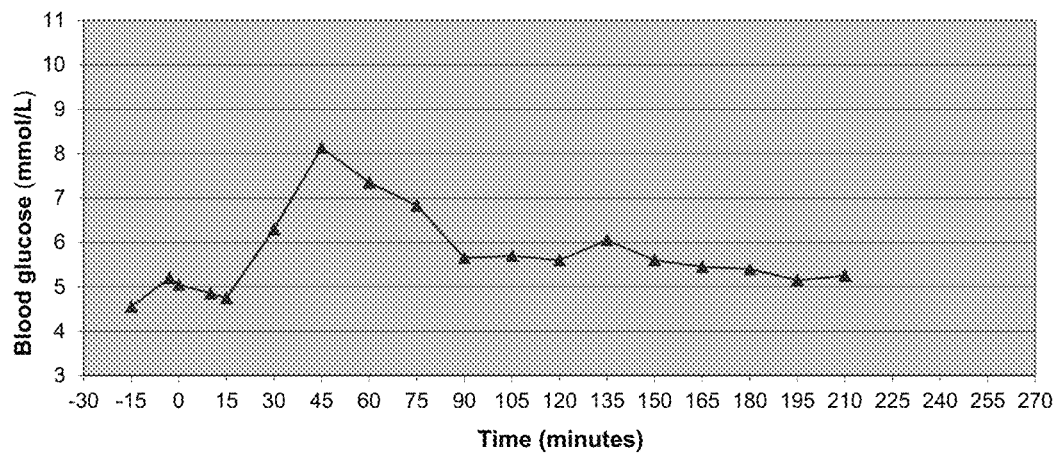
Figure 18:
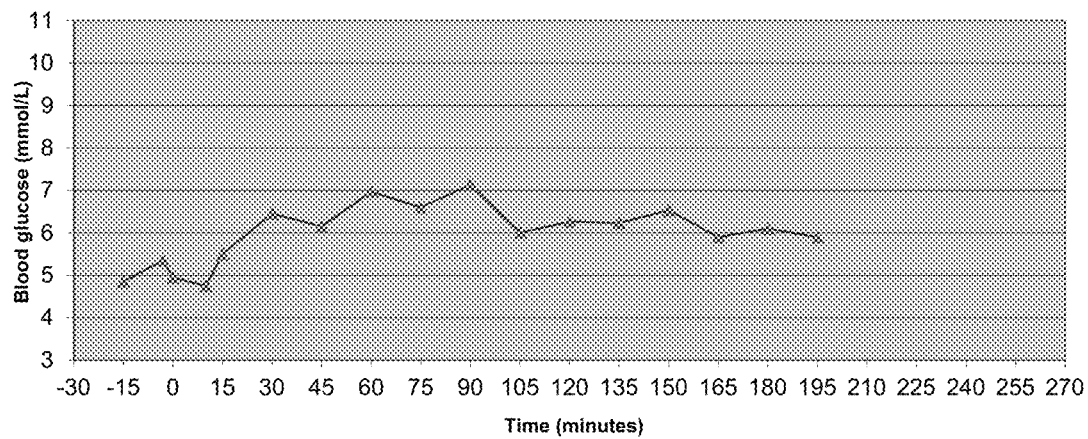

(Part 1) In another experiment the same subject (Subject 2 in Table 1) was given a shear banding drink (see F9 in Formulation Table 2, DPP3 in Drink Powder Protocol Table 4) before a bread meal with Metformin (see TP13 in Test Protocol Table 5). Post-prandial blood glucose measurements are shown FIG. 18. Notice that the peak blood sugar value (t=60, 90 min) was 7.1 mmol/L. Notice further that the blood glucose profile in this figure generally has a smoother gradient when compared to (FIG. 17).

CONTROL AND EXAMPLE 10

IGT Subject on Acarbose Medication (Control) A subject with impaired glucose tolerance (Subject 2 in Table 1) consumed a meal comprising of 4 slices of white bread and Acarbose 25 mg(see TP 16). There was no pre-meal drink. Post-prandial blood glucose measurements are shown FIG. 19. Note that there is an initial blood glucose peak at t=45 minutes of 7.5 mmol/L that lasts until t=120 minutes. This blood glucose peak was developed from an initial baseline of approximately 5.0 mmol/L.

Figure 19:
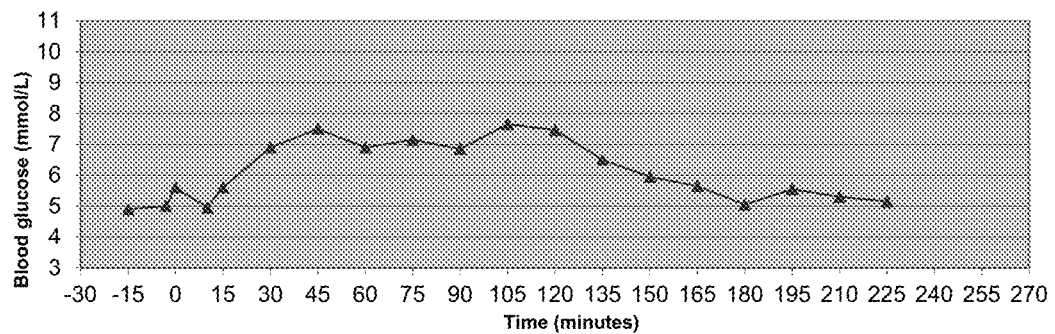

(Part 1) In another experiment the same subject (Subject 2 in Table 1) was given a shear banding drink (see F9 in Formulation Table 2, DPP3 in Drink Powder Protocol Table 4) before a bread meal with Acarbose (see TP20 in Test Protocol Table 5). 25 mg Acarbose was taken at the same time as the pre-meal drink, and the bread meal was taken 15 minutes later. Post-prandial blood glucose measurements are shown FIG. 20. The early blood glucose levels are much lower than in (FIG. 19).

Figure 20:
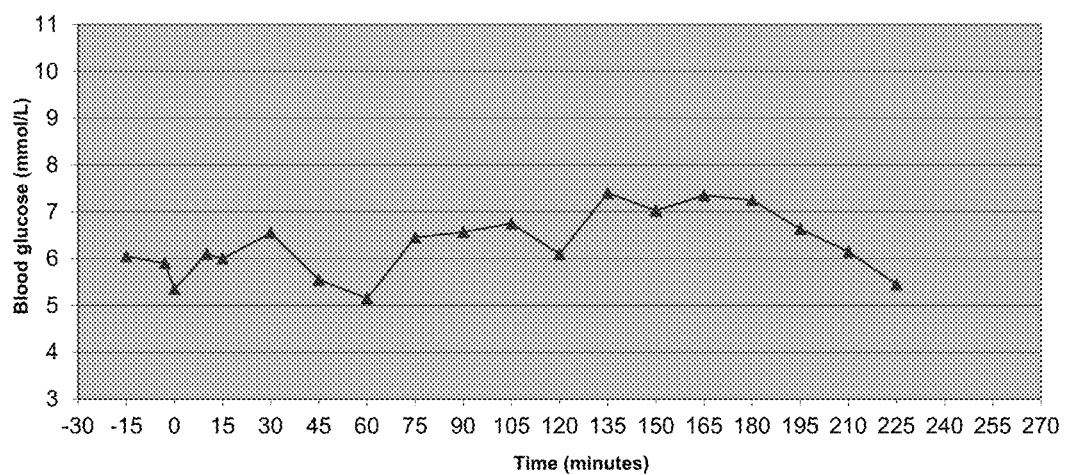
Figure 21:
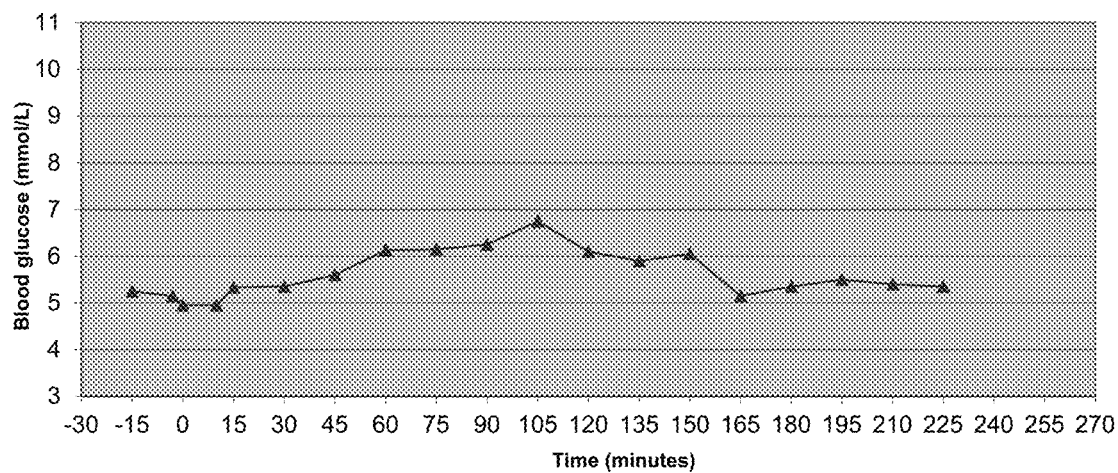

(Part 2) In another experiment the same subject (Subject 2 in Table 1) was given a shear banding drink (see F9 in Formulation table 2, DPP3 in Drink Powder Protocol Table 4) before a bread meal with Acarbose (see TP19 in Test Protocol Table 5. The pre-meal drink was taken first, and after 15 minutes, the 25 mg Acabose and bread meal were consumed together. Post-prandial blood glucose measurements are shown (FIG. 21). The early and late blood glucose levels lower than (FIG. 20). This shows that taking the pre-meal drink 15 minutes before the medication led to a better result in terms of a lower blood glucose curve.

CONTROL AND EXAMPLE 11

Figure 22:
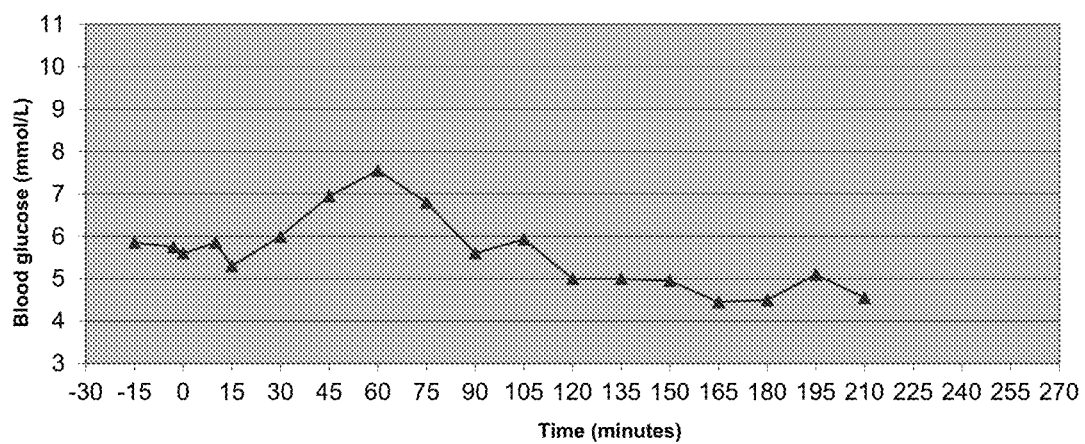

IGT Subject with Glicilazide Medication (Control) A subject with impaired glucose tolerance (Subject 2 in Table 1) consumed a meal comprising of 4 slices of white bread and Glicilazide (see TP24 in Test Protocol Table 5). There was no pre-meal drink. Post-prandial blood glucose measurements are shown in FIG. 22. Note that there is a blood glucose peak period of t=15-t=105 minutes. There was a significant blood glucose peak rising from approximately 5.8 mmol/L to 7.6 mmol/L.

Figure 23:
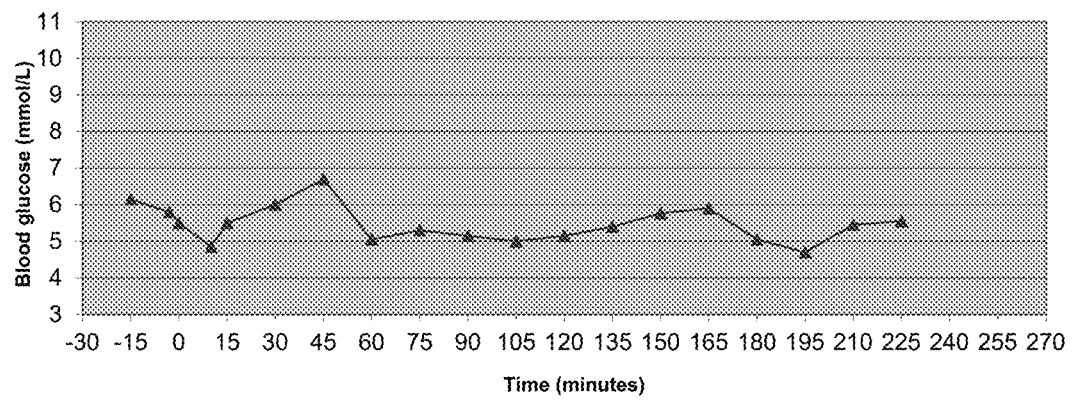

(Part 1) In another experiment the same subject (Subject 2 in Table 1) was given a shear banding drink (see F9 in Formulation table 2, DPP3 in Drink Powder Protocol Table 4) before a bread meal with Glicilazide (see TP23 in Test Protocol Table 5). Post-prandial blood glucose measurements are shown (FIG. 23). In this blood glucose profile there is only a minor blood glucose peak above baseline at t=45 minutes when compared with the blood glucose profile shown in (FIG. 23).

It has been shown that the use of drinks of the invention, when taken in conjunction with diabetes medication, can lead to reduced blood glucose profiles relative to the consumption of diabetes medicine without the drink. This effect is most pronounced when the drink of the invention is taken separately at some time before the standard meal, and if the medications are taken with the meal as is commonly recommended.

TABLE 2

Drink ingredients including dry powder composition and weights, and water volume used to prepare the drink. Does not describe drink preparation process (see Test Protocol Table 5)

| | |
|---|---|
| F2 | 10gwpc80 + 5 g Guar gum + 150 ml water |
| F3 | 10gwpc80 + 150 ml water |
| F5 | 5 g guar + 150 ml water |
| F6 | 10gwpc80 + 5 g psyllium husk powder + 150 ml water |
| F9 | 20gwpc80 + 5 g guar + 150 ml water, |
| F10 | 20gwpc80 + 5 g psyllium husk powder + 150 ml water |

TABLE 3

Shear banding Results Table: Describes results for drinks made as described in Formulation table 2.

| Drink No. | Drink description. (See Formulation table 2) | angle A | Shear banding Yes/No |
|---|---|---|---|
| Drink 3 | F9 | 25° | Yes |
| Drink 3 | F9 (Repeat) | 27° | Yes |
| Drink 4 | F10 | Multiple rotations of 360° (approximately ×10) | No |
| Drink 5 | F5 | 12° | Yes |
| Drink 6 | F2 | Multiple rotations of 360° (approximately ×4) | No |
| Drink 6 | F2 (repeat 1, @ 10 minute) | 12° | Yes |
| Drink 6 | F2 (repeat 2, @ 15 minute) | 13° | Yes |
| Drink 7 | F6 | Multiple rotations of 360° (too many to count) | No |
| Drink 7 | F6 (repeat 1) | Multiple rotations of 360° (too many to count) | No |
| Drink 7 | F6 (repeat 2, @ 10 minutes | 339° | No |
| Drink 7 | F6 (repeat 3, @ 15 minutes | 325° | No |
| Drink 8 | F3 | Multiple rotations of 360° (too many to count) | No |

TABLE 4

Drink Powder Protocol: Describes handling of the dry drink ingredients prior to reconstitution.

| | |
|---|---|
| DPP1 | Ingredients were chosen based on formulation number (e.g. F2-F10) according to (Table 2) Ingredients were weighed out individually and placed into a 200 ml plastic cup. The ingredients were then mixed vigorously with a teaspoon. |
| DPP2 | Ingredients were chosen based on formulation number (e.g. F2-F10) according to (Table 2) Ingredients were weighed out individually and placed into a 350 ml plastic cup. The ingredients were then mixed vigorously with a teaspoon. |
| DPP3 | Ingredients were chosen based on formulation number (e.g. F2-F10) according to (Table 2) Ingredients were weighed out individually and placed into a 200 ml plastic cup. The ingredients were then mixed vigorously with a teaspoon. Ingredients were added to a 200 ml "stock bottle" with a screw cap lid. |

TABLE 5

Test Protocol: Describes protocol for measuring blood sugar in various subjects and includes information on re-constitution of the drink, length of the trial, amount of water consumed with bread (if any), type of bread, type of medication (if any).

| | |
|---|---|
| TP1 | Subject took a baseline blood glucose reading (t = −15). 12 minutes later subject took another baseline blood glucose reading (t = −3). 3 minutes later subject took another baseline blood glucose reading (t = 0). 10 minutes later the subject started to consume 4 slices of white bread, along with 250 ml water, over a 5 minute period (t = 10). Immediately after having consumed the bread (t = 15), and every 15 minutes afterwards for a further 210 minutes, subject took a blood glucose reading. |
| TP2 | Subject took baseline blood glucose reading (t = −15). 12 minutes later subject took another baseline blood glucose reading (t = −3). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread, along with 100 ml of water, and was instructed to have consumed the bread along with the water within 8 minutes. A blood glucose reading was taken 3 minutes after the drink formulation had been consumed (t = 0) even if the subject was midway through consuming the four slices of white bread. 10 minutes later the subject took another blood glucose reading (bread had been consumed well before this point). 5 minutes later (t = 15), and every 15 minutes afterwards for a further 225 minutes, the subject took a blood glucose reading. |
| TP3 | Subject took baseline blood glucose reading (t = −15). 12 minutes later subject took another baseline blood glucose reading (t = −3). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread, along with 250 ml of water, and was instructed to have consumed the bread along with the water within 8 minutes. A blood glucose reading was taken 3 minutes after the drink formulation had been consumed (t = 0) even if the subject was midway through consuming the four slices of white bread. 10 minutes later the subject took another blood glucose reading (bread had been consumed well before this point). 5 minutes later (t = 15), and every 15 minutes afterwards for a further 210 minutes, the subject took a blood glucose reading. |
| TP4 | Subject took baseline blood glucose reading (t = −15). 12 minutes later subject took another baseline blood glucose reading (t = −3). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread, along with 100 ml of water, and was instructed to have consumed the bread along with the water within 8 minutes. A blood glucose reading was taken 3 minutes after the drink formulation had been consumed (t = 0) even if the subject was midway through consuming the four slices of white bread. 10 minutes later the subject took another blood glucose reading (bread had been consumed well before this point). 5 minutes later (t = 15), and every 15 minutes afterwards for a further 240 minutes, the subject took a blood glucose reading. |
| TP5 | Subject took a baseline blood glucose reading (t = −15). 12 minutes later subject took another baseline blood glucose reading (t = −3). 3 minutes later subject took another baseline blood glucose reading (t = 0). 10 minutes later the subject started consuming 4 slices of white bread, along with 150 ml of water, over a 5 minute period (t = 10). Immediately after having consumed the bread (t = 15), and every 15 minutes afterwards for a further 210 minutes, subject took a blood glucose reading. |
| TP6 | Subject took baseline blood glucose reading (t = −15). 12 minutes later subject took another baseline blood glucose reading (t = −3). Subject then added 150 ml of water to the 200 ml plastic cup containing the previously weighed out and mixed dry drink ingredients ingredients. Subject then mixed the ingredients and water with a teaspoon vigorously till near uniformity was reached. Subject then consumed the drink formulation as quickly as possible. The subject then immediately began to consume 4 slices of white bread, along with 150 ml of water, and was instructed to have consumed the bread along with the water within 8 minutes. A blood glucose reading was taken 3 minutes after the drink formulation had been consumed (t = 0) even if the subject was midway through consuming the four slices of white bread. 10 minutes later the subject took another blood glucose reading (bread had been consumed well before this point). 5 minutes later (t = 15), and every 15 minutes afterwards for a further 210 minutes, the subject took a blood glucose reading. |
| TP12 | Subject took a baseline blood glucose reading (t = −15). 12 minutes later subject took another baseline blood glucose reading (t = −3). 3 minutes later subject took another baseline blood glucose reading (t = 0). 10 minutes later (t = 10) the subject took a blood glucose reading then ate a mouthful of the 4 slices of white bread along with 850 mg of Metformin. The subject then consumed the remainder of the 4 slices of white bread, along with 250 ml water, over a 5 minute period. |

TABLE 5-continued

Test Protocol: Describes protocol for measuring blood sugar in various subjects and includes information on re-constitution of the drink, length of the trial, amount of water consumed with bread (if any), type of bread, type of medication (if any).

|      | |
|------|---|
|      | Immediately after having consumed the bread (t = 15), and every 15 minutes afterwards for a further 195 minutes, subject took a blood glucose reading. |
| TP13 | Subject took baseline blood glucose reading (t = −15). 12 minutes later subject took another baseline blood glucose reading (t = −3). Subject then opened the lid of the 'stock bottle' containing the dry drink ingredients and added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t = 0). 10 minutes later (t = 10) the subject took a blood glucose reading then ate a mouthful of the 4 slices of white bread along with 850 mg of Metformin. The subject then consumed the remainder of the 4 slices of white bread, along with 250 ml water, over a 5 minute period. Immediately after having consumed the bread (t = 15), and every 15 minutes afterwards for a further 180 minutes, subject took a blood glucose reading. |
| TP14 | Subject took baseline blood glucose reading (t = −15). 12 minutes later subject took another baseline blood glucose reading (t = −3). Subject then opened the lid of the 'stock bottle' containing the dry drink ingredients and added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. The subject then consumed 850 mg of Metformin and then consumed the drink formulation as quickly as possible and took another blood glucose reading (t = 0). 10 minutes later (t = 10) the subject took a blood glucose reading then consumed 4 slices of white bread, along with 250 ml water, over a 5 minute period. Immediately after having consumed the bread (t = 15), and every 15 minutes afterwards for a further 210 minutes, subject took a blood glucose reading. |
| TP16 | Subject took a baseline blood glucose reading (t = −15). 12 minutes later subject took another baseline blood glucose reading (t = −3). 3 minutes later subject took another baseline blood glucose reading (t = 0). 10 minutes later (t = 10) the subject took a blood glucose reading then ate a mouthful of the 4 slices of white bread along with 25 mg of Acarbose. The subject then consumed the remainder of the 4 slices of white bread, along with 250 ml water, over a 5 minute period. Immediately after having consumed the bread (t = 15), and every 15 minutes afterwards for a further 210 minutes, subject took a blood glucose reading. |
| TP19 | Subject took baseline blood glucose reading (t = −15). 12 minutes later subject took another baseline blood glucose reading (t = −3). Subject then opened the lid of the 'stock bottle' containing the dry drink ingredients and added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t = 0). 10 minutes later (t = 10) the subject took a blood glucose reading then ate a mouthful of the 4 slices of white bread along with 25 mg of Acarbose. The subject then consumed the remainder of the 4 slices of white bread, along with 150 ml water, over a 5 minute period. Immediately after having consumed the bread (t = 15), and every 15 minutes afterwards for a further 210 minutes, subject took a blood glucose reading. |
| TP20 | Subject took baseline blood glucose reading (t = −15). 12 minutes later subject took another baseline blood glucose reading (t = −3). Subject then opened the lid of the 'stock bottle' containing the dry drink ingredients and to added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. The subject then consumed 25 mg of Acarbose and then consumed the drink formulation as quickly as possible and took another blood glucose reading (t = 0). 10 minutes later (t = 10) the subject took a blood glucose reading then consumed 4 slices of white bread, along with 150 ml water, over a 5 minute period. Immediately after having consumed the bread (t = 15), and every 15 minutes afterwards for a further 210 minutes, subject took a blood glucose reading. |
| TP23 | Subject took baseline blood glucose reading (t = −15). 12 minutes later subject took another baseline blood glucose reading (t = −3). Subject then opened the lid of the 'stock bottle' containing the dry drink ingredients and to added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t = 0). 10 minutes later (t = 10) the subject took a blood glucose reading then ate a mouthful of the 4 slices of white bread along with 40 mg of Glicalazide. The subject then consumed the remainder of the 4 slices of white bread, along with 250 ml water, over a 5 minute period. Immediately after having consumed the |

TABLE 5-continued

Test Protocol: Describes protocol for measuring blood sugar in various subjects and includes information on re-constitution of the drink, length of the trial, amount of water consumed with bread (if any), type of bread, type of medication (if any).

|      | |
|------|---|
|      | bread (t = 15), and every 15 minutes afterwards for a further 195 minutes, subject took a blood glucose reading. |
| TP24 | Subject took a baseline blood glucose reading (t = −15). 12 minutes later subject took another baseline blood glucose reading(t = −3). 3 minutes later subject took another baseline blood glucose reading (t = 0). 10 minutes later (t = 10) the subject took a blood glucose reading then ate a mouthful of the 4 slices of white bread along with 40 mg of Glicalazide. The subject then consumed the remainder of the 4 slices of white bread, along with 250 ml water, over a 5 minute period. Immediately after having consumed the bread (t = 15), and every 15 minutes afterwards for a further 195 minutes, subject took a blood glucose reading. |
| TP25 | Subject took a baseline blood glucose reading. Subject then consumed 4 white slices of bread. Subject took a blood glucose reading every 15 minutes after consuming the bread for 165 minutes. |
| TP26 | Subject took baseline blood glucose reading (t = 0). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread. No water was consumed with bread. A blood glucose reading was taken immediately after the 4 slices of white bread had been consumed (t = 0). Then the subject took a blood glucose reading every 15 minutes for a further 120 minutes. |
| TP27 | Subject took baseline blood glucose reading (t = 0). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread. No water was consumed with bread. A blood glucose reading was taken immediately after the 4 slices of white bread had been consumed (t = 0). Then the subject took a blood glucose reading every 15 minutes for a further 165 minutes. |
| TP28 | Subject took baseline blood glucose reading (t = 0). Subject then added 150 ml of water to the 200 ml plastic cup containing the previously weighed out and mixed dry drink ingredients. Subject then mixed the ingredients and water with a teaspoon vigorously till near uniformity was reached. Subject then consumed the drink formulation as quickly as possible. The subject then immediately began to consume 4 slices of white bread. No water was consumed with bread. A blood glucose reading was taken immediately after the 4 slices of white bread had been consumed (t = 0). Then the subject took a blood glucose reading every 15 minutes for a further 135 minutes. |
| TP29 | Subject took baseline blood glucose reading (t = 0). Subject then added 150 ml of water to the 200 ml plastic cup containing the previously weighed out and mixed drink ingredients ingredients. Subject then mixed the ingredients and water with a teaspoon vigorously till near uniformity was reached. Subject then consumed the drink formulation as quickly as possible. The subject then immediately began to consume 4 slices of white bread. No water was consumed with bread. A blood glucose reading was taken immediately after the 4 slices of white bread had been consumed (t = 0). Then the subject took a blood glucose reading every 15 minutes for a further 180 minutes. |
| TP30 | Subject took a baseline blood glucose reading. Subject then consumed 4 slices of gluten free bread. Immediately after having consumed the gluten free bread subject took a blood glucose reading and took a blood glucose reading every 15 minutes afterwards for 120 minutes. |
| TP31 | Subject took baseline blood glucose reading. Subject then opened the lid of the 'stock bottle' containing the dry drink ingredients and to added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. Subject then consumed the drink formulation as quickly as possible then immediately consumed 4 slices of gluten free bread. Immediately after having consumed the gluten free bread subject took a blood glucose reading and took a blood glucose reading every 15 minutes afterwards for 120 minutes. |
| TP32 | Subject took baseline blood glucose reading. The subject then had two mouthfuls of the 4 slices of gluten free bread. The subject then took the following medications (consistent with the subject's daily regime) Dimirel glimpiride, Januvia sitagliptin phosphate monohydrate, Actos Pioglitazone HCl. Immediately after the subject had consumed their medication, the subject then consumed the remaining amount of the 4 slices of gluten free bread. Immediately after having consumed the gluten free bread the subject took a blood glucose reading and took a blood glucose reading every 15 minutes afterwards for 120 minutes. |
| TP33 | Subject took a baseline blood glucose reading. Subject then opened the lid of the 'stock bottle' containing the dry drink ingredients and to added 150 ml of water to the drink. Subject then quickly replaced the lid to the stock bottle. Subject then began vigorously shaking the sealed bottle in an up and down motion until they believed there to be uniformity. They were told to shake the bottle hard for no less than 10 seconds. Subject then consumed the drink formulation as quickly as |

TABLE 5-continued

Test Protocol: Describes protocol for measuring blood sugar in various subjects and includes information on re-constitution of the drink, length of the trial, amount of water consumed with bread (if any), type of bread, type of medication (if any).

possible then immediately had two mouthfuls of the 4 slices of gluten free bread. The subject then took the following medications (part of subject's daily regime) Dimirel glimpiride, Januvia sitagliptin phosphate monohydrate, Actos Pioglitazone HCl. Immediately after the subject consumed their medication, the subject then consumed the remaining amount of the 4 slices of gluten free bread. Immediately after having consumed the gluten free bread subject took a blood glucose reading and took a blood glucose reading every 15 minutes afterwards for 120 minutes.

TP34 Subject took a baseline blood glucose reading. Subject then consumed 4 slices of white bread. Immediately after having consumed the white bread subject took a blood glucose reading and took a blood glucose reading every 15 minutes afterwards for 60 minutes.

TP35 Subject took baseline blood glucose reading. Subject then opened the lid of the 'stock bottle' containing the dry drink ingredients and to added 150 ml of water to the drink. Subject then quickly replaced the lid to the stock bottle. Subject then began to vigorously shake the sealed bottle in an up and down motion until they believed there was uniformity. They were told to shake the bottle hard for no less than 10 seconds. Subject then consumed the drink formulation as quickly as possible then immediately consumed 4 slices of white bread. Immediately after having consumed the white bread subject took a blood glucose reading and took a blood glucose reading every 15 minutes afterwards for 60 minutes.

TABLE 6

Summarises the experimental parameters used to generate each figure of blood glucose profile in the attached drawings.

| FIG. | Subject (see Table 1) | Formulation (see Table 2) | Drink Powder Protocol (see Table 4) | Test protocol (see Table 5) |
|---|---|---|---|---|
| 9  | 1 | —  | —    | TP1  |
| 10 | 1 | F2 | DPP1 | TP2  |
| 11 | 1 | F3 | DPP1 | TP3  |
| 12 | 1 | F5 | DPP1 | TP2  |
| 13 | 1 | F6 | DPP1 | TP4  |
| 14 | 2 | —  | —    | TP5  |
| 15 | 2 | F9 | DPP1 | TP2  |
| 16 | 2 | F10| DPP1 | TP6  |
| 17 | 2 | —  | —    | TP12 |
| 18 | 2 | F9 | DPP3 | TP13 |
| 19 | 2 | —  | —    | TP16 |
| 20 | 2 | F9 | DPP3 | TP20 |
| 21 | 2 | F9 | DPP3 | TP19 |
| 22 | 2 | —  | —    | TP24 |
| 23 | 2 | F9 | DPP3 | TP23 |
| 24 | 3 | —  | —    | TP1  |
| 25 | 3 | F2 | DPP1 | TP2  |
| 26 | 3 | F6 | DPP1 | TP4  |
| 27 | 4 | —  | —    | TP25 |
| 28 | 4 | F2 | DPP1 | TP26 |
| 29 | 4 | F6 | DPP1 | TP27 |
| 30 | 4 | F9 | DPP1 | TP28 |
| 31 | 4 | F10| DPP1 | TP29 |
| 32 | 5 | —  | —    | TP30 |
| 33 | 5 | F9 | DPP3 | TP31 |
| 34 | 5 | —  | —    | TP32 |
| 35 | 5 | F9 | DPP3 | TP33 |
| 36 | 6 | —  | —    | TP34 |
| 37 | 6 | F9 | DPP3 | TP35 |
| 38 | 6 | F9 | DPP3 | TP35 |

Finally, it is understood that various other modifications and/or alterations may be made without departing from the spirit of the present invention as outlined herein.

EXAMPLES 11 to 13 and COMPARATIVE EXAMPLE 12

This Example demonstrates the variation in efficacy of compositions in control of post-prandial blood glucose as a function of shear banding interface distance determined as hereinbefore described.

The compositions of Table 7 were prepared and subject to the shear banding protocol as hereinbefore described. The compositions were found to exhibit shear banding and during the determination the interface distance was measured using the protocol for determination of interface distance as hereinbefore described.

To examine the efficacy of the compositions in moderation of post-prandial glucose, Subject 7 (in Table 1) adhered to the following method to compare Examples 11-13 (shown in Table 7) to Comparative Example 12 (shown in Table 7)

EXAMPLE 11

Subject 7 (shown in Table 1) took a baseline blood glucose reading (t=−15). 12 minutes later subject took another baseline blood glucose reading (t=−3). Subject then opened the lid of the 'stock bottle' containing the dry ingredients of 20 g Whey Protein Isolate (WPI90 containing 90% w/w protein) and 1 g guar gum and 1.5 g xanthan gum and added 150 ml of water to the bottle. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t=0). 10 minutes later (t=10) the subject took a blood glucose reading then consumed 4 slices of white bread along with 250 ml water, over a 5 minute period. Immediately after having consumed the bread (t=15), and every 15 minutes afterwards for a further 225 minutes, subject took a blood glucose reading.

Example 11 as (represented in FIG. 39) shows that a relatively small shear banding interface distance from the edge of the rotational driver (See Table 7 "interface distance") is relatively less effective.

EXAMPLE 12

Subject 7 (shown in Table 1) took a baseline blood glucose reading (t=−15). 12 minutes later subject took another baseline blood glucose reading (t=−3). Subject then opened the lid of the 'stock bottle' containing the dry ingredients of 20 g Whey Protein Isolate (WPI90 containing at least 90% w/w protein) and 5 g xanthan gum and then added 150 ml of water to the bottle. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t=0). 10 minutes later (t=10) the subject took a blood glucose reading then consumed 4 slices of white bread along with 250 ml water, over a 5 minute period. Immediately after having consumed the bread (t=15), and every 15 minutes afterwards for a further 210 minutes, subject took a blood glucose reading.

Example 12 as (represented in FIG. 40) shows that a relatively small shear banding interface distance from the edge of the rotational driver (See Table 7 "interface distance") is relatively less effective.

EXAMPLE 13

Subject 7 (shown in Table 1) took a baseline blood glucose reading (t=−15). 12 minutes later subject took another baseline blood glucose reading (t=−3). Subject then opened the lid of the 'stock bottle' containing the dry ingredients of 20 g Whey Protein Concentrate and 5 g guar gum and then added 150 ml of water to the bottle. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t=0). 10 minutes later (t=10) the subject took a blood glucose reading then consumed 4 slices of white bread along with 250 ml water, over a 5 minute period. Immediately after having consumed the bread (t=15), and every 15 minutes afterwards for a further 195 minutes, subject took a blood glucose reading.

Example 13 as (represented in FIG. 41) shows that a relatively large shear banding interface distance from the edge of the rotational driver (See Table 7 "interface distance") is most effective.

COMPARATIVE EXAMPLE 12 (Control)

Subject 7 (shown in Table 1) took a baseline blood glucose reading (t=−15). 12 minutes later subject took another baseline blood glucose reading (t=−3). Subject then consumed 4 slices of white bread along with 250 ml water, over a 5 minute period. Immediately after having consumed the bread (t=15), and every 15 minutes afterwards for a further 195 minutes, subject took a blood glucose reading.

Figure 42:
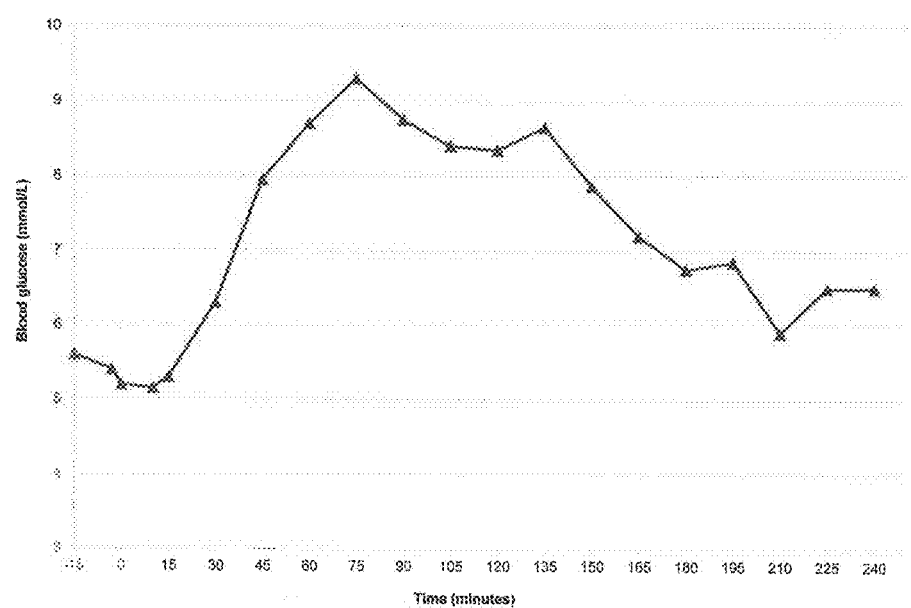
FIG. 42 is a graph of the post-prandial blood sugar measurement referred to in Example 11.

Comparative Example 12 as (represented in FIG. 42) is the control.

TABLE 7

List of shear banding formulations with different sized mobile and static layers correlating to effectiveness in post-prandial reduction of blood flucose.

Figure 39:
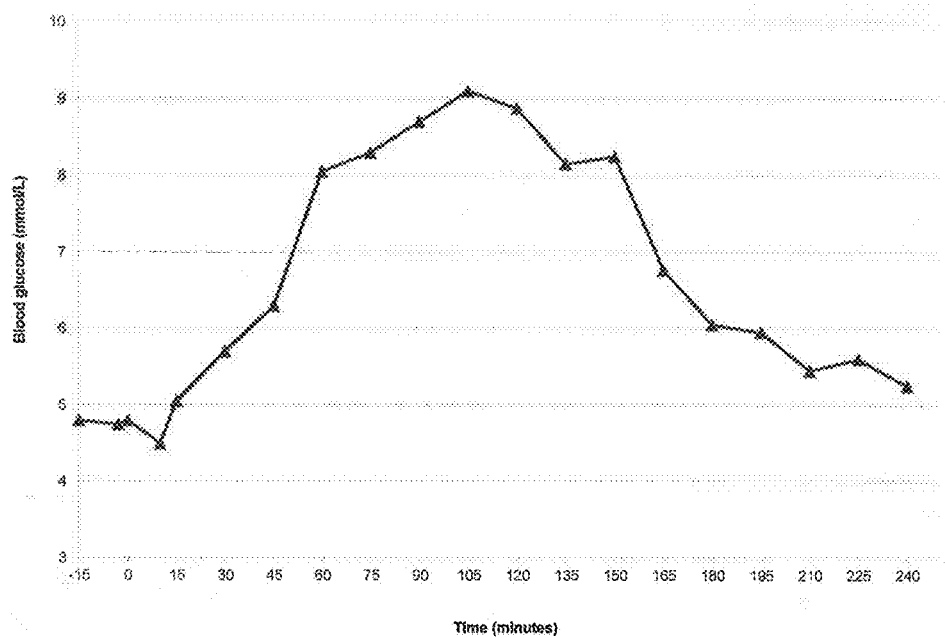
FIG. 39 is a graph of the post-prandial blood sugar measurements referred to in Example 11.
Figure 40:
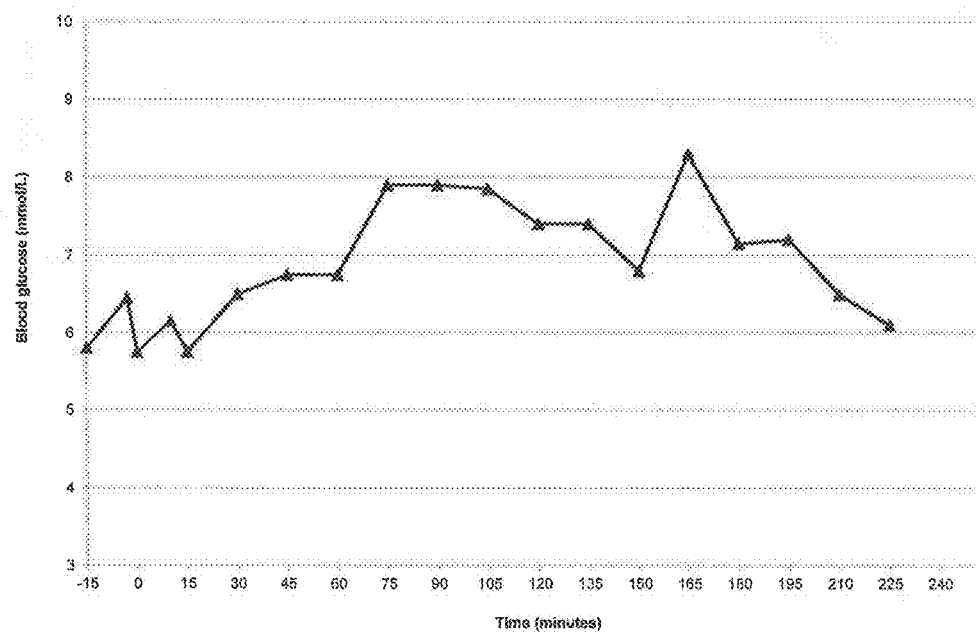
FIG. 40 is a graph of the post-prandial blood sugar measurement referred to in Example 12.
Figure 41:
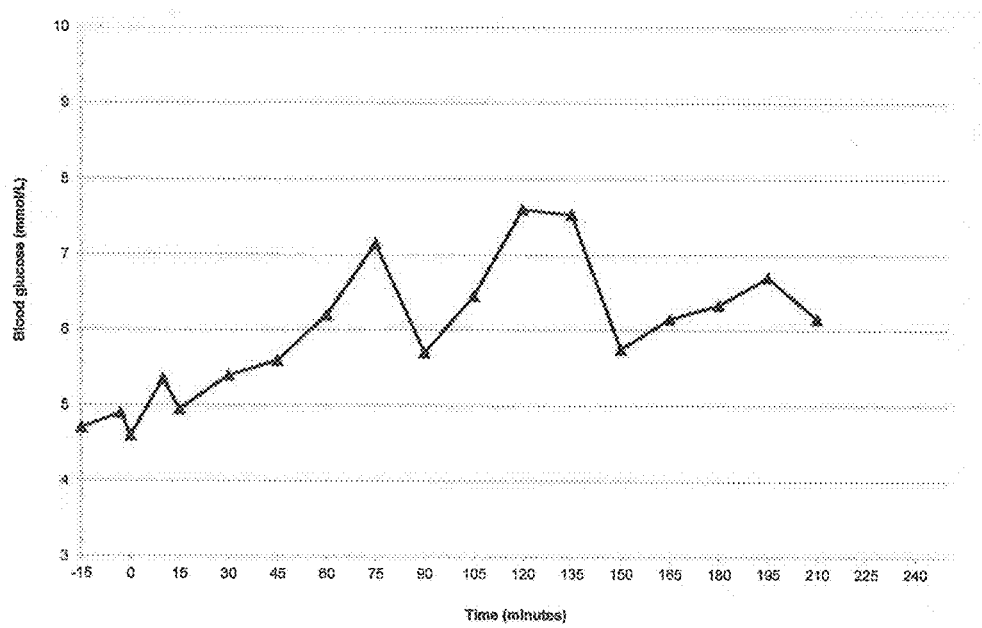
FIG. 41 is a graph of the post-prandial blood sugar measurement referred to in Example 13.

| Example | Composition | Interface distance | Effectiveness in lowering post-prandial blood glucose |
|---|---|---|---|
| 11 | 20 g Whey Protein Isolate + 1 g guar gum + 1.5 g xantham gum and 150 ml water | (approx. 2.5 mm) | Relatively less effective. FIG. 39 |
| 12 | 20 g Whey Protein Isolate + 5 g Xanthan Gum + 150 ml water | (approx.. 2.5 mm) | Relatively less effective. FIG. 40 |
| 13 | 20 g Whey Protein Concentrate + 5 g guar gum + 150 ml water | Size of mobile layer (approx. 14 mm) | Most effective. FIG. 41 |
| Comparative Example 12 | — | — | FIG. 42 |

Whey protein isolate contained at least 90% by weight protein.

The effectiveness in lowering post-prandial blood glucose are summarised in the final column of Table 7, together with the reference to the attached drawing depicting the post-prandial blood glucose response for each composition.

While Examples 11 and 12 showed some improvement over the Comparative Example the composition of Example 13 which had an interface distance of 14 mm was significantly more effective in controlling post-prandial glucose in an IGT subject.

EXAMPLES 14 to 18

Examples 14 to 18 demonstrate the invention with different types of protein sources.

The compositions of Examples 14 to 18 were prepared and tested in accordance with the above described Shear Banding Protocol. The angle "A" subtended at the centre of the circular container by the front and rear edge of the dye drop following the protocol were recorded and shown in Table 8.

TABLE 8

Figure 43:
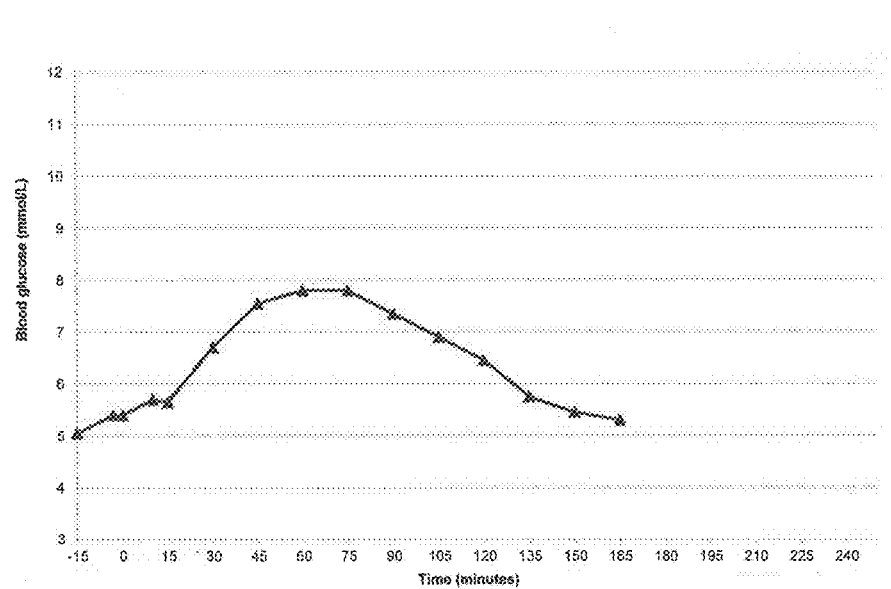
FIG. 43 is a graph of the post-prandial blood sugar measurement referred to in Example 15.
Figure 44:
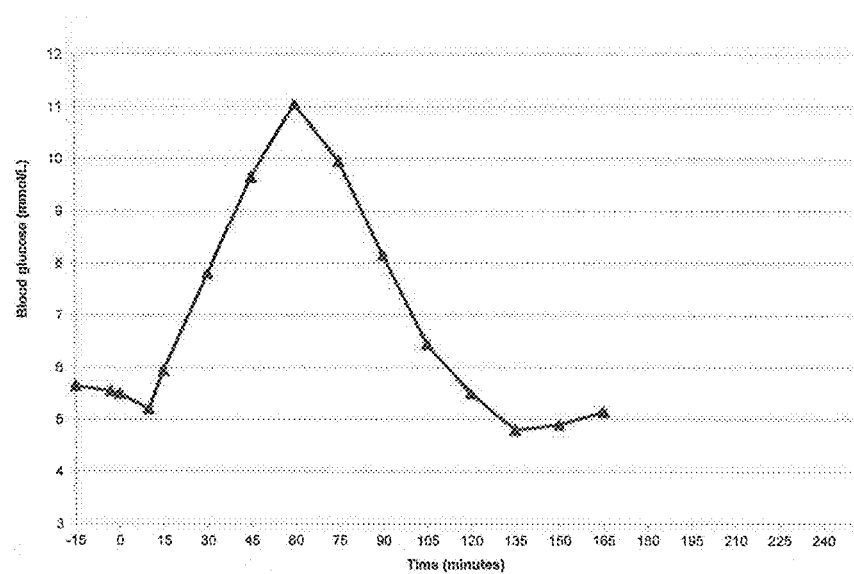
FIG. 44 is a graph of the post-prandial blood sugar measurement referred to in comparative Example 13.

| Example | Composition | Shear Banding measurement | FIG. Ref. |
|---|---|---|---|
| 14 | 20 g Whey Protein Concentrate + 5 g Guar gum + 150 ml water | Shear banding angle A < 20° | |
| 15 | 20 g Pea Protein + 5 g Guar Gum + 300 ml water | Shear banding angle A < 20° | FIG. 43 |
| 16 | 20 g Soy Protein + 5 g guar gum + 250 ml water | Shear banding angle A < 20° | |
| 17 | 20 g Milk Protein Concentrate + 1 g guar gum + 150 ml water (Milk Protein Concentrate is approximately 80% Casein, 20% Whey protein) | Shear banding angle A < 20° | — |
| 18 | 20 g Bovine Hide Gelatine + 5 g Guar Gum + 250 ml water | Shear banding angle A < 20° | |
| Comparative Example 13 | | | FIG. 44 |

Table 8 shows that a range of protein sources may be used to provide a useful shear banding composition and Examples 15, 16 and 18 containing pea protein or soy protein or bovine hide gelatine was shown to provide much improved post-prandial blood glucose levels when compared with the Comparative Example 13 control.

EXAMPLE 14

Subject 7 (shown in Table 1) took a baseline blood glucose reading (t=−15). 12 minutes later subject took another baseline blood glucose reading (t=−3). Subject then opened the lid of the 'stock bottle' containing the dry ingredients of 20 g Whey Protein Concentrate and 5 g guar gum and then added 150 ml of water to the bottle. Subject then quickly replaced the lid to the stock bottle. Subject then began to vigorously shake the sealed bottle in an up and down motion until they believed there was uniformity. They were told to shake the bottle hard for no less than 10 seconds. The subject then consumed the drink formulation as quickly as possible and took another blood glucose reading (t=0). 10 minutes later (t=10) the subject took a blood glucose reading then consumed a meal consisting of 2 slices of white bread with 4 grams of butter and 23 grams of strawberry jam (approximately 50 g of available carbohydrate) along with 220 ml coffee (1 teaspoon of coffee with 220 ml of boiling water) over a 5 minute period. Immediately after having consumed the meal (t=15), and every 15 minutes afterwards for a further 195 minutes, subject took a blood glucose reading.
Shear Banding:
The dry ingredients of 20 g Whey Protein Concentrate and 5 g guar gum were added to a "stock bottle". 150 ml of water was then added to the stock bottle. The lid of the stock bottle was replaced and then the bottle was shaken vigorously for 10 seconds. This drink was then put through the "shear banding test" as described previously (See Table 8 for result).

Example 14 shows that whey protein as the source of protein when included in the shear banding invention is effective at lowering post-prandial blood glucose when compared to Comparative Example 13 (represented in FIG. 44).

EXAMPLE 15

Subject 7 (shown in Table 1) took a baseline blood glucose reading (t=−15). 12 minutes later subject took another baseline blood glucose reading (t=−3). Subject mixed the dry ingredients of 20 g Insoluble Pea Protein and 5 g guar gum in a cup with a teaspoon. 300 ml of water was then added to the to the cup. Subject then stirred the water with the dry ingredients until there was uniformity. The subject then consumed the drink formulation as quickly as possible and took another blood glucose reading (t=0). 10 minutes later (t=10) the subject took a blood glucose reading then consumed a meal consisting of 2 slices of white bread with 4 grams of butter and 23 grams of strawberry jam (approximately 50 g of available carbohydrate) along with 220 ml coffee (1 teaspoon of coffee with 220 ml of boiling water) over a 5 minute period. Immediately after having consumed the meal (t=15), and every 15 minutes afterwards for a further 150 minutes, subject took a blood glucose reading.
Shear Banding:
The dry ingredients of 20 g Insoluble Pea Protein and 5 g guar gum were mixed with a teaspoon in a cup. 300 ml of water was then added to the cup. The water and the dry ingredients were then mixed with the teaspoon until uniformity was reached. This drink was then put through the "shear banding test" as described previously (See Table 8 for result).

Example 15 (as represented in FIG. 43) shows that Insoluble pea protein as the source of protein when included in the shear banding invention is effective at lowering post-prandial blood glucose when compared to Comparative Example 13 (represented in FIG. 44).

EXAMPLE 16

Subject 7 (shown in Table 1) took a baseline blood glucose reading (t=−15). 12 minutes later subject took another baseline blood glucose reading (t=−3). Subject mixed the dry ingredients of 20 g Soy Protein and 5 g guar gum in a cup with a teaspoon. 250 ml of water was then added to the to the cup. Subject then stirred the water with the dry ingredients until there was uniformity. The subject then consumed the drink formulation as quickly as possible and took another blood glucose reading (t=0). 10 minutes later (t=10) the subject took a blood glucose reading then consumed a meal consisting of 2 slices of white bread with 4 grams of butter and 23 grams of strawberry jam (approximately 50 g of available carbohydrate) along with 220 ml coffee (1 teaspoon of coffee with 220 ml of boiling water) over a 5 minute period. Immediately after having consumed the meal (t=15), and every 15 minutes afterwards for a further 150 minutes, subject took a blood glucose reading.
Shear Banding:
The dry ingredients of 20 g Soy Protein and 5 g guar gum were mixed with a teaspoon in a cup. 250 ml of water was then added to the cup. The water and the dry ingredients were then mixed with the teaspoon until uniformity was reached. This drink was then put through the "shear banding test" as described previously (See Table 8 for result).

Example 16 shows that Insoluble pea protein as the source of protein when included in the shear banding invention is effective at lowering post-prandial blood glucose when compared to Comparative Example 13 (represented in FIG. 44).

EXAMPLE 17

Shear banding:
The dry ingredients of 20 g Milk Protein Concentrate (MPC approximately 80% Casein Protein and 20% Whey Protein) and 1 gram of guar guam were added to a "stock bottle". 150 ml of water was then added to the stock bottle. The lid of the stock bottle was replaced and then the bottle was shaken vigorously for 10 seconds. This drink was then put through the "shear banding test" as described previously (See Table 8 for result).

EXAMPLE 18

Subject 7 (shown in Table 1) took a baseline blood glucose reading (t=−15). 12 minutes later subject took another baseline blood glucose reading (t=−3). Subject mixed the dry ingredients of 20 g Bovine Hide Gelatine (88% protein) and 5 g guar gum in a cup with a teaspoon. 250 ml of water was then added to the to the cup. Subject then stirred the water with the dry ingredients until there was uniformity. The subject then consumed the drink formulation as quickly as possible and took another blood glucose reading (t=0). 10 minutes later (t=10) the subject took a blood glucose reading then consumed a meal consisting of 2 slices of white bread with 4 grams of butter and 23 grams of strawberry jam (approximately 50 g of available carbohydrate) along with 220 ml coffee (1 teaspoon of coffee with 220 ml of boiling water) over a 5 minute period. Immediately after having consumed the meal (t=15), and every 15 minutes afterwards for a further 165 minutes, subject took a blood glucose reading.

Shear Banding:

The dry ingredients of 20 g Bovine Hide Gelatine (88% Protein) 5 g guar gum were mixed with a teaspoon in a cup. 250 ml of water was then added to the cup. The water and the dry ingredients were then mixed with the teaspoon until uniformity was reached. This drink was then put through the "shear banding test" as described previously (See Table 8 for result).

Example 18 shows that Bovine Hide Gelatine as the source of protein when included in the shear banding invention is effective at lowering post-prandial blood glucose when compared to Comparative Example 13 (represented in FIG. 44).

COMPARATIVE EXAMPLE 13

Subject 7 (shown in Table 1) took a baseline blood glucose reading (t=−15). 12 minutes later subject took another baseline blood glucose reading (t=−3). Subject took another glucose measurement at (t=0). 10 minutes later (t=10) the subject took a blood glucose reading then consumed a meal consisting of 2 slices of white bread with 4 grams of butter and 23 grams of strawberry jam (approximately 50 g of available carbohydrate) along with 220 ml coffee (1 teaspoon of coffee with 220 ml of boiling water) over a 5 minute period. Immediately after having consumed the meal (t=15), and every 15 minutes afterwards for a further 150 minutes, subject took a blood glucose reading.

The invention claimed is:

1. A drink for moderating blood glucose levels produced by a meal in a human subject suffering diabetes or impaired glucose tolerance (IGT), the drink comprising:
   at least one water soluble or water dispersible compound selected from the group consisting of amino acids, peptides and proteins in a total amount of at least 8 g on a dry weight basis per serving of drink;
   aqueous liquid in an amount of from 70 ml to 400 ml per serving; and wherein the drink exhibits shear banding when subject to the shear banding test herein described.

2. A drink according to claim 1, further comprising a polysaccharide in an amount of up to 10 g on a dry weight basis per serving of drink.

3. A drink according to claim 1, wherein water soluble or water dispersible compound is protein present in an amount of from 10 g to 40 g on a dry weight basis of the drink composition.

4. A drink according to claim 1, wherein the water soluble or water dispersible compound is a protein of plant or animal origin selected from the group consisting of casein and salts thereof and whey and hydrolysis products of whey.

5. A drink according to claim 1, wherein the drink comprises a polysaccharide which is a gallactomannan gum.

6. A drink composition according to claim 1, wherein the total polysaccharide content is from 1 g to 8 g per serving.

7. A drink according to claim 1, wherein the drink is for treatment of a subject suffering diabetes or IGT concomitantly with diabetes medication comprising at least one selected from the group consisting of biguanides, enzyme inhibitors, Sulfonylureas, meglitinides, thiazolidinediones and insulin and insulin analogues.

8. A drink according to claim 1 for administration to a subject suffering diabetes or IGT in a time period of immediately prior to no more than 30 minutes prior to ingestion of a meal.

9. A drink according to claim 1, wherein:
   (i) the water soluble or water dispersible compound is whey protein in an amount of from 10 g to 25 g on a dry weight basis per serving of drink;
   (ii) aqueous liquid is in an amount of from 125 ml to 175 ml per serving; and
   (iii) the composition comprises a polysaccharide selected from guar gum wherein guar gum is present in an amount of from 4 g to 6 g on a dry weight basis per serving of drink.

10. A kit for providing a serving of a drink for moderating blood glucose levels following a meal in a human subjects suffering diabetes or impaired glucose tolerance (IGT) the kit comprising:
    at least one serving of water soluble or water dispersible material selected from the group consisting of amino acids, peptides and proteins in a total amount of at least 8 g on a dry weight basis per serving of drink;
    a container having a level indicating a liquid volume of from 70 ml to 400 ml;
    a closure for the container; and
    a space within the container above the level to allow vigorous mixing prior to consumption wherein the mixing of the powder with water filled to the level provides a drink which exhibits shear banding on a standard rotating cylinder shear banding test as herein described.

11. A kit according to claim 10, wherein the water soluble or water dispersible material is a protein present in an amount of from 10 g to 40 g per serving on a dry weight basis.

12. A kit according to claim 10, wherein the protein is selected from soluble and colloidal protein of plant or animal origin and selected from the group consisting casein and salts thereof and whey and hydrolysis products of whey.

13. A kit according to claim 10, wherein the kit comprises a polysaccharide selected from galactomannan gum, in an amount of up to 10 g per serving.

14. A kit according to claim 13, wherein the total galactomannan gum content is from 1 g to 8 g per serving.

15. A kit according to claim 10, wherein the container has a closure and a volume at least 20% greater than the volume of the liquid and powder.

16. A kit according to claim 10, wherein:
    (i) the water soluble or water dispersible material is whey protein in an amount of from 10 g to 25 g per serving of drink;
    (ii) the polysaccharide is guar gum in an amount of from 4 g to 6 g per serving; and
    (iii) the container has a level indicating an aqueous liquid volume of from 125 ml to 175 ml.

* * * * *